US010808008B2

(12) United States Patent
Szeto

(10) Patent No.: US 10,808,008 B2
(45) Date of Patent: Oct. 20, 2020

(54) AROMATIC-CATIONIC PEPTIDES AND USES OF SAME

(71) Applicant: Cornell University, Ithaca, NY (US)

(72) Inventor: Hazel H. Szeto, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/380,484

(22) PCT Filed: Feb. 22, 2013

(86) PCT No.: PCT/US2013/027430
§ 371 (c)(1),
(2) Date: Aug. 22, 2014

(87) PCT Pub. No.: WO2013/126775
PCT Pub. Date: Aug. 29, 2013

(65) Prior Publication Data
US 2015/0010588 A1 Jan. 8, 2015

Related U.S. Application Data

(60) Provisional application No. 61/602,418, filed on Feb. 23, 2012.

(51) Int. Cl.
*A61K 38/07* (2006.01)
*C07K 5/11* (2006.01)

(52) U.S. Cl.
CPC ............ *C07K 5/1019* (2013.01); *A61K 38/07* (2013.01)

(58) Field of Classification Search
None
See application file for complete search history.

(56) References Cited

U.S. PATENT DOCUMENTS

| 4,522,811 | A | 6/1985 | Eppstein et al. |
| 5,674,534 | A | 10/1997 | Zale et al. |
| 5,716,644 | A | 2/1998 | Zale et al. |
| 8,143,219 | B2 * | 3/2012 | Szeto et al. .................. 514/15.4 |
| 2006/0084606 | A1 | 4/2006 | Szeto |
| 2009/0186802 | A1 | 7/2009 | Alluis et al. |
| 2009/0221514 | A1 | 9/2009 | Szeto et al. |
| 2012/0004720 | A1 | 1/2012 | Fogelman et al. |

FOREIGN PATENT DOCUMENTS

| WO | WO-96/40073 | 12/1996 |
| WO | WO-99/15154 | 4/1999 |
| WO | WO-00/38651 | 7/2000 |
| WO | WO-2005/072295 A2 | 8/2005 |
| WO | WO 2006/034056 | * 3/2006 |
| WO | WO-2006/034056 | 3/2006 |
| WO | WO-2009/108695 A2 | 9/2009 |
| WO | WO-2013/059071 | 4/2013 |

OTHER PUBLICATIONS

Liu et al, Novel cardiolipin therapeutic protects endothelial mitochondria during renal ischemia and mitigates microvascular rarefaction, inflammation, and fibrosis (Am J Physiol Renal Physiol 306: F970-F980, 2014).*

Alchi et al (Nephrol Dial Transplant (2010) 25: 3147-3154).*
Lesnefsky et al (Biochim Biophys Acta. 2008 ; 1777(7-8): 1020-1027).*
Frostegard et al (Arthritis & Rheumatism, vol. 52, No. 1, Jan. 2005, pp. 192-200).*
Horkko et al, Circulation. 2001;103:941-946.*
Anselem, S., "Liposome Technology," (1993), vol. 1, 2nd Ed. CRC Press, (26 pages).
Basova, L.V. et al., "Cardiolipin switch in mitochondria: shutting off the reduction of cytochrome c and turning on the peroxidase activity," Biochemistry, (2007), 46, pp. 3423-3434 (12 pages).
Chonn, A., et al., "Recent Advances in Liposomal Drug-Delivery Systems," Current Opinion in Biotechnology, (1995), vol. 6, pp. 698-708 (11 pages).
Cohen, B.E. et al. "Probing protein electrostatics with a synthetic fluorescent amino acid," Science, (2002), 296, pp. 1700-1703 (4 pages).
Gergely, et al., "Mitochondrial Hyperpolarization and ATP Depletion in Patients with Systemic Lupus Erythematosus," Arthritis Rheum, (2002), 46(1): 175-190, (16 pages).
Gregoriadis, "Engineering Liposomes for Drug Delivery: Progress and Problems," TIBTECH, (1995), vol. 13, pp. 527-537 (11 pages).
Hiratsuka, T., "New ribose-modified fluorescent analogs of adenine and guanine nucleotides available as substrates for various enzymes," Biochimica et Biophysica Acta, (1983), 742, pp. 496-508 (13 pages).
Horkko, et al., "The epitopes for some antiphospholipid antibodies are adducts of oxidized phospholipid and beta2 glycoprotein 1 (and other proteins)," PNAS, (1997), 94: 20356-10361 (7 pages).
International Preliminary Report on Patentability received in Application No. PCT/US2013/027430 dated Aug. 26, 2014 (7 pages).
International Search Report and Written Opinion received in Application No. PCT/US2013/027430 dated May 3, 2013 (9 pages).
Kagan, V.E. et al., "Mitochondrial targeting of electron scavenging antioxidants: Regulation of selective oxidation vs random chain reactions," Advanced Drug Delivery Reviews, (2009), 61, pp. 1375-1385 (11 pages).
Kagan, V.E. et al., "Mitochondria-targeted disruptors and inhibitors of cytochrome c/cardiolipin peroxidase complexes," Mol. Nutr. Food Res., (2009), 53, pp. 104-114 (11 pages).
Kalanxhi, E. et al., "Cytochrome c impaled: investigation of the extended lipid anchorage of a soluble protein to mitochondrial membrane models," Biochem. J., (2007), 407, pp. 179-187 (9 pages).
Kozarich, et al., "Next generation therapeutics Looking to the horizon," Current Opinion in Chemical Biology, (1998), 2: 439-440, (2 pages).
Li, et al., "Deranged Bioenergetics and Defective Redox Capacity in T Lymphocytes and Neutrophils are Related to Cellular Dysfunction and Increased Odixative Stress in Patients with Active Systemic Lupus Erythematosus," Clin Dev Immunol, (2012), vol. 2012, Article ID 548516 (12 pages).

(Continued)

*Primary Examiner* — Sergio Coffa
(74) *Attorney, Agent, or Firm* — Foley & Lardner LLP

(57) ABSTRACT

The present disclosure provides aromatic-cationic peptide compositions and methods of using the same. The methods comprise use of the peptides in electron transport, inhibition of cardiolipin peroxidation, and inhibition of apoptosis and necrosis to treat, prevent or ameliorate the symptoms of autoimmune diseases or condition.

3 Claims, 29 Drawing Sheets

(56) References Cited

OTHER PUBLICATIONS

Lichtenberg, Dov et al., "Liposomes: Preparation, Characterization, and Preservation," Methods Biochem. Anal., (1998), vol. 33, pp. 337-462.
Mizuguchi, H., et al., "Intratumor administration of fusogenic liposomes containing fragment A of diphtheria toxin suppresses tumor growth," Cancer Letters, (1996), vol. 100, No. 1-2, pp. 63-69.
Perl, et al., "Mitochondrial hyperpolarization: a checkpoint of T-cell life, death and autoimmunity," Trends Immunol, (2004), 25(7): 360-367, (8 pages).
Putney, "Encapsulation of proteins for improved delivery," Current Opinion in Chemical Biology, (1998), 2: 548-552 (5 pages).
Reddy, K., "Controlled-Release, Pegylation, Liposomal Formulations: New Mechanisms in the Delivery of Injectable Drugs," Ann. Pharmacother., (Jul./Aug. 2000), vol. 34, pp. 915-923 (9 pages).
Santucci, R. et al., "The Soret Circular Dichroism Spectrum as a Probe for the Heme Fe(III)-Met(80) Axial Bond in Horse Cytochrome c," Journal of Inorganic Biochemistry, (1997), 68, pp. 211-214 (4 pages).
Shidoji, et al., "Loss of Molecular Interaction between Cytochrome c and Cardiolipin Due to Lipid Peroxidation," Biochem Biophys Res Commun, (1999), 264: 343-349 (5 pages).
Sinibaldi, F. et al., "Extended cardiolipin anchorage to cytochrome c: a model for protein-mitochondrial membrane binding," J. Biol. Inorg. Chem., (2010), 15, pp. 689-700 (12 pages).
Sinibaldi, F. et al., "Insights into Cytochrome c-Cardiolipin Interaction. Role Played by Ionic Strength," Biochemistry, (2008), 47, pp. 6928-6935 (8 pages).
Sorice, et al., "Cardiolipin and its metabolites move from mitochondria to other cellular membranes during death receptor-mediated apoptosis," Cell Death and Differentiation, (2004), 11: 1133-1145 (13 pages).
Surewicz, W. et al., "Role of peptide structure in lipid-peptide interactions: A fluorescence study of the binding of pentagastrin-related pentapeptides to phospholipid vesicles," Biochemistry, (1984), 23, pp. 6072-6077 (6 pages).
Tsong, "Detection of Three Kinetic Phases in the Thermal Unfolding of Ferricytochrome c," Biochemistry, (1973), 12(12): 2209-2214 (6 pages).
Tuominen, E.K.J. et al., "Phospholipid-cytochrome c interaction," J. Biol. Chem., (2002), 277, pp. 8822-8826 (5 pages).
Vladimirov, Y.A. et al., "Mechanism of activation of cytochrome c peroxidase activity by cariolipin," Biochemistry (Moscow), (2006), 71(9), pp. 989-997 (10 pages).
Weiner, A.L., "Liposomes for Protein Delivery: Selecting Manufacture and Development Processes," Immunomethods, (1994), 4(3), pp. 201-209 (9 pages).
Woo, et al., "Prevalence and Clinical Associations of Lupus Anticoagulant, Anticardiolipin Antibodies, and Anti-beta2-glycoprotein I Antibodies in Patients with Systemic Lupus Erythematosus," Korean J Lab Med, (2010), 30:38-44 (7 pages).
English Translation of First Office Action received in Chinese Application No. 201380016624.6 dated Aug. 11, 2015 (13 pages).
Extended European Search Report received in EP Application No. 13751525.0 dated Aug. 6, 2015 (8 pages).
Sheu, et al., "Targeting antioxidants to mitochondria: A new therapeutic direction," Biochimica et Biophysica Acta 1762:256-265 (2006).
Thomas, et al., "Mitochondrial Targeting with Antioxidant Peptide SS-31 Prevents Mitochondrial Depolarization, Reduces Islet Cell Apoptosis, Increases Islet Cell Yield, and Improves Posttransplantation Function," J. Am. Soc. Nephrol. 18:213-222 (2007).
English translation of Second Office Action received in Chinese Application No. 201380016624.6 dated Mar. 28, 2016 (10 pages).
Orrenius, S., et al., "Cardiolipin oxidation sets cytochrome c free," Nature Chem. Biol. 1(4):188-189 (2005).
Sorice, M., et al., "Cardiolipin on the surface of apoptotic cells as a possible trigger for anti-phospholipid antibodies," Clin. Exp. Immunol., 122:277-284 (2000).
Szeto, H., "Cell-permeable, Mitochondrial-targeted, Peptide Antioxidants," AAPS J., 8(2): E277-E283 8(2)(2006).
Examination Report issued on Australian Application 2013222237, dated Nov. 15, 2016.
Frostegard et al., "Lipid Peroxidation is Enhanced in Patients with Systemic Lupus Erythematosus and is Associated with Arterial and Renal Disease Manifestations," Arthritis & Rheumatism, 2005, vol. 52, No. 1, pp. 192-200.
Office Action issued on Chinese Application 201380016624.6, dated Dec. 20, 2016, English translation.
Office Action issued on Japanese Application 2014-558892, dated Nov. 30, 2016 (English translation only).
Valesini et al., "New Facet of Antiphospholipid Antibodies," Ann N.Y. Acad. Sci, 2005, vol. 1051, pp. 487-497.
Examination Report issued on EP Application 13751525.0, dated Jan. 23, 2017.
Office Action issued on Chinese Application 201380016624.6, dated Sep. 13, 2017, English translation only.
Office Action issued on Japanese Application 2014-558892, dated Aug. 9, 2017 English translation only.
Office Action issued on Chinese Application 201380016624.6,, dated May 31, 2018.

\* cited by examiner

| | No SS31 (1:0) | With SS31 (1:1) |
|---|---|---|
| I ox | 17 nA | 25 nA |
| V ox | 100 mV | 100 mV |
| I red | −33 nA | −67 nA |
| V red | 200 mV | 200 mV |

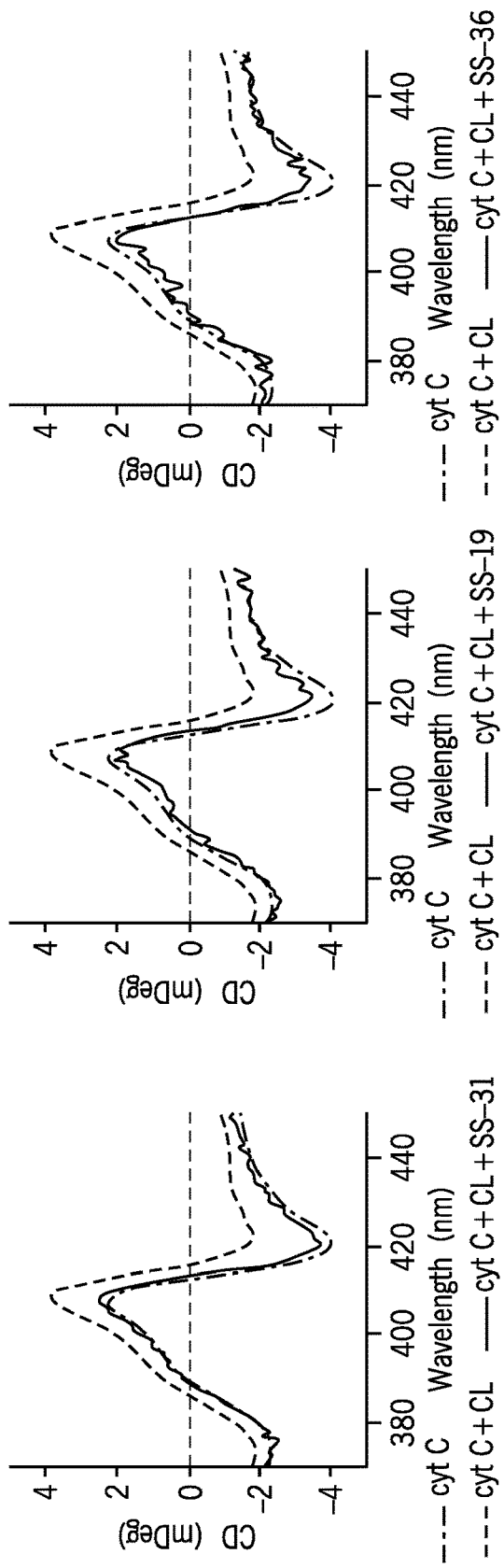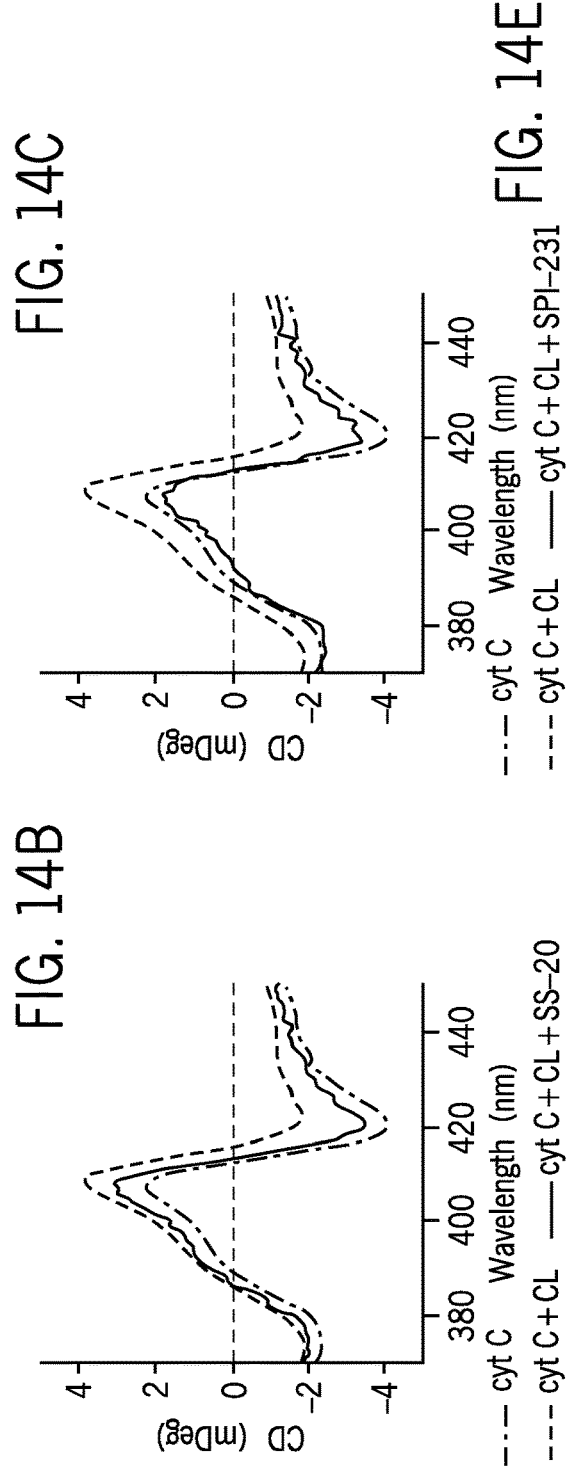
FIG. 14A  FIG. 14B  FIG. 14C  FIG. 14D  FIG. 14E

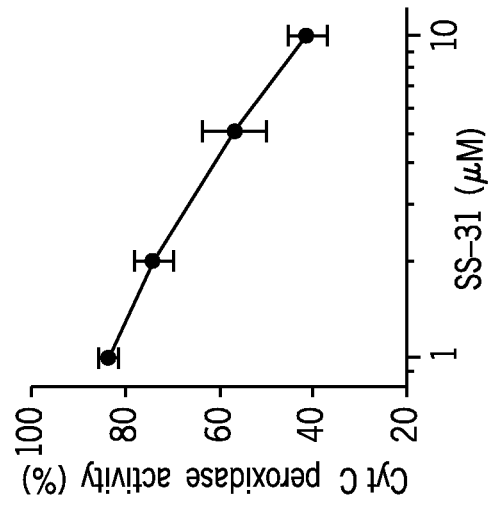
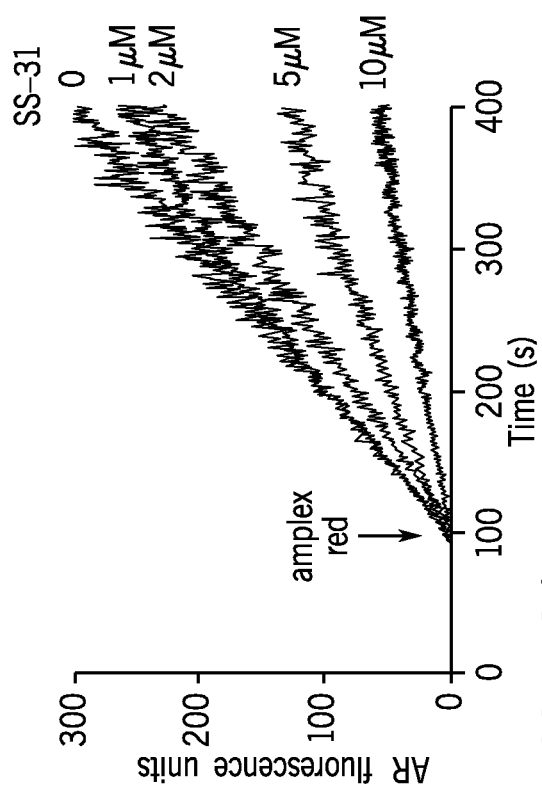
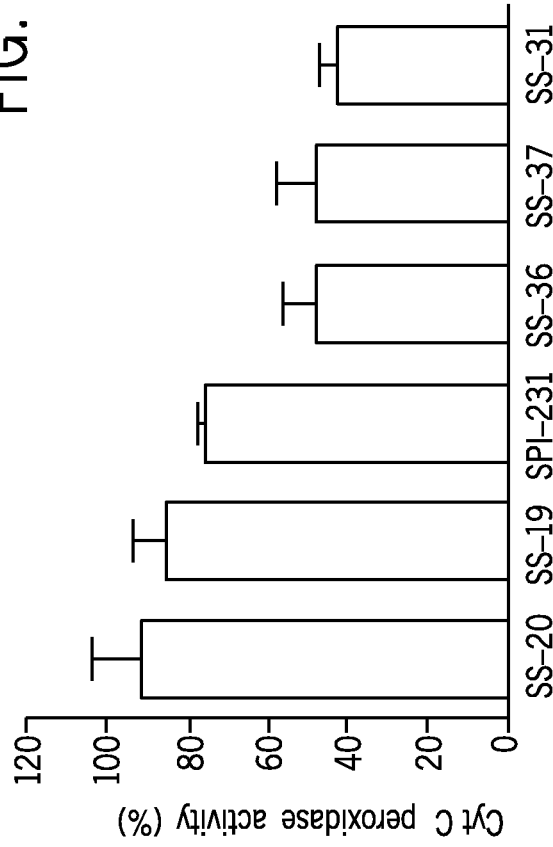
FIG. 19A
FIG. 19B
FIG. 19C

AROMATIC-CATIONIC PEPTIDES AND USES OF SAME

CROSS-REFERENCE TO RELATED APPLICATIONS

The present application is the U.S. National Stage of International Application No. PCT/US2013/027430, filed on Feb. 22, 2013, which claims the benefit of and priority to U.S. Provisional Patent Application No. 61/602,418, filed on Feb. 23, 2012, the contents of which are incorporated herein by reference in their entireties.

TECHNICAL FIELD

The present technology relates generally to aromatic-cationic peptide compositions and methods of use in treating, preventing or ameliorating the symptoms of autoimmune diseases or conditions.

BACKGROUND

Autoimmune diseases are characterized by immunologic responses to aspects of the body's own tissues. Autoimmune diseases can be broadly divided into two categories depending on the principal clinical and pathological disease features: those that damage many organs (systemic), and those where only a single organ or tissue is directly damaged by the autoimmune process (localized). Systemic autoimmune diseases, such as rheumatoid arthritis, systemic lupus erythematosus, antiphospholipid syndrome and systemic sclerosis, among others, are often characterized by autoantibodies reactive with a wide variety of autoantigens including DNA, cell surface molecules, and intracellular matrix proteins. Although the causes of systemic autoimmunity remain unclear, several immunological mechanisms have been implicated, along with genetic and environmental factors.

SUMMARY

In some aspects, the present technology provides methods for treating a subject suffering from an autoimmune disease, for reducing cardiolipin oxidation in a subject suffering from an autoimmune disease, and/or for reducing inflammation in a subject suffering from an autoimmune disease by administering a therapeutically effective amount of an aromatic-cationic peptide or a pharmaceutically acceptable salt thereof to the subject. In some embodiments of the methods, the autoimmune disease is characterized by an increased level of antibodies against cardiolipin. In some embodiments, the autoimmune disease is systemic lupus erythematosus or antiphospholipid syndrome.

In some embodiments of the methods disclosed herein, the aromatic-cationic peptide administered to the subject includes one or more peptides selected from the group consisting of 2',6'-Dmt-D-Arg-Phe-Lys-NH$_2$ (SS-02), Phe-D-Arg-Phe-Lys-NH$_2$ (SS-20), D-Arg-2',6'-Dmt-Lys-Phe-NH$_2$ (SS-31), 2',6'-Dmt-D-Arg-Phe-(atn)Dap-NH$_2$ (SS-19), where (atn)Dap is β-anthraniloyl-L-α,β-diaminopropionic acid, and 2',6'-Dmt-D-Arg-Ald-Lys-NH$_2$ (SS-36), where Ald is β-(6'-dimethylamino-2'-naphthoyl)alanine. In some embodiments, the salt is an acetate salt or trifluoroacetate salt. In some embodiments, the peptide comprises D-Arg-2',6'-Dmt-Lys-Phe-NH$_2$ (SS-31).

In some embodiments, administering a therapeutically effective amount of an aromatic-cationic peptide or a pharmaceutically acceptable salt thereof to the subject in need thereof (e.g., to treat an autoimmune disease, to reduce cardiolipin oxidation and/or to reduce inflammation in a subject suffering from an autoimmune disease) results in a reduction of one or more symptoms of an autoimmune disease. For example, in some embodiments, the subject is suffering from systemic lupus erythematosus, and aromatic-cationic peptide administration reduces or ameliorates one or more symptoms of systemic lupus erythematosus, wherein the symptoms of systemic lupus erythematosus are one or more symptoms selected from the group consisting of: increased cardiolipin antibody levels, fever, vascular thrombosis, thrombocytopenia, heart valve disease, livedo reticularis, pleuritis, pleural effusion, lupus pneumonitis, chronic diffuse interstitial lung disease, pulmonary hypertension, pulmonary emboli, pulmonary hemorrhage, shrinking lung syndrome, pericarditis, myocarditis, endocarditis, anemia, low platelet and white cell count, prolonged partial thromboplastin time, osteoarticular tuberculosis, myalgia, malar rash, discoid lupus, alopecia, mouth, nasal, urinary tract and vaginal ulcers, polyneuropathy, and intracranial hypertension syndrome.

In some embodiments, the aromatic-cationic peptide is administered orally, parenterally, intravenously, subcutaneously, transdermally, topically or by inhalation.

BRIEF DESCRIPTION OF THE FIGURES

FIG. 2 (lower panel) is a graph showing a cyclic voltammogram of the cytochrome c in solution with increasing SS-31 doses (20 mM Tris-borate-EDTA (TBE) buffer pH 7 at 100 mV/s.

FIG. 14A-14E are charts showing the peptides 2',6'-Dmt-D-Arg-Phe-(atn)Dap-NH$_2$ (SS-19) (FIG. 14B), Phe-D-Arg-Phe-Lys-NH$_2$ (SS-20) (FIG. 14D), D-Arg-2',6'-Dmt-Lys-Phe-NH$_2$ (SS-31) (FIG. 14A), 2',6'-Dmt-D-Arg-Ald-Lys-NH$_2$ (SS-36) (FIG. 14C) and D-Arg-Tyr-Lys-Phe-NH$_2$ (SPI-231) (FIG. 14E) protecting the heme environment of cytochrome c from the acyl chain of cardiolipin.

FIG. 19A-19C are charts showing the peptides D-Arg-2',6'-Dmt-Lys-Phe-NH$_2$ (SS-31) (FIG. 19A, 19B), 2',6'-Dmt-D-Arg-Phe-(atn)Dap-NH$_2$ (SS-19), Phe-D-Arg-Phe-Lys-NH$_2$ (SS-20), 2',6'-Dmt-D-Arg-Ald-Lys-NH$_2$ (SS-36), 2',6'-Dmt-D-Arg-Phe-Lys-Ald-NH$_2$ (SS-37) and D-Arg-Tyr-Lys-Phe-NH$_2$ (SPI-231) (FIG. 19C) preventing peroxidase activity in cytochrome c/cardiolipin complex.

DETAILED DESCRIPTION

Figure 1:
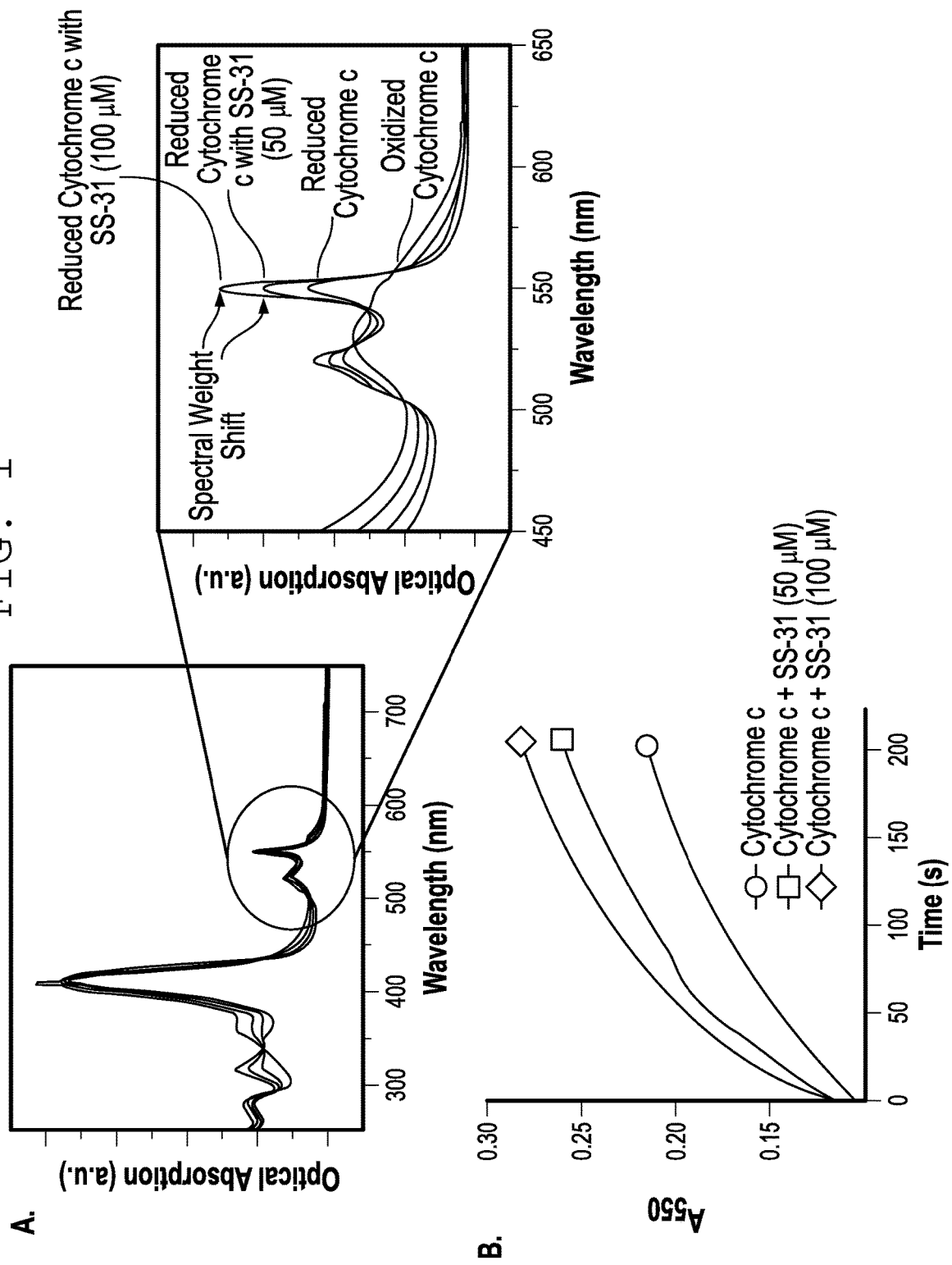
FIGS. 1A and 1B are charts showing that the peptide D-Arg-2',6'-Dmt-Lys-Phe-NH$_2$ (SS-31) increases the rate of cytochrome c reduction.

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs.

In practicing the present disclosure, many conventional techniques of cell biology, molecular biology, protein biochemistry, immunology, and bacteriology are used. These techniques are well-known in the art and are provided in any number of available publications, including *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989).

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, nasally, parenterally (intravenously, intramuscularly, intraperitoneally, or subcutaneously), topically, epicutaneously, rectally, intradermally, transdermally, inhalation, intraarterially, intracerebrally, interosseusly, intrathecally, iontophoretically, ocularly, intravaginaly, etc. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In some embodiments the term "effective amount" refers to a quantity sufficient to achieve a desired therapeutic effect, e.g., to aleviate or ameliorate the signs or symptoms of a disease or condition, such as antiphospholipid syndrome or systemic lupus erythematosus.

As used herein, "exogenous nucleic acid" refers to nucleic acid (e.g., DNA, RNA) that is not naturally present within a host cell but is introduced from an outside source. As used herein, exogenous nucleic acid refers to nucleic acid that has not integrated in to the genome of the host cell but remains separate, such as a bacterial plasmid nucleic acid. As used herein, "bacterial plasmid" refers to a circular DNA of bacterial origin which serves as a carrier of a sequence of interest and a means for expressing that sequence in a bacterial host cell.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide or an isolated cytochrome c protein would be free of materials that would interfere with diagnostic or therapeutic uses of the agent or would interfere with conductance, or electric properties of the peptide. Such interfering materials may include enzymes, hormones and other proteinaceous and nonproteinaceous solutes.

As used herein, "inducible promoter" refers to a promoter that is influenced by certain conditions, such as temperature or the presence of specific molecules, and promotes the expression of operably linked nucleic acid sequences of interest only when those conditions are met.

As used herein, "constitutive promoter" refers to a promoter that facilitates expression of operably linked nucleic acid sequences of interest under all or most environmental conditions.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "recombinant bacteria" refers to bacteria that have been engineered to carry and/or express one or more exogenous nucleic acid (e.g., DNA) sequences.

As used herein, the terms "treating" or "treatment" or "alleviation" refers to both therapeutic treatment and prophylactic or preventative measures, wherein the object is to prevent or slow down (lessen) the targeted pathologic condition or disorder. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to a compound that reduces the occurrence of the disorder or condition in the treated sample relative to an untreated control sample, or delays the onset or reduces the severity of one or more symptoms of the disorder or condition relative to the untreated control sample.

Aromatic-Cationic Peptides

The present technology relates to the use of aromatic-cationic peptides. In some embodiments, the peptides are useful in aspects related to treating or ameliorating symptoms, conditions or diseases characterized by the presence of anti-cardiolipin antibodies, such as antiphospholipid syndrome and systemic lupus erythematosus.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, about nine, or about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ∈-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, less than four, less than three, or less than two contiguous L-amino acids recognized by common proteases, irrespective of whether the amino acids are naturally or non-naturally occurring. In one embodiment, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \le p + 1$) | | | | | | | | | | | | | | | | | | |
|---|---|---|---|---|---|---|---|---|---|---|---|---|---|---|---|---|---|---|
| (r) | | | | | | | | | | | | | | | | | | |
| 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($2p_m \le p + 1$) | | | | | | | | | | | | | | | | | | |
|---|---|---|---|---|---|---|---|---|---|---|---|---|---|---|---|---|---|---|
| (r) | | | | | | | | | | | | | | | | | | |
| 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

| Aromatic groups and net positive charges ($3a \le p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

| Aromatic groups and net positive charges ($2a \le p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

In yet another aspect, the present technology provides an aromatic-cationic peptide or a pharmaceutically acceptable salt thereof such as acetate salt or trifluoroacetate salt. In some embodiments, the peptide comprises 1. at least one net positive charge;
2. a minimum of three amino acids;
3. a maximum of about twenty amino acids;
4. a relationship between the minimum number of net positive charges ($p_m$) and the total number of amino acid residues (r) wherein $3p_m$ is the largest number that is less than or equal to r+1; and
5. a relationship between the minimum number of aromatic groups (a) and the total number of net positive charges ($p_t$) wherein 2a is the largest number that is less than or equal to $p_t$+1, except that when a is 1, $p_t$ may also be 1.

In some embodiments, the peptide comprises the amino acid sequence Tyr-D-Arg-Phe-Lys-NH$_2$ (SS-01), 2',6'-Dmt-D-Arg-Phe-Lys-NH$_2$ (SS-02), Phe-D-Arg-Phe-Lys-NH$_2$ (SS-20) or D-Arg-2',6'-Dmt-Lys-Phe-NH$_2$ (SS-31). In some embodiments, the peptide comprises one or more of:

D-Arg-Dmt-Lys-Trp-NH$_2$;

D-Arg-Trp-Lys-Trp-NH$_2$;

D-Arg-2',6'-Dmt-Lys-Phe-Met-NH$_2$;

H-D-Arg-Dmt-Lys($N^?$Me)-Phe-NH$_2$;

H-D-Arg-Dmt-Lys-Phe(NMe)-NH$_2$;

H-D-Arg-Dmt-Lys($N^?$Me)-Phe(NMe)-NH$_2$;

H-D-Arg($N^?$Me)-Dmt(NMe)-Lys($N^?$Me)-Phe(NMe)-NH$_2$;

D-Arg-Dmt-Lys-Phe-Lys-Trp-NH$_2$;

D-Arg-Dmt-Lys-Dmt-Lys-Trp-NH$_2$;

D-Arg-Dmt-Lys-Phe-Lys-Met-NH$_2$;

D-Arg-Dmt-Lys-Dmt-Lys-Met-NH$_2$;

H-D-Arg-Dmt-Lys-Phe-Sar-Gly-Cys-NH$_2$;

H-D-Arg-Ψ[CH$_2$-NH]Dmt-Lys-Phe-NH$_2$;

H-D-Arg-Dmt-Ψ[CH$_2$-NH]Lys-Phe-NH$_2$;

H-D-Arg-Dmt-LysΨ[CH$_2$-NH]Phe-NH$_2$;

H-D-Arg-Dmt-Ψ[CH$_2$-NH]Lys-Ψ[CH$_2$-NH]Phe-NH$_2$;

Lys-D-Arg-Tyr-NH$_2$;

Tyr-D-Arg-Phe-Lys-NH$_2$;

2',6'-Dmt-D-Arg-Phe-Lys-NH$_2$;

Phe-D-Arg-Phe-Lys-NH$_2$;

Phe-D-Arg-Dmt-Lys-NH$_2$;

D-Arg-2'6'Dmt-Lys-Phe-NH$_2$;

H-Phe-D-Arg-Phe-Lys-Cys-NH$_2$;

Lys-D-Arg-Tyr-NH$_2$;

D-Tyr-Trp-Lys-NH$_2$;

Trp-D-Lys-Tyr-Arg-NH$_2$;

Tyr-His-D-Gly-Met;

Tyr-D-Arg-Phe-Lys-Glu-NH$_2$;

Met-Tyr-D-Lys-Phe-Arg;

D-His-Glu-Lys-Tyr-D-Phe-Arg;

Lys-D-Gln-Tyr-Arg-D-Phe-Trp-NH$_2$;

Phe-D-Arg-Lys-Trp-Tyr-D-Arg-His;

Gly-D-Phe-Lys-Tyr-His-D-Arg-Tyr-NH$_2$;

Val-D-Lys-His-Tyr-D-Phe-Ser-Tyr-Arg-NH$_2$;

Trp-Lys-Phe-D-Asp-Arg-Tyr-D-His-Lys;

Lys-Trp-D-Tyr-Arg-Asn-Phe-Tyr-D-His-NH$_2$;

Thr-Gly-Tyr-Arg-D-His-Phe-Trp-D-His-Lys;

Asp-D-Trp-Lys-Tyr-D-His-Phe-Arg-D-Gly-Lys-NH$_2$;

D-His-Lys-Tyr-D-Phe-Glu-D-Asp-D-His-D-Lys-Arg-Trp-NH$_2$;

Ala-D-Phe-D-Arg-Tyr-Lys-D-Trp-His-D-Tyr-Gly-Phe;

Tyr-D-His-Phe-D-Arg-Asp-Lys-D-Arg-His-Trp-D-His-Phe;

Phe-Phe-D-Tyr-Arg-Glu-Asp-D-Lys-Arg-D-Arg-His-Phe-NH$_2$;

Phe-Tyr-Lys-D-Arg-Trp-His-D-Lys-D-Lys-Glu-Arg-D-Tyr-Thr;

Tyr-Asp-D-Lys-Tyr-Phe-D-Lys-D-Arg-Phe-Pro-D-Tyr-His-Lys;

Glu-Arg-D-Lys-Tyr-D-Val-Phe-D-His-Trp-Arg-D-Gly-Tyr-Arg-D-Met-NH$_2$;,

Arg-D-Leu-D-Tyr-Phe-Lys-Glu-D-Lys-Arg-D-Trp-Lys-D-Phe-Tyr-D-Arg-Gly;

D-Glu-Asp-Lys-D-Arg-D-His-Phe-Phe-D-Val-Tyr-Arg-Tyr-D-Tyr-Arg-His-Phe-NH$_2$;

```
Asp-Arg-D-Phe-Cys-Phe-D-Arg-D-Lys-Tyr-Arg-D-Tyr-
Trp-D-His-Tyr-D-Phe-Lys-Phe;

His-Tyr-D-Arg-Trp-Lys-Phe-D-Asp-Ala-Arg-Cys-D-Tyr-
His-Phe-D-Lys-Tyr-His-Ser-NH₂;

Gly-Ala-Lys-Phe-D-Lys-Glu-Arg-Tyr-His-D-Arg-D-Arg-
Asp-Tyr-Trp-D-His-Trp-His-D-Lys-Asp;

Thr-Tyr-Arg-D-Lys-Trp-Tyr-Glu-Asp-D-Lys-D-Arg-His-
Phe-D-Tyr-Gly-Val-Ile-D-His-Arg-Tyr-Lys-NH₂;

Dmt-D-Arg-Phe-(atn)Dap-NH₂, where (atn)Dap is β-
anthraniloyl-L-α,β-diaminopropionic acid;

Dmt-D-Arg-Ald-Lys-NH₂, where Ald is β-(6'-
dimethylamino-2'-naphthoyl)alanine;

Dmt-D-Arg-Phe-Lys-Ald-NH₂, where Ald is β-(6'-
dimethylamino-2'-naphthoyl)alanine Dmt-D-Arg-Phe-(dns)Dap-NH₂ where (dns)Dap is
β-dansyl-L-α,β-diaminopropionic acid;

D-Arg-Tyr-Lys-Phe-NH₂;
and

D-Arg-Tyr-Lys-Phe-NH₂.
```

In some embodiments, "Dmt" refers to 2',6'-dimethyltyrosine (2',6'-Dmt) or 3',5'-dimethyltyrosine (3'5'Dmt).

In some embodiments, the peptide is defined by formula I:

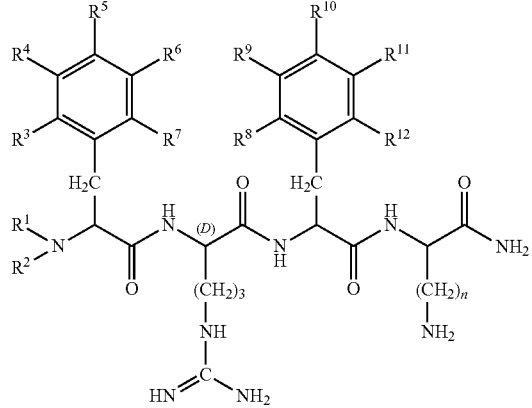

wherein $R^1$ and $R^2$ are each independently selected from
(i) hydrogen;
(ii) linear or branched $C_1$-$C_6$ alkyl;

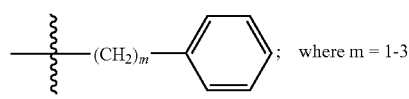

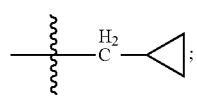

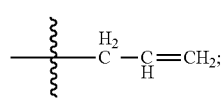

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In some emobdiments, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In some embodiments, the peptide is defined by formula II:

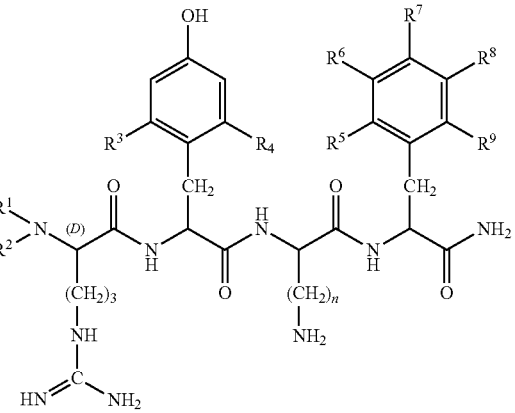

wherein $R^1$ and $R^2$ are each independently selected from
(i) hydrogen;
(ii) linear or branched $C_1$-$C_6$ alkyl;

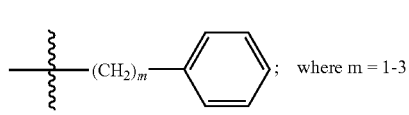

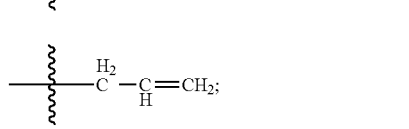

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;

(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In some embodiments, the peptide is defined by the formula:

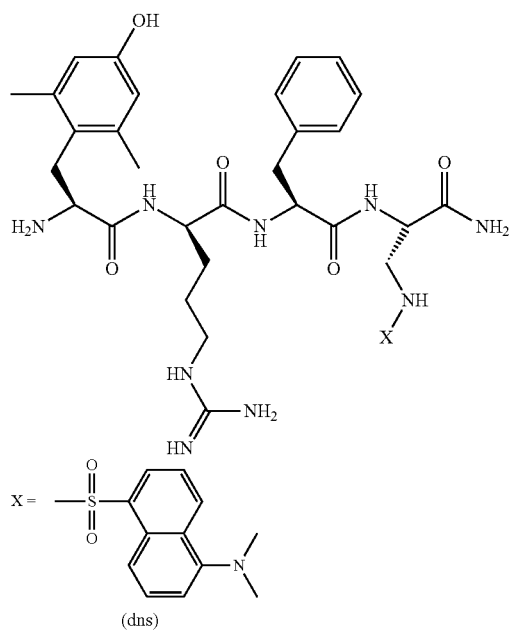

also represented as 2',6'-Dmt-D-Arg-Phe-(dns)Dap-NH$_2$, where (dns)Dap is β-dansyl-L-α,β-diaminopropionic acid (SS-17).

In some embodiments, the peptide is defined by the formula:

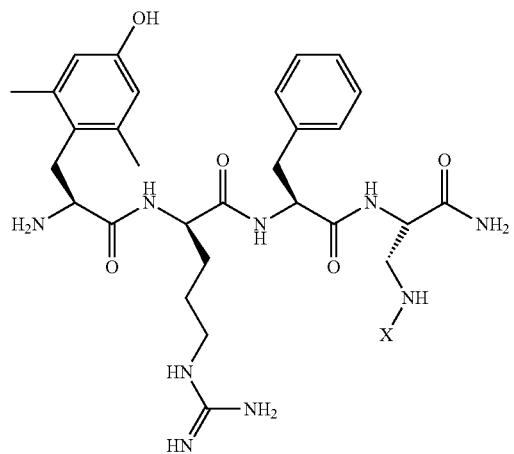

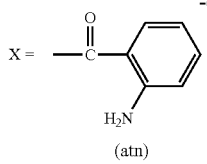

also represented as 2',6'-Dmt-D-Arg-Phe-(atn)Dap-NH$_2$ where (atn)Dap is β-anthraniloyl-L-α,β-diaminopropionic acid (SS-19). SS-19 is also referred to as [atn]SS-02.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the aromatic-cationic peptides have a core structural motif of alternating aromatic and cationic amino acids. For example, the peptide may be a tetrapeptide defined by any of formulas III to VI set forth below:

| | |
|---|---|
| Aromatic-Cationic-Aromatic-Cationic | (Formula III) |
| Cationic-Aromatic-Cationic-Aromatic | (Formula IV) |
| Aromatic-Aromatic-Cationic-Cationic | (Formula V) |
| Cationic-Cationic-Aromatic-Aromatic | (Formula VI) | wherein, Aromatic is a residue selected from the group consisting of: Phe (F), Tyr (Y), Trp (W), and Cyclohexylalanine (Cha); and Cationic is a residue selected from the group consisting of: Arg (R), Lys (K), Norleucine (Nle), and 2-amino-heptanoic acid (Ahe).

In some embodiments, the aromatic-cationic peptides described herein comprise all levorotatory (L) amino acids.

In one embodiment, the aromatic-cationic peptide has
1. at least one net positive charge;
2. a minimum of three amino acids;
3. a maximum of about twenty amino acids;
4. a relationship between the minimum number of net positive charges ($p_m$) and the total number of amino acid residues (r) wherein $3p_m$ is the largest number that is less than or equal to r+1; and
5. a relationship between the minimum number of aromatic groups (a) and the total number of net positive charges ($p_t$) wherein 2a is the largest number that is less than or equal to $p_t$+1, except that when a is 1, $p_t$ may also be 1.

In another embodiment, the invention provides a method for reducing the number of mitochondria undergoing a mitochondrial permeability transition (MPT), or preventing mitochondrial permeability transitioning in a removed organ of a mammal or treating or ameliorating symptoms, conditions or diseases characterized by the presence of anti-cardiolipin antibodies, such as antiphospholipid syndrome and systemic lupus erythematosus. The method comprises administering to the removed organ an effective amount of an aromatic-cationic peptide having:
at least one net positive charge;
a minimum of three amino acids;
a maximum of about twenty amino acids;
a relationship between the minimum number of net positive charges ($p_m$) and the total number of amino acid residues (r) wherein $3p_m$ is the largest number that is less than or equal to r+1; and
a relationship between the minimum number of aromatic groups (a) and the total number of net positive charges ($p_t$) wherein 2a is the largest number that is less than or equal to $p_t$+1, except that when a is 1, $p_t$ may also be 1.

In yet another embodiment, the invention provides a method of reducing the number of mitochondria undergoing mitochondrial permeability transition (MPT), or preventing mitochondria permeability transitioning in a mammal in need thereof, or treating or ameliorating symptoms, conditions or diseases characterized by the presence of anti-cardiolipin antibodies, such as antiphospholipid syndrome and systemic lupus erythematosus. The method comprises administering to the mammal an effective amount of an aromatic-cationic peptide having:

at least one net positive charge;
a minimum of three amino acids;
a maximum of about twenty amino acids;
a relationship between the minimum number of net positive charges ($p_m$) and the total number of amino acid residues (r) wherein 3 $p_m$ is the largest number that is less than or equal to r+1; and
a relationship between the minimum number of aromatic groups (a) and the total number of net positive charges ($p_t$) wherein 3a is the largest number that is less than or equal to $p_t$+1, except that when a is 1, $p_t$ may also be 1.

Aromatic-cationic peptides include, but are not limited to, the following illustrative peptides:

H-Phe-D-Arg Phe-Lys-Cys-NH$_2$

D-Arg-Dmt-Lys-Trp-NH$_2$;

D-Arg-Trp-Lys-Trp-NH$_2$;

D-Arg-Dmt-Lys-Phe-Met-NH$_2$;

H-D-Arg-Dmt-Lys($N^?$Me)-Phe-NH$_2$;

H-D-Arg-Dmt-Lys-Phe($N$Me)-NH$_2$;

H-D-Arg-Dmt-Lys($N^?$Me)-Phe($N$Me)-NH$_2$;

H-D-Arg($N^?$Me)-Dmt($N$Me)-Lys($N^?$Me)-Phe($N$Me)-NH$_2$;

D-Arg-Dmt-Lys-Phe-Lys-Trp-NH$_2$;

D-Arg-Dmt-Lys-Dmt-Lys-Trp-NH$_2$;

D-Arg-Dmt-Lys-Phe-Lys-Met-NH$_2$;

D-Arg-Dmt-Lys-Dmt-Lys-Met-NH$_2$;

H-D-Arg-Dmt-Lys-Phe-Sar-Gly-Cys-NH$_2$;

H-D-Arg-Ψ[CH$_2$-NH]Dmt-Lys-Phe-NH$_2$;

H-D-Arg-Dmt-Ψ[CH$_2$-NH]Lys-Phe-NH$_2$;

H-D-Arg-Dmt-LysΨ[CH$_2$-NH]Phe-NH$_2$;
and

H-D-Arg-Dmt-Ψ[CH$_2$-NH]Lys-T[CH$_2$-NH]Phe-NH$_2$,

Tyr-D-Arg-Phe-Lys-NH$_2$,

2',6'-Dmt-D-Arg-Phe-Lys-NH$_2$,

Phe-D-Arg-Phe-Lys-NH$_2$,

Phe-D-Arg-Dmt-Lys-NH$_2$,

D-Arg-2'6'Dmt-Lys-Phe-NH$_2$,

H-Phe-D-Arg-Phe-Lys-Cys-NH$_2$,

Lys-D-Arg-Tyr-NH$_2$,

D-Tyr-Trp-Lys-NH$_2$,

Trp-D-Lys-Tyr-Arg-NH$_2$,

Tyr-His-D-Gly-Met,

Tyr-D-Arg-Phe-Lys-Glu-NH$_2$,

Met-Tyr-D-Lys-Phe-Arg,

D-His-Glu-Lys-Tyr-D-Phe-Arg,

Lys-D-Gln-Tyr-Arg-D-Phe-Trp-NH$_2$,

Phe-D-Arg-Lys-Trp-Tyr-D-Arg-His,

Gly-D-Phe-Lys-Tyr-His-D-Arg-Tyr-NH$_2$,

Val-D-Lys-His-Tyr-D-Phe-Ser-Tyr-Arg-NH$_2$,

Trp-Lys-Phe-D-Asp-Arg-Tyr-D-His-Lys,

Lys-Trp-D-Tyr-Arg-Asn-Phe-Tyr-D-His-NH$_2$,

Thr-Gly-Tyr-Arg-D-His-Phe-Trp-D-His-Lys,

Asp-D-Trp-Lys-Tyr-D-His-Phe-Arg-D-Gly-Lys-NH$_2$,

D-His-Lys-Tyr-D-Phe-Glu-D-Asp-D-His-D-Lys-Arg-Trp-NH$_2$,

Ala-D-Phe-D-Arg-Tyr-Lys-D-Trp-His-D-Tyr-Gly-Phe,

Tyr-D-His-Phe-D-Arg-Asp-Lys-D-Arg-His-Trp-D-His-Phe,

Phe-Phe-D-Tyr-Arg-Glu-Asp-D-Lys-Arg-D-Arg-His-Phe-NH$_2$,

Phe-Tyr-Lys-D-Arg-Trp-His-D-Lys-D-Lys-Glu-Arg-D-Tyr-Thr,

Tyr-Asp-D-Lys-Tyr-Phe-D-Lys-D-Arg-Phe-Pro-D-Tyr-His-Lys,

Glu-Arg-D-Lys-Tyr-D-Val-Phe-D-His-Trp-Arg-D-Gly-Tyr-Arg-D-Met-NH$_2$,

Arg-D-Leu-D-Tyr-Phe-Lys-Glu-D-Lys-Arg-D-Trp-Lys-D-Phe-Tyr-D-Arg-Gly,

D-Glu-Asp-Lys-D-Arg-D-His-Phe-Phe-D-Val-Tyr-Arg-Tyr-D-Tyr-Arg-His-Phe-NH$_2$,

Asp-Arg-D-Phe-Cys-Phe-D-Arg-D-Lys-Tyr-Arg-D-Tyr-Trp-D-His-Tyr-D-Phe-Lys-Phe,

His-Tyr-D-Arg-Trp-Lys-Phe-D-Asp-Ala-Arg-Cys-D-Tyr-His-Phe-D-Lys-Tyr-His-Ser-NH$_2$,

Gly-Ala-Lys-Phe-D-Lys-Glu-Arg-Tyr-His-D-Arg-D-Arg-Asp-Tyr-Trp-D-His-Trp-His-D-Lys-Asp, and Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$;

Dmt-D-Arg-Phe-(atn)Dap-NH$_2$, where (atn)Dap is β-anthraniloyl-L-α,β-diaminopropionic acid;

Dmt-D-Arg-Phe-(dns)Dap-NH$_2$ where (dns)Dap is β-dansyl-L-α,β-diaminopropionic acid;

Dmt-D-Arg-Ald-Lys-NH$_2$, where Ald is β-(6'-dimethylamino-2'-naphthoyl)alanine;

Dmt-D-Arg-Phe-Lys-Ald-NH$_2$, where Ald is β-(6'-dimethylamino-2'-naphthoyl)alanine and D-Arg-Tyr-Lys-Phe-NH$_2$;
and D-Arg-Tyr-Lys-Phe-NH$_2$.

In some embodiments, peptides useful in the methods of the present invention are those peptides which have a tyrosine residue or a tyrosine derivative. In some embodiments, derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltryosine (Hmt).

In one embodiment, the peptide has the formula Tyr-D-Arg-Phe-Lys-NH$_2$ (referred to herein as SS-01). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH$_2$ (referred to herein as SS-02).

In a suitable embodiment, the amino acid residue at the N-terminus is arginine. An example of such a peptide is D-Arg-2',6'Dmt-Lys-Phe-NH$_2$ (referred to herein as SS-31).

In another embodiment, the amino acid at the N-terminus is phenylalanine or its derivative. In some embodiments, derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp). An example of such a peptide is Phe-D-Arg-Phe-Lys-NH$_2$ (referred to herein as SS-20). In one embodiment, the amino acid sequence of SS-02 is rearranged such that Dmt is not at the N-terminus. An example of such an aromatic-cationic peptide has the formula D-Arg-2',6'Dmt-Lys-Phe-NH$_2$ (SS-31).

In yet another embodiment, the aromatic-cationic peptide has the formula Phe-D-Arg-Dmt-Lys-NH$_2$ (referred to herein as SS-30). Alternatively, the N-terminal phenylalanine can be a derivative of phenylalanine such as 2',6'-dimethylphenylalanine (2'6'Dmp). SS-01 containing 2',6'-dimethylphenylalanine at amino acid position one has the formula 2',6'-Dmp-D-Arg-Dmt-Lys-NH$_2$.

In some embodiments, the aromatic cationic peptide comprises 2',6'-Dmt-D-Arg-Phe-(atn)Dap-NH$_2$ (SS-19), where (atn)Dap is β-anthraniloyl-L-α,β-diaminopropionic acid, 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), where Ald is β-(6'-dimethylamino-2'-naphthoyl)alanine, D-Arg-Tyr-Lys-Phe-NH$_2$ (SPI-231), and 2',6'-Dmt-D-Arg-Phe-(dns)Dap-NH$_2$ where (dns)Dap is β-dansyl-L-α,β-diaminopropionic acid (SS-17).

The peptides mentioned herein and their derivatives can further include functional analogs. A peptide is considered a functional analog if the analog has the same function as the stated peptide. The analog may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(O);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His(H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide. Non-limiting examples of analogs useful in the practice of the present invention include, but are not limited to, the aromatic-cationic peptides shown in Table 5.

TABLE 5

Examples of Peptide Analogs

| Amino Acid Position 1 | Amino Acid Position 2 | Amino Acid Position 3 | Amino Acid Position 4 | Amino Acid Position 5 | Amino Acid Position 6 | Amino Acid Position 7 | C-Terminal Modification |
|---|---|---|---|---|---|---|---|
| D-Arg | Dmt | Lys | Phe | | | | NH$_2$ |
| D-Arg | Dmt | Phe | Lys | | | | NH$_2$ |
| D-Arg | Phe | Lys | Dmt | | | | NH$_2$ |
| D-Arg | Phe | Dmt | Lys | | | | NH$_2$ |
| D-Arg | Lys | Dmt | Phe | | | | NH$_2$ |
| D-Arg | Lys | Phe | Dmt | | | | NH$_2$ |
| D-Arg | Dmt | Lys | Phe | Cys | | | NH$_2$ |
| D-Arg | Dmt | Lys | Phe | Glu | Cys | Gly | NH$_2$ |
| D-Arg | Dmt | Lys | Phe | Ser | Cys | | NH$_2$ |
| D-Arg | Dmt | Lys | Phe | Gly | Cys | | NH$_2$ |
| Phe | Lys | Dmt | D-Arg | | | | NH$_2$ |
| Phe | Lys | D-Arg | Dmt | | | | NH$_2$ |
| Phe | D-Arg | Phe | Lys | | | | NH$_2$ |
| Phe | D-Arg | Phe | Lys | Cys | | | NH$_2$ |
| Phe | D-Arg | Phe | Lys | Glu | Cys | Gly | NH$_2$ |
| Phe | D-Arg | Phe | Lys | Ser | Cys | | NH$_2$ |
| Phe | D-Arg | Phe | Lys | Gly | Cys | | NH$_2$ |
| Phe | D-Arg | Dmt | Lys | | | | NH$_2$ |
| Phe | D-Arg | Dmt | Lys | Cys | | | NH$_2$ |
| Phe | D-Arg | Dmt | Lys | Glu | Cys | Gly | NH$_2$ |
| Phe | D-Arg | Dmt | Lys | Ser | Cys | | NH$_2$ |
| Phe | D-Arg | Dmt | Lys | Gly | Cys | | NH$_2$ |
| Phe | D-Arg | Lys | Dmt | | | | NH$_2$ |
| Phe | Dmt | D-Arg | Lys | | | | NH$_2$ |
| Phe | Dmt | Lys | D-Arg | | | | NH$_2$ |
| Lys | Phe | D-Arg | Dmt | | | | NH$_2$ |
| Lys | Phe | Dmt | D-Arg | | | | NH$_2$ |
| Lys | Dmt | D-Arg | Phe | | | | NH$_2$ |

TABLE 5-continued

Examples of Peptide Analogs

| Amino Acid Position 1 | Amino Acid Position 2 | Amino Acid Position 3 | Amino Acid Position 4 | Amino Acid Position 5 | Amino Acid Position 6 | Amino Acid Position 7 | C-Terminal Modification |
|---|---|---|---|---|---|---|---|
| Lys | Dmt | Phe | D-Arg | | | | NH$_2$ |
| Lys | D-Arg | Phe | Dmt | | | | NH$_2$ |
| Lys | D-Arg | Dmt | Phe | | | | NH$_2$ |
| D-Arg | Dmt | D-Arg | Phe | | | | NH$_2$ |
| D-Arg | Dmt | D-Arg | Dmt | | | | NH$_2$ |
| D-Arg | Dmt | D-Arg | Tyr | | | | NH$_2$ |
| D-Arg | Dmt | D-Arg | Trp | | | | NH$_2$ |
| Trp | D-Arg | Phe | Lys | | | | NH$_2$ |
| Trp | D-Arg | Tyr | Lys | | | | NH$_2$ |
| Trp | D-Arg | Trp | Lys | | | | NH$_2$ |
| Trp | D-Arg | Dmt | Lys | | | | NH$_2$ |
| D-Arg | Trp | Lys | Phe | | | | NH$_2$ |
| D-Arg | Trp | Phe | Lys | | | | NH$_2$ |
| D-Arg | Trp | Lys | Dmt | | | | NH$_2$ |
| D-Arg | Trp | Dmt | Lys | | | | NH$_2$ |
| D-Arg | Lys | Trp | Phe | | | | NH$_2$ |
| D-Arg | Lys | Trp | Dmt | | | | NH$_2$ |
| Cha | D-Arg | Phe | Lys | | | | NH$_2$ |
| Ala | D-Arg | Phe | Lys | | | | NH$_2$ |

Cha = cyclohexyl

Under certain circumstances, it may be advantageous to use a peptide that also has opioid receptor agonist activity. Examples of analogs useful in the practice of the present invention include, but are not limited to, the aromatic-cationic peptides shown in Table 6.

TABLE 6

Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| Tyr | D-Arg | Phe | Lys | Cys | NH$_2$ |
| 2'6'Dmt | D-Arg | Phe | Lys | | NH$_2$ |
| 2'6'Dmt | D-Arg | Phe | Lys | Cys | NH$_2$ |
| 2'6'Dmt | D-Arg | Phe | Lys-NH(CH$_2$)$_2$—NH-dns | | NH$_2$ |
| 2'6'Dmt | D-Arg | Phe | Lys-NH(CH$_2$)$_2$—NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Lys | Cys | NH$_2$ |
| 2'6'Dmt | D-Cit | Phe | Ahp | | NH$_2$ |
| 2'6'Dmt | D-Arg | Phe | Orn | | NH$_2$ |
| 2'6'Dmt | D-Arg | Phe | Dab | | NH$_2$ |
| 2'6'Dmt | D-Arg | Phe | Dap | | NH$_2$ |
| 2'6'Dmt | D-Arg | Phe | Ahp(2-aminoheptanoic acid) | | NH$_2$ |
| Bio-2'6'Dmt | D-Arg | Phe | Lys | | NH$_2$ |
| 3'5'Dmt | D-Arg | Phe | Lys | | NH$_2$ |
| 3'5'Dmt | D-Arg | Phe | Orn | | NH$_2$ |
| 3'5'Dmt | D-Arg | Phe | Dab | | NH$_2$ |
| 3'5'Dmt | D-Arg | Phe | Dap | | NH$_2$ |
| Tyr | D-Arg | Tyr | Lys | | NH$_2$ |
| Tyr | D-Arg | Tyr | Orn | | NH$_2$ |
| Tyr | D-Arg | Tyr | Dab | | NH$_2$ |
| Tyr | D-Arg | Tyr | Dap | | NH$_2$ |
| 2'6'Dmt | D-Arg | Tyr | Lys | | NH$_2$ |
| 2'6'Dmt | D-Arg | Tyr | Orn | | NH$_2$ |
| 2'6'Dmt | D-Arg | Tyr | Dab | | NH$_2$ |
| 2'6'Dmt | D-Arg | Tyr | Dap | | NH$_2$ |

TABLE 6-continued

Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 2'6'Dmt | D-Arg | 2'6'Dmt | Lys | | NH$_2$ |
| 2'6'Dmt | D-Arg | 2'6'Dmt | Orn | | NH$_2$ |
| 2'6'Dmt | D-Arg | 2'6'Dmt | Dab | | NH$_2$ |
| 2'6'Dmt | D-Arg | 2'6'Dmt | Dap | | NH$_2$ |
| 3'5'Dmt | D-Arg | 3'5'Dmt | Arg | | NH$_2$ |
| 3'5'Dmt | D-Arg | 3'5'Dmt | Lys | | NH$_2$ |
| 3'5'Dmt | D-Arg | 3'5'Dmt | Orn | | NH$_2$ |
| 3'5'Dmt | D-Arg | 3'5'Dmt | Dab | | NH$_2$ |
| 2'6'Dmt | D-Arg | 2'6'Dmt | Lys | Cys | NH$_2$ |
| Tyr | D-Lys | Phe | Dap | | NH$_2$ |
| Tyr | D-Lys | Phe | Arg | | NH$_2$ |
| Tyr | D-Lys | Phe | Arg | Cys | NH$_2$ |
| Tyr | D-Lys | Phe | Lys | | NH$_2$ |
| Tyr | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | Phe | Arg | | NH$_2$ |
| 2'6'Dmt | D-Lys | Phe | Lys | | NH$_2$ |
| 3'5'Dmt | D-Lys | Phe | Orn | | NH$_2$ |
| 3'5'Dmt | D-Lys | Phe | Dab | | NH$_2$ |
| 3'5'Dmt | D-Lys | Phe | Dap | | NH$_2$ |
| 3'5'Dmt | D-Lys | Phe | Arg | | NH$_2$ |
| 3'5'Dmt | D-Lys | Phe | Arg | Cys | NH$_2$ |
| Tyr | D-Lys | Tyr | Lys | | NH$_2$ |
| Tyr | D-Lys | Tyr | Orn | | NH$_2$ |
| Tyr | D-Lys | Tyr | Dab | | NH$_2$ |
| Tyr | D-Lys | Tyr | Dap | | NH$_2$ |
| 2'6'Dmt | D-Lys | Tyr | Lys | | NH$_2$ |
| 2'6'Dmt | D-Lys | Tyr | Orn | | NH$_2$ |
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |
| 3'5'Dmt | D-Lys | Phe | Arg | | NH$_2$ |
| 3'5'Dmt | D-Orn | Phe | Arg | | NH$_2$ |
| Tyr | D-Lys | Tyr | Arg | | NH$_2$ |
| Tyr | D-Orn | Tyr | Arg | | NH$_2$ |
| Tyr | D-Dab | Tyr | Arg | | NH$_2$ |
| Tyr | D-Dap | Tyr | Arg | | NH$_2$ |
| 2'6'Dmt | D-Arg | 2'6'Dmt | Arg | | NH$_2$ |
| 2'6'Dmt | D-Lys | 2'6'Dmt | Arg | | NH$_2$ |
| 2'6'Dmt | D-Orn | 2'6'Dmt | Arg | | NH$_2$ |
| 2'6'Dmt | D-Dab | 2'6'Dmt | Arg | | NH$_2$ |
| 3'5'Dmt | D-Dap | 3'5'Dmt | Arg | | NH$_2$ |
| 3'5'Dmt | D-Arg | 3'5'Dmt | Arg | | NH$_2$ |
| 3'5'Dmt | D-Lys | 3'5'Dmt | Arg | | NH$_2$ |
| 3'5'Dmt | D-Orn | 3'5'Dmt | Arg | | NH$_2$ |
| Mmt | D-Arg | Phe | Lys | | NH$_2$ |
| Mmt | D-Arg | Phe | Orn | | NH$_2$ |
| Mmt | D-Arg | Phe | Dab | | NH$_2$ |
| Mmt | D-Arg | Phe | Dap | | NH$_2$ |
| Tmt | D-Arg | Phe | Lys | | NH$_2$ |
| Tmt | D-Arg | Phe | Orn | | NH$_2$ |
| Tmt | D-Arg | Phe | Dab | | NH$_2$ |
| Tmt | D-Arg | Phe | Dap | | NH$_2$ |
| Hmt | D-Arg | Phe | Lys | | NH$_2$ |

TABLE 6-continued

Peptide Analogs with Opioid Receptor Agonist Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Hmt | D-Arg | Phe | Orn | | NH$_2$ |
| Hmt | D-Arg | Phe | Dab | | NH$_2$ |
| Hmt | D-Arg | Phe | Dap | | NH$_2$ |
| Mmt | D-Lys | Phe | Lys | | NH$_2$ |
| Mmt | D-Lys | Phe | Orn | | NH$_2$ |
| Mmt | D-Lys | Phe | Dab | | NH$_2$ |
| Mmt | D-Lys | Phe | Dap | | NH$_2$ |
| Mmt | D-Lys | Phe | Arg | | NH$_2$ |
| Tmt | D-Lys | Phe | Lys | | NH$_2$ |
| Tmt | D-Lys | Phe | Orn | | NH$_2$ |
| Tmt | D-Lys | Phe | Dab | | NH$_2$ |
| Tmt | D-Lys | Phe | Dap | | NH$_2$ |
| Tmt | D-Lys | Phe | Arg | | NH$_2$ |
| Hmt | D-Lys | Phe | Lys | | NH$_2$ |
| Hmt | D-Lys | Phe | Orn | | NH$_2$ |
| Hmt | D-Lys | Phe | Dab | | NH$_2$ |
| Hmt | D-Lys | Phe | Dap | | NH$_2$ |
| Hmt | D-Lys | Phe | Arg | | NH$_2$ |
| Mmt | D-Lys | Phe | Arg | | NH$_2$ |
| Mmt | D-Orn | Phe | Arg | | NH$_2$ |
| Mmt | D-Dab | Phe | Arg | | NH$_2$ |
| Mmt | D-Dap | Phe | Arg | | NH$_2$ |
| Mmt | D-Arg | Phe | Arg | | NH$_2$ |
| Tmt | D-Lys | Phe | Arg | | NH$_2$ |
| Tmt | D-Orn | Phe | Arg | | NH$_2$ |
| Tmt | D-Dab | Phe | Arg | | NH$_2$ |
| Tmt | D-Dap | Phe | Arg | | NH$_2$ |
| Tmt | D-Arg | Phe | Arg | | NH$_2$ |
| Hmt | D-Lys | Phe | Arg | | NH$_2$ |
| Hmt | D-Orn | Phe | Arg | | NH$_2$ |
| Hmt | D-Dab | Phe | Arg | | NH$_2$ |
| Hmt | D-Dap | Phe | Arg | | NH$_2$ |
| Hmt | D-Arg | Phe | Arg | | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Additional peptides having opioid receptor agonist activity include 2',6'-Dmt-D-Arg-Ald-Lys-NH$_2$ (SS-36), where Ald is β-(6'-dimethylamino-2'-naphthoyl)alanine, and 2',6'-Dmt-D-Arg-Phe-Lys-Ald-NH$_2$ (SS-37), where Ald is β-(6'-dimethylamino-2'-naphthoyl)alanine.

Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltryosine (Hmt).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

The amino acids of the peptides shown in Tables 5 and 6 may be in either the L- or the D-configuration.

In some embodiments, the aromatic-cationic peptides include at least one arginine and/or at least one lysine residue. In some embodiments, the arginine and/or lysine residue serves as an electron acceptor and participates in proton coupled electron transport. Additionally or alternatively, in some embodiments, the aromatic-cationic peptide comprises a sequence resulting in a "charge-ring-charge-ring" configuration such as exists in SS-31. Additionally or alternatively, in some embodiments the aromatic-cationic peptides include thiol-containing residues, such as cysteine and methionine. In some embodiments, peptides including thiol-containing residues directly donate electrons and reduce cytochrome ccytochrome c. In some embodiments, the aromatic-cationic peptides include a vysteine at the N- and/or at the C-terminus of the peptide.

In some embodiments, peptide multimers are provided. For example in some embodiments, dimers are provided, such as an SS-20 dimer: Phe-D-Arg-Phe-Lys-Phe-D-Arg-Phe-Lys. In some embodiments, the dimer is an SS-31 dimer: D-Arg-2',6'-Dmt-Lys-Phe-D-Arg-2',6'-Dmt-Lys-Phe-NH$_2$. In some embodiments, the multimers are trimers, tetramers and/or pentamers. In some embodiments, the multimers include combinations of different monomer peptides (e.g., an SS-20 peptide linked to an SS-31 peptide). In some embodiments, these longer analogs are useful as therapeutic molecules.

In some embodiments, the aromatic-cationic peptides described herein comprise all levorotatory (L) amino acids.

Peptide Synthesis

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

One way of stabilizing peptides against enzymatic degradation is the replacement of an L-amino acid with a D-amino acid at the peptide bond undergoing cleavage. Aromatic cationic peptide analogs are prepared containing one or more D-amino acid residues in addition to the D-Arg residue already present. Another way to prevent enzymatic degradation is N-methylation of the α-amino group at one or more amino acid residues of the peptides. This will prevent peptide bond cleavage by any peptidase. Examples include: H-D-Arg-Dmt-Lys($N^\alpha$Me)-Phe-$NH_2$; H-D-Arg-Dmt-Lys-Phe(NMe)-$NH_2$; H-D-Arg-Dmt-Lys($N^\alpha$Me)-Phe(NMe)-$NH_2$; and H-D-Arg($N^\alpha$Me)-Dmt(NMe)-Lys($N^\alpha$Me)-Phe(NMe)-$NH_2$. $N^\alpha$-methylated analogues have lower hydrogen bonding capacity and can be expected to have improved intestinal permeability.

An alternative way to stabilize a peptide amide bond (—CO—NH—) against enzymatic degradation is its replacement with a reduced amide bond ($\Psi$C[$H_2$—NH]). This can be achieved with a reductive alkylation reaction between a Boc-amino acid-aldehyde and the amino group of the N-terminal amino acid residue of the growing peptide chain in solid-phase peptide synthesis. The reduced peptide bond is predicted to result in improved cellular permeability because of reduced hydrogen-bonding capacity. Examples include: H-D-Arg-$\Psi$[$CH_2$—NH]Dmt-Lys-Phe-$NH_2$, H-D-Arg-Dmt-$\Psi$[$CH_2$—NH]Lys-Phe-$NH_2$, H-D-Arg-Dmt-Lys$\Psi$[$CH_2$—NH]Phe-$NH_2$, H-D-Arg-Dmt-$\Psi$[$CH_2$—NH]Lys-$\Psi$[$CH_2$—NH]Phe-$NH_2$, etc.

Lipids

Cardiolipin is an important component of the inner mitochondrial membrane, where it constitutes about 20% of the total lipid composition. In mammalian cells, cardiolipin is found almost exclusively in the inner mitochondrial membrane where it is essential for the optimal function of enzymes involved in mitochondrial metabolism.

Cardiolipin is a species of diphosphatidylglycerol lipid comprising two phosphatidylglycerols connected with a glycerol backbone to form a dimeric structure. It has four alkyl groups and potentially carries two negative charges. As there are four distinct alkyl chains in cardiolipin, the molecule has the potential for great complexity. However, in most animal tissues, cardiolipin contains 18-carbon fatty alkyl chains with 2 unsaturated bonds on each of them. It has been proposed that the (18:2)4 acyl chain configuration is an important structural requirement for the high affinity of cardiolipin to inner membrane proteins in mammalian mitochondria. However, studies with isolated enzyme preparations indicate that its importance may vary depending on the protein examined.

Each of the two phosphates in the molecule can capture one proton. Although it has a symmetric structure, ionization of one phosphate happens at different levels of acidity than ionizing both, with pK1=3 and pK2>7.5. Hence, under normal physiological conditions (a pH of approximately 7.0), the molecule may carry only one negative charge. Hydroxyl groups (—OH and —O—) on the phosphate form stable intramolecular hydrogen bonds, forming a bicyclic resonance structure. This structure traps one proton, which is conducive to oxidative phosphorylation.

During the oxidative phosphorylation process catalyzed by Complex IV, large quantities of protons are transferred from one side of the membrane to another side causing a large pH change. Without wishing to be bound by theory, it has been suggested that cardiolipin functions as a proton trap within the mitochondrial membranes, strictly localizing the proton pool and minimizing pH in the mitochondrial intermembrane space. This function is thought to be due to the unique structure of cardiolipin, which, as described above, can trap a proton within the bicyclic structure while carrying a negative charge. Thus, cardiolipin can serve as an electron buffer pool to release or absorb protons to maintain the pH near the mitochondrial membranes.

In addition, cardiolipin has been shown to play a role in apoptosis. An early event in the apoptosis cascade involves cardiolipin. As discussed in more detail below, a cardiolipin-specific oxygenase produces cardiolipin-hydroperoxides which causes the lipid to undergo a conformational change. The oxidized cardiolipin then translocates from the inner mitochondrial membrane to the outer mitochondrial membrane where it is thought to form a pore through which cytochrome c is released into the cytosol. Cytochrome c can bind to the IP3 receptor stimulating calcium release, which further promotes the release of cytochrome c. When the cytoplasmic calcium concentration reaches a toxic level, the cell dies. In addition, extra-mitochondrial cytochrome c interacts with apoptotic activating factors, causing the formation of apoptosomal complexes and activation of the proteolytic caspase cascade.

Another consequence is that cytochrome c interacts with cardiolipin on the inner mitochondrial membrane with high affinity and forms a complex with cardiolipin that is non-productive in transporting electrons, but which acts as a cardiolipin-specific oxygenase/peroxidase. Indeed, interaction of cardiolipin with cytochrome c yields a complex whose normal redox potential is about minus (−) 400 mV more negative than that of intact cytochrome c. As a result, the cytochrome c/cardiolipin complex cannot accept electrons from mitochondrial complex III, leading to enhanced production of superoxide whose dismutation yields $H_2O_2$. The cytochrome c/cardiolipin complex also cannot accept electrons from superoxide. In addition, the high affinity interaction of cardiolipin with cytochrome c results in the activation of cytochrome c into a cardiolipin-specific peroxidase with selective catalytic activity toward peroxidation of polyunsaturated molecular cardiolipin. The peroxidase reaction of the cytochrome c/cardiolipin complex is driven by $H_2O_2$ as a source of oxidizing equivalents. Ultimately, this activity results in the accumulation of cardiolipin oxidation products, mainly cardiolipin-OOH and their reduction products, cardiolipin-OH. As noted above, it has been shown that oxygenated cardiolipin species play a role in mitochondrial membrane permeabilization and release of pro-apoptotic factors (including cytochrome c itself) into the cytosol. See e.g., Kagan et al., *Advanced Drug Delivery Reviews*, 61 (2009) 1375-1385; Kagan et al., *Mol. Nutr. Food Res.* 2009 January; 53(1): 104-114, both of which are incorporated herein by reference.

Cytochrome c is a globular protein whose major function is to serve as electron carrier from complex III (cytochrome c reductase) to complex IV (cytochrome c oxidase) in the mitochondrial electron transport chain. The prosthetic heme group is attached to the cytochrome c at Cys14 and Cys17, and is additionally bound by two coordinate axial ligands, His18 and Met80. The $6^{th}$ coordinate binding to Met80 prevents the interaction of the Fe with other ligands such as $O_2$, $H_2O_2$, NO, etc.

A pool of cytochrome c is distributed in the intermembrane space, with the rest being associated with the inner mitochondrial membrane (IMM) via both electrostatic and hydrophobic interactions. Cytochrome c is a highly cationic protein (8+ net charge at neutral pH) that can bind loosely to the anionic phospholipid cardiolipin on the IMM via electrostatic interaction. And, as noted above, cytochrome c can also bind tightly to cardiolipin via hydrophobic interaction. This tight binding of cytochrome c to cardiolipin results from the extension of an acyl chain of cardiolipin out of the lipid membrane and extending into a hydrophobic channel in the interior of cytochrome c (Tuominen et al., 2001; Kalanxhi & Wallace, 2007; Sinabaldi et al., 2010). This leads to the rupture of the Fe-Met80 bond in the cytochrome c heme pocket and results in a change in the heme environment, as shown by the loss of the negative Cotton peak in the Soret band region (Sinabaldi et al., 2008). It also leads to exposure of the heme Fe to $H_2O_2$ and NO.

Native cytochrome c has poor peroxidase activity because of its 6th coordination. However, upon hydrophobic binding to cardiolipin, cytochrome c undergoes structural changes that breaks the Fe-Met80 coordination and increases the exposure of the heme Fe to $H_2O_2$, and cytochrome c switches from an electron carrier to a peroxidase, with cardiolipin being the primary substrate (Vladimirov et al., 2006; Basova et al., 2007). As described above, cardiolipin peroxidation results in altered mitochondrial membrane structure, and the release of cytochrome c from the IMM to initiate caspase-mediated cell death.

Thus, in some embodiments, aromatic-cationic peptides as disclosed herein (such as D-Arg-2',6'-Dmt-Lys-Phe-NH$_2$, Phe-D-Arg-Phe-Lys-NH$_2$, 2',6'-Dmt-D-Arg-Phe-(atn)DapNH$_2$, where (atn)Dap is β-anthraniloyl-L-α,β-diaminopropionic acid, 2',6'-Dmt-D-Arg-Ald-Lys-NH$_2$, where Ald is β-(6'-dimethylamino-2'-naphthoyl)alanine, 2',6'-Dmt-D-Arg-Phe-Lys-Ald-NH$_2$, where Ald is β-(6'-dimethylamino-2'-naphthoyl)alanine, D-Arg-Tyr-Lys-Phe-NH$_2$, 2',6'-Dmt-D-Arg-Phe-(dns)Dap-NH$_2$ where (dns)Dap is β-dansyl-L-α,β-diaminopropionic acid or a pharmaceutically acceptable salt thereof, such as acetate or trifluoroacetate salt are administered to a subject in need thereof. Without wishing to be bound by theory, it is thought that the peptides contact (e.g., target) cytochrome c, cardiolipin or both, hinder the cardiolipin-cytochrome c interaction, inhibit the oxygenase/peroxidase activity of the cardiolipin/cytochrome c complex, inhibit cardiolipin-hydroperoxide formation, inhibit the translocation of cardiolipin to the outer membrane and/or inhibit the release of cytochrome c from the IMM. Additionally or alternatively, in some embodiments, the aromatic-cationic peptides disclosed herein include one or more of the following characteristics or functions: (1) are cell permeable and target the inner mitochondrial membrane; (2) selectively bind to cardiolipin via electrostatic interactions which facilitates the interaction of the peptide with cytochrome c; (3) interact with cytochrome c that is free and either loosely-bound or tightly-bound to cardiolipin; (4) protect the hydrophobic heme pocket of cytochrome c and/or inhibit cardiolipin from disrupting the Fe-Met80 bond; (5) promote π-π* interactions with the heme porphorin; (6) inhibit cytochrome c peroxidase activity; (7) promote kinetics of cytochrome c reduction; (8) prevent inhibition of cytochrome c reduction caused by cardiolipin; (9) promote electron flux in the mitochondrial electron transport chain and ATP synthesis. In some embodiments, the ability of the peptide to promote electron transport is not correlated with the ability of the peptide to inhibit peroxidase activity of the cytochrome c/cardiolipin complex. Thus, in some embodiments, the administered peptides inhibit, delay or reduce the interaction between cardiolipin and cytochrome c. Additionally or alternatively, in some embodiments, the administered peptides inhibit, delay or reduce the formation of cytochrome c/cardiolipin complexes. Additionally or alternatively, in some embodiments, the administered peptides inhibit, delay or reduce the oxygenase/peroxidase activity of the cytochrome c/cardiolipin complexes. Additionally or alternatively, in some embodiments, the administered peptides inhibit, delay or reduce apoptosis.

Additionally or alternatively, in some embodiments, the method relates to increasing cytochrome c reduction in a sample containing cytochrome c, comprising contacting the sample with an effective amount of an aromatic-cationic peptide or a salt thereof, such as acetate or trifluoroacetate salt. Additionally or alternatively, in some embodiments, the method relates to enhancing electron diffusion through cytochrome c in a sample containing cytochrome c, comprising contacting the sample with an effective amount of an aromatic-cationic peptide. Additionally or alternatively, in some embodiments, the method relates to enhancing electron capacity in cytochrome c in a sample containing cytochrome c, comprising contacting the sample with an effective amount of an aromatic-cationic peptide. Additionally or alternatively, in some embodiments, the method relates to inducing a novel π-π (interaction around cytochrome c in a sample containing cytochrome c, comprising contacting the sample with an effective amount of an aromatic-cationic peptide. In some embodiments, the aromatic-cationic peptide comprises D-Arg-2',6'-Dmt-Lys-Phe-NH$_2$. Additionally or alternatively, in some embodiments, the aromatic-cationic peptide comprises Phe-D-Arg-Phe-Lys-NH$_2$. In some embodiments, the method includes contacting the sample with an aromatic cationic peptide (e.g., D-Arg-2',6'-Dmt-Lys-Phe-NH$_2$ or Phe-D-Arg-Phe-Lys-NH$_2$) and cardiolipin. In some embodiments, the method includes contacting the sample with cardiolipin. In some embodiments, the aromatic cationic peptide comprises 2',6'-Dmt-D-Arg-Phe-(atn)Dap-NH$_2$ (SS-19), where (atn)Dap is β-anthraniloyl-L-α,β-diaminopropionic acid, 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), where Ald is β-(6'-dimethylamino-2'-naphthoyl)alanine, D-Arg-Tyr-Lys-Phe-NH$_2$ (SPI-231), and 2',6'-Dmt-D-Arg-Phe-(dns)Dap-NH$_2$ where (dns)Dap is β-dansyl-L-α,β-diaminopropionic acid (SS-17).

Prophylactic and Therapeutic Uses of Aromatic-Cationic Peptides

The aromatic-cationic peptides described herein are useful to prevent or treat disease. Specifically, the disclosure provides for both prophylactic and therapeutic methods of treating a subject at risk of (or susceptible to) disease by administering the aromatic-cationic peptides described herein. Accordingly, the present methods provide for the prevention and/or treatment of disease in a subject by administering an effective amount of an aromatic-cationic peptide to a subject in need thereof.

In one aspect, the disclosure provides a method of reducing the number of mitochondria undergoing mitochondrial permeability transition (MPT), or preventing mitochondrial permeability transitioning in a mammal in need thereof, the method comprising administering to the mammal an effective amount of one or more aromatic-cationic peptides described herein. In another aspect, the disclosure provides a method for increasing the ATP synthesis rate in a mammal in need thereof, the method comprising administering to the mammal an effective amount of one or more aromatic-cationic peptides described herein. In yet another aspect, the disclosure provides a method for reducing oxidative damage in a mammal in need thereof, the method comprising administering to the mammal an effective amount of one or more aromatic-cationic peptides described herein.

Oxidative Damage.

The peptides disclosed herein are useful in reducing oxidative damage in a mammal in need thereof. Mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical, superoxide anion radical, nitric oxide, hydrogen, hypochlorous acid (HOCl) and peroxynitrite anion. Oxidative damage is considered to be "reduced" if the amount of oxidative damage in a mammal, a removed organ, or a cell is decreased after administration of an effective amount of the aromatic cationic peptides described above. Typically, the oxidative damage is considered to be reduced if the oxidative damage is decreased by at least about 10%, at least about 25%, at least about 50%, at least about 75%, or at least about 90%, compared to a control subject not treated with the peptide.

In some embodiments, a mammal to be treated can be a mammal with a disease or condition associated with oxidative damage. The oxidative damage can occur in any cell, tissue or organ of the mammal. In humans, oxidative stress is involved in many diseases. Examples include atherosclerosis, Parkinson's disease, heart failure, myocardial infarction, Alzheimer's disease, schizophrenia, bipolar disorder, fragile X syndrome and chronic fatigue syndrome.

In some embodiments, a mammal may be undergoing a treatment associated with oxidative damage. For example, the mammal may be undergoing reperfusion. Reperfusion refers to the restoration of blood flow to any organ or tissue in which the flow of blood is decreased or blocked. The restoration of blood flow during reperfusion leads to respiratory burst and formation of free radicals.

In one embodiment, the mammal may have decreased or blocked blood flow due to hypoxia or ischemia. The loss or severe reduction in blood supply during hypoxia or ischemia may, for example, be due to thromboembolic stroke, coronary atherosclerosis, or peripheral vascular disease. Numerous organs and tissues are subject to ischemia or hypoxia. Examples of such organs include brain, heart, kidney, intestine and prostate. The tissue affected is typically muscle, such as cardiac, skeletal, or smooth muscle For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

The methods can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes and microglia. The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid β-protein. Examples of chronic neurodegenerative diseases associated with damage by free radicals include Parkinson's disease, Alzheimer's disease, Huntington's disease and Amyotrophic Lateral Sclerosis (also known as Lou Gherig's disease).

Mitochondrial Permeability Transitioning.

The peptides disclosed herein are useful in treating any disease or condition that is associated with mitochondria permeability transitioning (MPT). Such diseases and conditions include, but are not limited to, ischemia and/or reperfusion of a tissue or organ, hypoxia and any of a number of neurodegenerative diseases. Mammals in need of inhibiting or preventing of MPT are those mammals suffering from these diseases or conditions.

Apoptosis. The peptides disclosed herein are useful in treating diseases or conditions that are associated with apoptosis. Exemplary diseases or conditions include, but are not limited to, cancers such as colorectal, glioma, hepatic, neuroblastoma, leukaemias and lymphomata, and prostate; autoimmune diseases such as myasthenia gravis, systemic lupus erythematosus, inflammatory diseases, bronchial asthma, inflammatory intestinal disease, pulmonary inflammation; viral infections such as adenovirus and baculovirus and HIV-AIDS; neurodegenerative diseases such as Alzheimer's disease, amyotrophic lateral sclerosis, Parkinson's disease, retinitis pigmentosa and epilepsy; haematologic diseases such as aplastic anaemia, myelodysplastic syndrome, T CD4+ lymphocytopenia, and G6PD deficiency; tissue damage such as caused by myocardial infarction, cerebrovascular accident, ischaemic renal damage and polycystic kidney. Thus, in some embodiments, aromatic-cationic peptides as disclosed herein (such as D-Arg-2',6'-Dmt-Lys-Phe-NH$_2$, Phe-D-Arg-Phe-Lys-NH$_2$, 2',6'-Dmt-D-Arg-Phe-(atn)Dap-NH$_2$, where (atn)Dap is O-anthraniloyl-L-α,β-diaminopropionic acid, 2',6'-Dmt-D-Arg-Ald-Lys-NH$_2$, where Ald is β-(6'-dimethylamino-2'-naphthoyl)alanine, 2',6'-Dmt-D-Arg-Phe-Lys-Ald-NH$_2$, where Ald is β-(6'-dimethylamino-2'-naphthoyl)alanine and D-Arg-Tyr-Lys-Phe-NH$_2$, 2',6'-Dmt-D-Arg-Phe-(dns)Dap-NH$_2$ where (dns)Dap is β-dansyl-L-α,β-diaminopropionic acid or a pharmaceutically acceptable salt thereof, such as acetate or trifluoroacetate salt) are administered to a subject (e.g., a mammal such as a human) in need thereof. As noted above, it is thought that the peptides contact (e.g., target) cytochrome c, cardiolipin or both, hinder the cardiolipin-cytochrome c interaction, inhibit cardiolipin-hydroperoxide formation, inhibit the translocation of cardiolipin to the outer membrane, and/or inhibit the oxygenase/peroxidase activity. Thus, in some embodiments, the administered peptides inhibit, delay or reduce the interaction between cardiolipin and cytochrome c. Additionally or alternatively, in some embodiments, the administered peptides inhibit, delay or reduce the formation of cytochrome c/cardiolipin complexes. Additionally or alternatively, in some embodiments, the administered peptides inhibit, delay or reduce the oxygenase/peroxidase activity of the cytochrome c/cardiolipin complexes. Additionally or alternatively, in some embodiments, the administered peptides inhibit, delay or reduce apoptosis.

a. Antiphospholipid Syndrome and Systemic Lupus Erythematosus

The peptides disclosed herein are useful in treating autoimmune diseases or conditions, such as systemic autoimmune diseases. Antiphospholipid Syndrome (APS) and systemic lupus erythematosus (SLE) are examples of systemic autoimmune diseases that are characterized by the presence of circulating autoantibodies including anticardiolipin antibodies, anti-$\beta_2$ glycoprotein I, and lupus anticoagulant. As with other autoimmune diseases, the immune system attacks the body's cells and tissues, resulting in inflammation and tissue damage. APS is associated with vascular thrombosis, thrombocytopenia, heart valve disease, livedo reticularis, and/or pregnancy morbidity such as fetal death, miscarriage, and pre-eclampsia. SLE may be a subset of APS that is characterized by inflammatory reactions involving connective tissues. Inflammatory symptoms or conditions in SLE include: fever; lung conditions such as pleuritis, pleural effusion, lupus pneumonitis, chronic diffuse interstitial lung disease, pulmonary hypertension, pulmonary emboli, pulmonary hemorrhage, and shrinking lung syndrome; heart inflammation, including pericarditis, myocarditis, and endocarditis; hematologic conditions such as anemia, low platelet and white cell count; prolonged partial thromboplastin time; musculoskeletal issues such as joint pain and inflammation, osteoarticular tuberculosis, and myalgia; dermatologic conditions such as malar rash, discoid lupus, alopecia, mouth, nasal, urinary tract and vaginal ulcers; neurological conditions such as headaches, depression, anxiety, polyneuropathy, psychosis, intracranial hypertension syndrome. The course of disease is characterized by periods of acute flares alternating with remissions. There is currently no specific treatment for APS or SLE, and available treatment usually only involves preventing the acute flares and reducing their severity and duration when they occur.

Cardiolipin oxidation may be an important process in the inflammatory aspects of both APS and SLE. Accordingly, the aromatic-cationic peptides of the present disclosure (such as but not limited to 2',6'-Dmt-D-Arg-Phe-Lys-NH$_2$ (SS-02), Phe-D-Arg-Phe-Lys-NH$_2$ (SS-20) and D-Arg-2',6'-Dmt-Lys-Phe-NH$_2$ (SS-31), Dmt-D-Arg-Phe-(atn)Dap-NH$_2$ (SS-19), where (atn)Dap is β-anthraniloyl-L-α,β-diaminopropionic acid, and 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), or pharmaceutically acceptable salts thereof, such as acetate and trifluoroacetate salt) can be used to treat both of these diseases by preventing cardiolipin oxidation, cellular apoptosis, and resultant inflammation via extracellular exposure of cardiolipin to cardiolipin antibodies in a subject and/or the production of cardiolipin antibodies in a subject.

1. Cardiolipin Oxidation and Extracellular Exposure on Apoptotic Cells

The peptides disclosed herein are useful to prevent, inhibit or diminish cardiolipin oxidation. Cardiolipin is a unique phospholipid that is almost exclusively found on the inner mitochondrial membrane and at contact sites connecting the outer membrane and inner membrane. Cardiolipin domains are required for proper cristae formation and they are involved in the organization of respiratory complexes into higher-order supercomplexes to facilitate electron transfer. Cardiolipin is also required to keep cytochrome c in close proximity to the respiratory complexes for efficient electron transfer. The positively-charged cytochrome c interacts with the highly anionic cardiolipin via electrostatic interactions.

This cardiolipin-cytochrome c interaction is weakened by cardiolipin peroxidation, and the loss of this free cytochrome c into the cytosol initiates caspase-dependent apoptosis (Shidoji et al., 1999, Biochem Biophys Res Commun 264, 343-347). A remodeling of lipid membranes occurs during apoptosis, and phosphatidylserine moves from the inner leaflet of the plasma membrane to the outer leaflet. In a similar fashion, cardiolipin and its metabolites can relocate from the mitochondria to other intracellular organelles and to the cell surface (M. Sorice et al., 2004, Cell Death Differ 11, 1133-1145). Thus, cardiolipin on the surface of apoptotic cells may be the trigger for anti-cardiolipin antibodies.

2. Cardiolipin Oxidation and APS

Cardiolipin has been shown to be expressed on the surface of apoptotic cells and are recognized by antiphospholipid antibodies purified from patients with APS (M. Sorice et al., 2004, Cell Death Differ 11, 1133-1145). In addition, the expression of cardiolipin precedes the translocation of phosphatidylserine to the cell surface and DNA fragmentation. Horkko et al. reported that anti-phospholipid antibodies only bind to oxidized cardiolipin, and not reduced cardiolipin (Horkko et al., 1997, Proc Natl Acad Sci USA 94:10356-10361). This is consistent with the fact that cardiolipin must be oxidized to release cytochrome c and relocate to the cell surface. Furthermore, reactive groups of oxidized cardiolipin may form covalent adducts with $\beta_2$GP1, and these adducts may be epitopes for anticardiolipin antibodies.

3. Mitochondrial ATP Depletion and SLE

The peptides disclosed herein (such as but not limited to 2',6'-Dmt-D-Arg-Phe-Lys-NH$_2$ (SS-02), Phe-D-Arg-Phe-Lys-NH$_2$ (SS-20) and D-Arg-2',6'-Dmt-Lys-Phe-NH$_2$ (SS-31), Dmt-D-Arg-Phe-(atn)Dap-NH$_2$ (SS-19), where (atn)Dap is β-anthraniloyl-L-α,β-diaminopropionic acid, and 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), or pharmaceutically acceptable salts thereof, such as acetate and trifluoroacetate salt) are useful in to enhance ATP levels in dysfunctional mitochondria. Abnormal T-cell activation and cell death are thought to underlie the pathology of SLE, and like APS, cardiolipin peroxidation may contribute to this phenomenon. As in APS, anti-cardiolipin antibodies are found in SLE patients (Woo et al., Korean J Lab Med. 2010 February; 30(1):38-44). Lymphocytes and PMNs from SLE patients exhibit elevated mitochondrial potential, increased reactive oxygen species production, decreased intracellular ATP, increased lactate levels, and reduced intracellular glutathione (Perl et al., 2004, Int Rev Immunol 23:293-313; Perl et al., 2004, Trends Immunol 25, 360-367; Gergely, Jr. et al., 2002, Arthritis Rheum 46:175-190; Li et al., 2012, Clin Dev Immunol 2012, 548516). Thus, immune cells in SLE patients are prone to mitochondrial dysfunction and oxidative stress. Consistent with this theory, SLE T cells exhibit enhanced spontaneous apoptosis (Perl et al., 2004, Trends Immunol 25, 360-367).

Lymphocyte necrosis may also contribute to the inflammatory reaction common in SLE. Intracellular ATP concentration in lymphocytes is thought to be a key switch in the cell's selection to die via apoptosis or necrosis. Deficiencies in intracellular ATP cause lymphocytes to be more likely to die of necrosis, which may contribute to inflammation in SLE patients. Thus, without wishing to be bound by theory, ATP deficiency in the lymphocytes of SLE patients may predispose them to death by necrosis and lead to increased inflammatory symptoms.

4. Preventing Inflammation in APS or SLE Using Aromatic-Cationic Peptides

Aromatic-cationic peptides disclosed herein (such as but not limited to 2',6'-Dmt-D-Arg-Phe-Lys-NH$_2$ (SS-02), Phe-D-Arg-Phe-Lys-NH$_2$ (SS-20) and D-Arg-2',6'-Dmt-Lys-Phe-NH$_2$ (SS-31), Dmt-D-Arg-Phe-(atn)Dap-NH$_2$ (SS-19), where (atn)Dap is O-anthraniloyl-L-α,β-diaminopropionic acid, and 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), or pharmaceutically acceptable salts thereof, such as acetate and trifluoroacetate salt), are useful to prevent cardiolipin peroxidation. Such peptides are also useful to prevent inflammation in APS and SLE by preventing relocation of cardiolipin to the cell surface, thus eliminating epitopes for the generation of cardiolipin antibodies, preventing the reaction of cardiolipin with anti-cardiolipin antibodies, or by preventing ATP depletion and resulting necrosis in lymphocytes. Cardiolipin peroxidation is primarily mediated by the peroxidase activity of cytochrome c. About 15-20% of mitochondrial cytochrome c is tightly bound in a complex with cardiolipin via hydrophobic interaction whereby one or more acyl chains of cardiolipin is inserted into the hydrophobic channel of cytochrome c. The insertion of the acyl chain into cytochrome c disrupts the coordinate bond between Met80 and the heme Fe and exposes the sixth coordinate of heme Fe to $H_2O_2$, thus converting this enzyme into a peroxidase that can selectively catalyze the oxidation of cardiolipin.

The aromatic-cationic peptides disclosed herein, (such as but not limited to 2',6'-Dmt-D-Arg-Phe-Lys-NH$_2$ (SS-02), Phe-D-Arg-Phe-Lys-NH$_2$ (SS-20) and D-Arg-2',6'-Dmt-Lys-Phe-NH$_2$ (SS-31), Dmt-D-Arg-Phe-(atn)Dap-NH$_2$ (SS-19), where (atn)Dap is β-anthraniloyl-L-α,β-diaminopropionic acid, and 2',6'-Dmt-D-Arg-Ald-Lys-NH$_2$ (SS-36), where Ald is β-(6'-dimethylamino-2'-naphthoyl)alanine, 2',6'-Dmt-D-Arg-Phe-Lys-Ald-NH$_2$ (SS-37), or pharmaceutically acceptable salts thereof, such as acetate and trifluoroacetate salt), are cell-permeable and can selectively target and concentrate in the inner mitochondrial membrane. The aromatic-cationic peptides selectively target anionic phospholipids such as cardiolipin, phosphatidylserine, phosphatidic acid, and phosphatidylglycerol, with cardiolipin having the highest affinity with some peptides (see e.g., Example 21). In some embodiments, the aromatic-cationic peptides interact with cytochrome c and the interaction is enhanced in the presence of cardiolipin. In some embodiments, the peptides can penetrate within the cytochrome c protein in close proximity of the heme, and this penetration is enhanced in the presence of cardiolipin (see e.g., Example 22-25).

Without wishing to be bound by theory, by penetrating into the heme environment of cytochrome c, it is likely that the aromatic-cationic peptides interfere with the structural interaction between cardiolipin and cyt c, and prevent the rupture of the Met80-Fe coordinate and prevent cytochrome c from becoming a peroxidase (see e.g., Example 24). These aromatic-cationic peptides also increase π-π* interaction in the heme region and promote cytochrome c reduction.

The aromatic-cationic peptides disclosed herein can also enhance mitochondrial respiration, increase oxidative phosphorylation capacity, and reduce mitochondrial reactive oxygen species (see e.g., Examples 16 and 20). As a result, they can protect lymphocyte mitochondrial function, reduce cardiolipin peroxidation, inhibit apoptosis and necrosis, and inhibit or reduce the exposure of cardiolipin to trigger antibody production and/or inhibit contact between cardiolipin and cardiolipin antibodies.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in preventing or treating disease. Compounds for use in therapy can be tested in suitable animal model systems including, but not limited to rats, mice, chicken, pigs, cows, monkeys, rabbits, and the like, prior to testing in human subjects. Similarly, for in vivo testing, any of the animal model systems known in the art can be used prior to administration to human subjects.

Prophylactic Methods.

In one aspect, the invention provides a method for preventing, in a subject, disease by administering to the subject an aromatic-cationic peptide that prevents the initiation or progression of the condition. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression. The appropriate compound can be determined based on screening assays described above.

Therapeutic Methods.

Another aspect of the technology includes methods of treating disease in a subject for therapeutic purposes. In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the injury in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, β-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt. Additionally or alternatively, in other embodiments, the salt is a trifluoroacetate salt.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at about 0.001 to about 0.5 mg/kg/h, suitably from about 0.01 to about 0.1 mg/kg/h. In one embodiment, the is provided from about 0.1 to about 1.0 mg/kg/h, suitably from about 0.1 to about 0.5 mg/kg/h. In one embodiment, the dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Aromatic-Cationic Peptides in Electron Transfer

Mitochondrial ATP synthesis is driven by electron flow through the electron transport chain (ETC) of the inner mitochondrial membrane (IMM). Electron flow through the chain can be described as a series of oxidation/reduction processes. Electrons pass from electron donors (NADH or QH2), through a series of electron acceptors (Complexes I-IV), and ultimately to the terminal electron acceptor, molecular oxygen. cytochrome c, which is loosely associated with the IMM, transfers electrons between Complexes III and IV.

Rapid shunting of electrons through the ETC is important for preventing short-circuiting that would lead to electron escape and generation of free radical intermediates. The rate of electron transfer (ET) between an electron donor and electron acceptor decreases exponentially with the distance between them, and superexchange ET is limited to 20 Å. Long-range ET can be achieved in a multi-step electron hopping process, where the overall distance between donor and acceptor is split into a series of shorter, and therefore faster, ET steps. In the ETC, efficient ET over long distances is assisted by cofactors that are strategically localized along the IMM, including FMN, FeS clusters, and hemes. Aromatic amino acids such as Phe, Tyr and Trp can also facilitate electron transfer to heme through overlapping $\pi$ clouds, and this was specifically shown (see experimental examples) for cytochrome c. Amino acids with suitable oxidation potential (Tyr, Trp, Cys, Met) can act as stepping stones by serving as intermediate electron carriers. In addition, the hydroxyl group of Tyr can lose a proton when it conveys an electron, and the presence of a basic group nearby, such as Lys, can result in proton-coupled ET which is even more efficient.

Overexpression of catalase targeted to mitochondria (mCAT) has been shown to improve aging (e.g., reduce the symptoms) and prolong lifespan in mice. These examples identify "druggable" chemical compounds that can reduce mitochondrial oxidative stress and protect mitochondrial function. As mitochondria are the major source of intracellular reactive oxygen species (ROS), the antioxidant must be delivered to mitochondria in order to limit oxidative damage to mitochondrial DNA, proteins of the electron transport chain (ETC), and the mitochondrial lipid membranes. We discovered a family of synthetic aromatic-cationic tetrapeptides that selectively target and concentrate in the inner mitochondrial membrane (IMM). Some of these peptides contain redox-active amino acids that can undergo one-electron oxidation and behave as mitochondria-targeted antioxidants. The peptides disclosed herein, such as the peptide D-Arg-2'6'-Dmt-Tyr-Lys-Phe-NH$_2$ reduces mitochondrial ROS and protect mitochondrial function in cellular and animal studies. Recent studies show that this peptide can confer protection against mitochondrial oxidative stress comparable to that observed with mitochondrial catalase overexpression. Although radical scavenging is the most commonly used approach to reduce oxidative stress, there are other potential mechanisms that can be used, including facilitation of electron transfer to reduce electron leak and improved mitochondrial reduction potential.

Abundant circumstantial evidence indicates that oxidative stress contributes to many consequences of normal aging and several major diseases, including cardiovascular diseases, diabetes, neurodegenerative diseases, and cancer. Oxidative stress is generally defined as an imbalance of prooxidants and antioxidants. However, despite a wealth of scientific evidence to support increased oxidative tissue damage, large-scale clinical studies with antioxidants have not demonstrated significant health benefits in these diseases. One of the reasons may be due to the inability of the available antioxidants to reach the site of prooxidant production.

The mitochondrial electron transport chain (ETC) is the primary intracellular producer of ROS, and mitochondria themselves are most vulnerable to oxidative stress. Protecting mitochondrial function would therefore be a prerequisite to preventing cell death caused by mitochondrial oxidative stress. The benefits of overexpressing catalase targeted to mitochondria (mCAT), but not peroxisomes (pCAT), provided proof-of-concept that mitochondria-targeted antioxidants would be necessary to overcome the detrimental effects of aging. However, adequate delivery of chemical antioxidants to the IMM remains a challenge.

One peptide analog, D-Arg-2',6'-Dmt-Tyr-Lys-Phe-$NH_2$, possesses intrinsic antioxidant ability because the modified tyrosine residue is redox-active and can undergo one-electron oxidation. We have shown that this peptide can neutralize $H_2O_2$, hydroxyl radical, and peroxynitrite, and inhibit lipid peroxidation. The peptide has demonstrated remarkable efficacy in animal models of ischemia-reperfusion injury, neurodegenerative diseases, and metabolic syndrome.

The design of the mitochondria-targeted peptides incorporates and enhances one or more of the following modes of action: (i) scavenging excess ROS, (ii) reducing ROS production by facilitating electron transfer, or (iii) increasing mitochondrial reductive capacity. The advantage of peptide molecules is that it is possible to incorporate natural or unnatural amino acids that can serve as redox centers, facilitate electron transfer, or increase sulfydryl groups while retaining the aromatic-cationic motif required for mitochondria targeting.

EXAMPLES

The present invention is further illustrated by the following examples, which should not be construed as limiting in any way.
General Methods
Cytochrome c Reduction:

Increasing amounts of aromatic-cationic peptides were added to a solution of oxidized cytochrome c. The formation of reduced cytochrome c was monitored by absorbance at 500 nm. The rate of cytochrome c reduction was determined by non-linear analysis (Prizm software).

Time-resolved UV-Visible absorption spectroscopy was used to study the electron transport process of cytochrome c in the presence of peptides. Reduced cytochrome c was monitored by absorbance at a broad-band spectral range (200-1100 nm). The absorption changes were recorded with a UV/Visible spectrophotometer (Ultrospec 3300 pro, GE) in quartz cells with path lengths of 1 or 2 mm. N-acetyl-cysteine (NAC) and glutathione were used as electron donors to reduce oxidized cytochrome c. The rate constant of cytochrome c reduction was estimated by adding various concentrations of peptides. The dose dependence of the peptides was correlated to the cytochrome c reduction kinetics.

Mitochondrial $O_2$ Consumption and ATP Production:

Fresh mitochondria were isolated from rat kidney as described previously. Electron flux was measured by $O_2$ consumption (Oxygraph Clark electrode) as previously described using different substrates for C1 (glutamate/malate), C2 (succinate), and C3 (TMPD/ascorbate). Assays were carried out under low substrate conditions in order to avoid saturating the enzyme reactions. ATP production in isolated mitochondria was determined kinetically using the luciferase method (Biotherma) in a 96-well luminescence plate reader (Molecular Devices). The initial maximal rate for ATP synthesis was determined over the first minute.

Cyclic Voltammetry:

Cyclic voltammetry was performed using the Bioanalytical System CV-50W Voltammetric Analyzer using an Ag/AgCl/1 M KCl reference electrode with a potential of +0.237 V versus NHE (Biometra, Göttingen, Germany), and a platinum counter electrode. Gold wire electrodes were cleaned following an established protocols. Electrochemical studies of cytochrome c in solution were performed using mercaptopropanol-modified electrodes (incubation 24 h in 20 mM mercaptopropanol). Cyclic voltammograms with 20 µM cytochrome c in 1 M KCl and 10 mM sodium phosphate buffer, pH 7.4/7.8 were recorded. The formal potential was calculated as the midpoint between the anodic and cathodic peak potentials at different scan rates (100-400 mV/s) and diffusion coefficients from the peak currents at different scan rates according the Randles-Sevcik equation.

Example 1

Synthesis of Aromatic-Cationic Peptides

Solid-phase peptide synthesis is used and all amino acids derivatives are commercially available. After completion of peptide assembly, peptides are cleaved from the resin in the usual manner. Crude peptides are purified by preparative reversed-phase chromatography. The structural identity of the peptides is confirmed by FAB mass spectrometry and their purity is assessed by analytical reversed-phase HPLC and by thin-layer chromatography in three different systems. Purity of >98% will be achieved. Typically, a synthetic run using 5 g of resin yields about 2.0-2.3 g of pure peptides.

Example 2

The peptide D-Arg-2',6'-Dmt-Lys-Phe-$NH_2$ (SS-31) Facilitates Cytochrome c Reduction Absorption spectroscopy (UltroSpec 3300 Pro; 220-1100 nm) was used to determine if SS-31 modulates cytochrome c reduction (FIG. 1). Reduction of cytochrome c with glutathione is associated with multiple shifts in the Q band (450-650 nm), with a prominent shift at 550 nm. Addition of SS-31 produced significant spectral weight shift at 550 nm (FIG. 1A). Time-dependent spectroscopy show that SS-31 increased the rate of cytochrome c reduction (FIG. 1B). These data suggest that SS-31 altered the electronic structure of cytochrome c and enhanced the reduction of $Fe^{3+}$ to $Fe^{2+}$ heme. Accordingly, the aromatic-cationic peptides of the present disclosure are useful for altering the structure and oxidation state of cytochrome c, and are useful for the prevention or treatment of diseases or disorders characterized by dysregulation of cytochrome c.

Example 3

Figure 2:
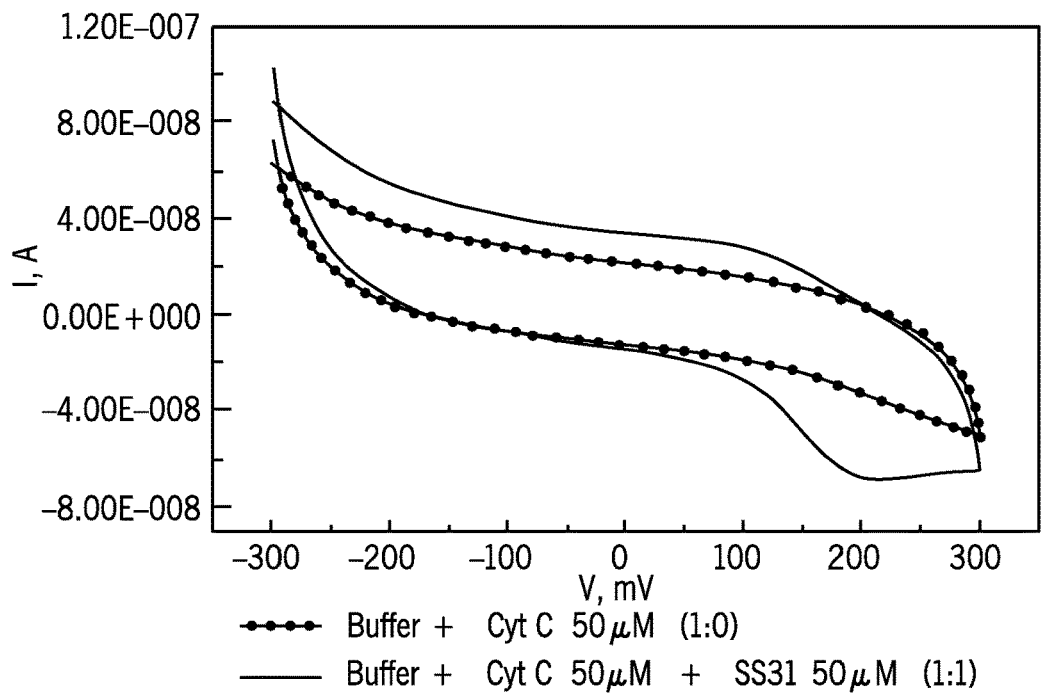
FIG. 2 (upper panel) is a chart showing that the peptide D-Arg-2',6'-Dmt-Lys-Phe-NH$_2$ (SS-31) enhances electron diffusion through cytochrome c.
Figure 2:
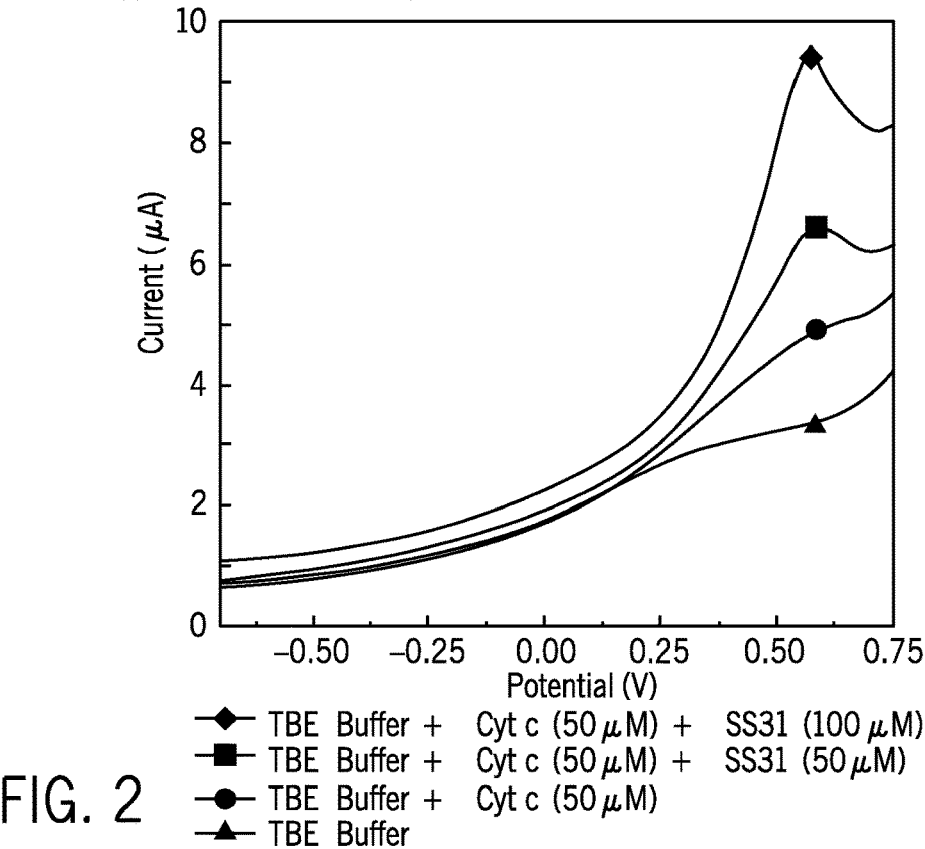

The peptide D-Arg-2',6'-Dmt-Lys-Phe-$NH_2$ (SS-31) Enhances Electron Diffusion Through Cytochrome c Cyclic voltammetry (CV) was carried out to determine if SS-31 altered electron flow and/or reduction/oxidation potentials of cytochrome c (FIG. 2, upper panel). CV was done using an Au working electrode, Ag/AgCl reference electrode, and Pt auxiliary electrode. SS-31 increased current for both reduction and oxidation processes of cytochrome c (FIG. 2, upper panel). SS-31 does not alter reduction/oxidation potentials (FIG. 2, upper panel), but rather increases electron flow through cytochrome c, suggesting that SS-31 decreases resistance between complexes III to IV. For FIG. 2 (lower panel) all voltammetric measurements were performed using the BASi-50W Voltammetric Analyzer coupled to a BASi C3 Cell Stand. An Ag/AgCl electrode was used as reference and glassy carbon and platinum electrodes were use for standard measurements. Prior to each measurement solutions were fully de-gassed with nitrogen to avoid electrode fouling. Cyclic voltammograms were taken for Tris-borate-EDTA (TBE) buffer, buffer plus cytochrome c, and buffer plus cytochrome c plus two different SS-31 doses as shown in FIG. 2 (lower panel). The current (electron diffusion rate) increases almost 200%, as the SS-31 dose is doubled with respect to cytochrome c (cytochrome c:SS-31=1:2). The result indicates that SS-31 promotes the electron diffusion in cytochrome c. Thus, the aromatic-cationic peptides of the present disclosure are useful for the prevention or treatment of diseases or disorders characterized by dysregulation of cytochrome c, for enhancing electron diffusion through cytochrome c, and for designing more sensitive bio-detectors.

Example 4

Figure 3A:
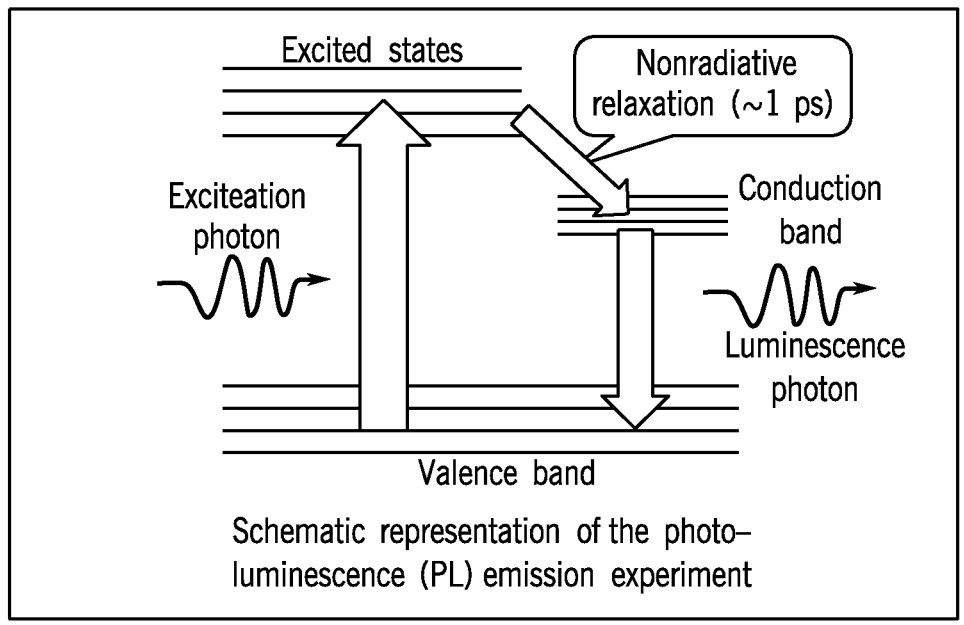
FIGS. 3A and 3B are charts showing that the peptide D-Arg-2',6'-Dmt-Lys-Phe-NH$_2$ (SS-31) enhances electron capacity in cytochrome c.
Figure 3B:
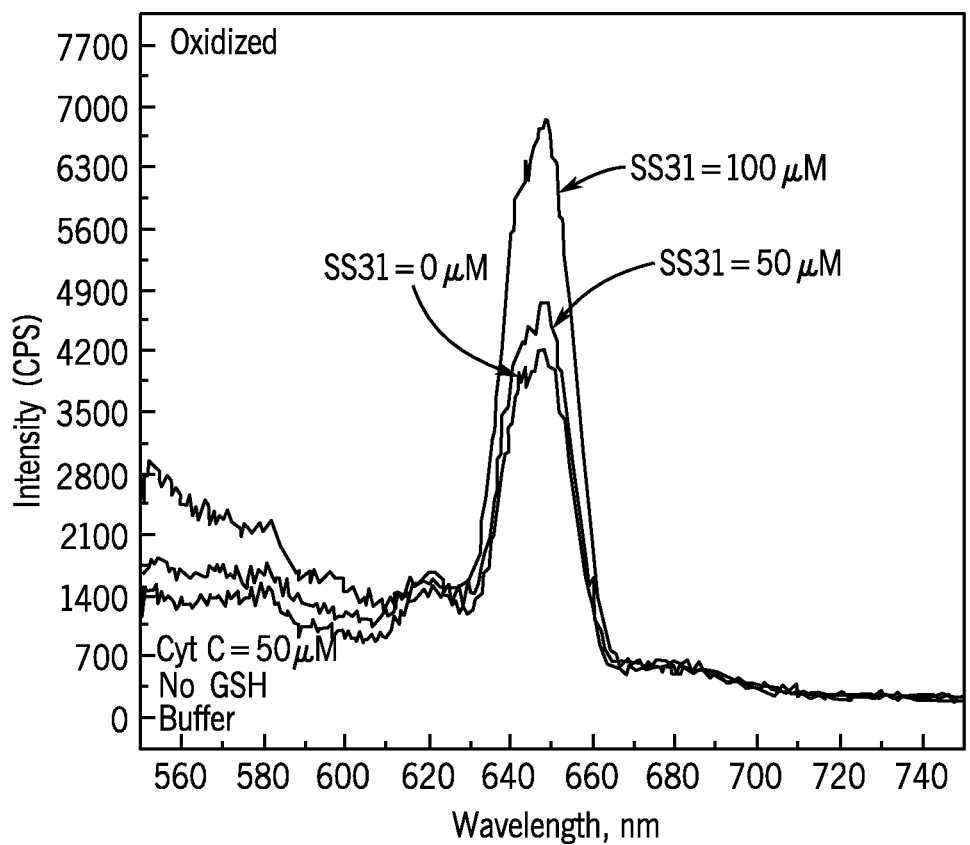

The Peptide D-Arg-2',6'-Dmt-Lys-Phe-NH$_2$ (SS-31) Enhances Electron Capacity in Cytochrome c Photoluminescence (PL) was carried out to examine the effects of SS-31 on the electronic structure of conduction band of the heme of cytochrome c, an energy state responsible for electronic transport (FIG. 3). A Nd:YDO4 laser (532.8 nm) was used to excite electrons in cytochrome c (FIG. 3A). Strong PL emission in cytochrome c state can be clearly identified at 650 nm (FIG. 3B). The PL intensity increased dose-dependently with the addition of SS-31, implying an increase of available electronic states in conduction band in cytochrome c (FIG. 3B). This suggests that SS-31 increases electron capacity of conduction band of cytochrome c, concurring with SS-31-mediated increase in current through cytochrome c. Accordingly, aromatic-cationic peptides of the present disclosure are useful for the prevention or treatment of diseases or disorders characterized by dysregulation of cytochrome c, for enhancing electron capacity in cytochrome c, and for treatment of diseases or disorders characterized by dysregulation of electron capacity in cytochrome c.

Example 5

Figure 4:
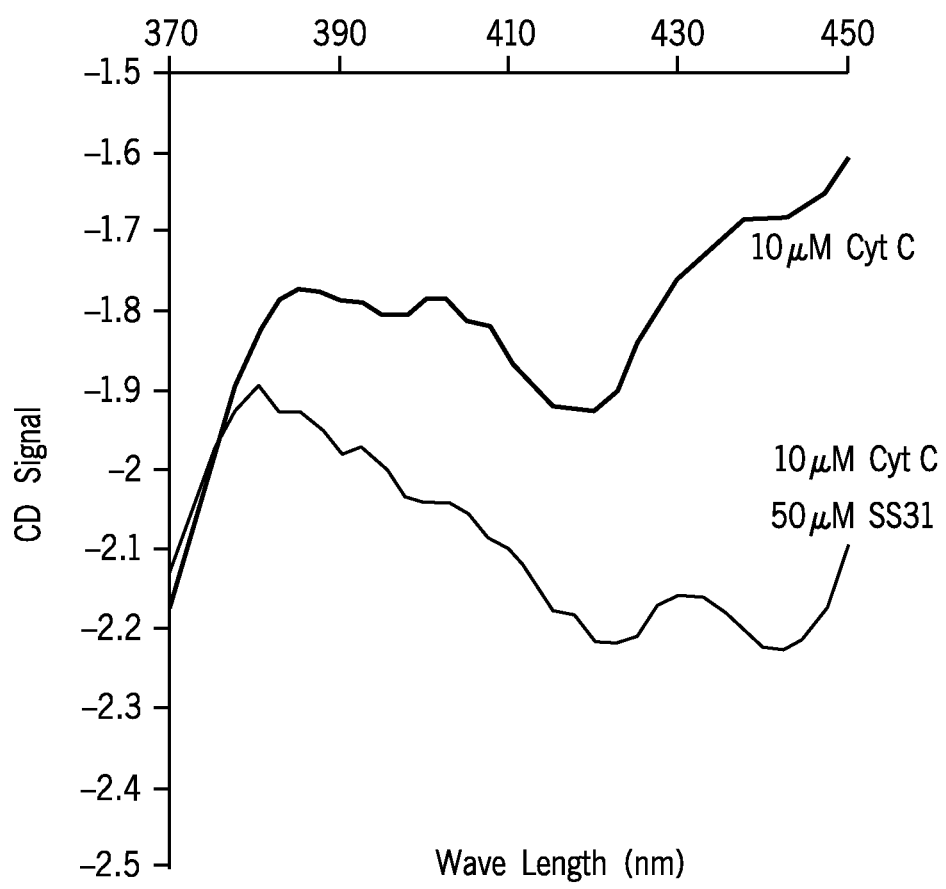
FIG. 4 is a chart showing that the peptide D-Arg-2',6'-Dmt-Lys-Phe-NH$_2$ (SS-31) induces novel π-π interactions around cytochrome c heme.

The Peptide D-Arg-2',6'-Dmt-Lys-Phe-NH$_2$ (SS-31) Induces Novel π-π Interactions Around Cytochrome c Heme Circular dichroism (Olis spectropolarimeter, DSM20) was carried out to monitor Soret band (negative peak at 415 nm), as a probe for the π-π* heme environment in cytochrome c (FIG. 4). SS-31 promoted a "red" shift of this peak to 440 nm, suggesting that SS-31 induced a novel heme-tyrosine π-π* transition within cytochrome c, without denaturing (FIG. 4). These results suggest that SS-31 must modify the immediate environment of the heme, either by providing an additional Tyr for electron tunneling to the heme, or by reducing the distance between endogenous Tyr residues and the heme. The increase in π-π* interaction around the heme would enhance electron tunneling which would be favorable for electron diffusion. Accordingly, aromatic-cationic peptides of the present disclosure are useful for the prevention or treatment of diseases or disorders characterized by dysregulation of cytochrome c, and to induce novel π-π interactions around cytochrome c heme.

Example 6

Figure 5A:
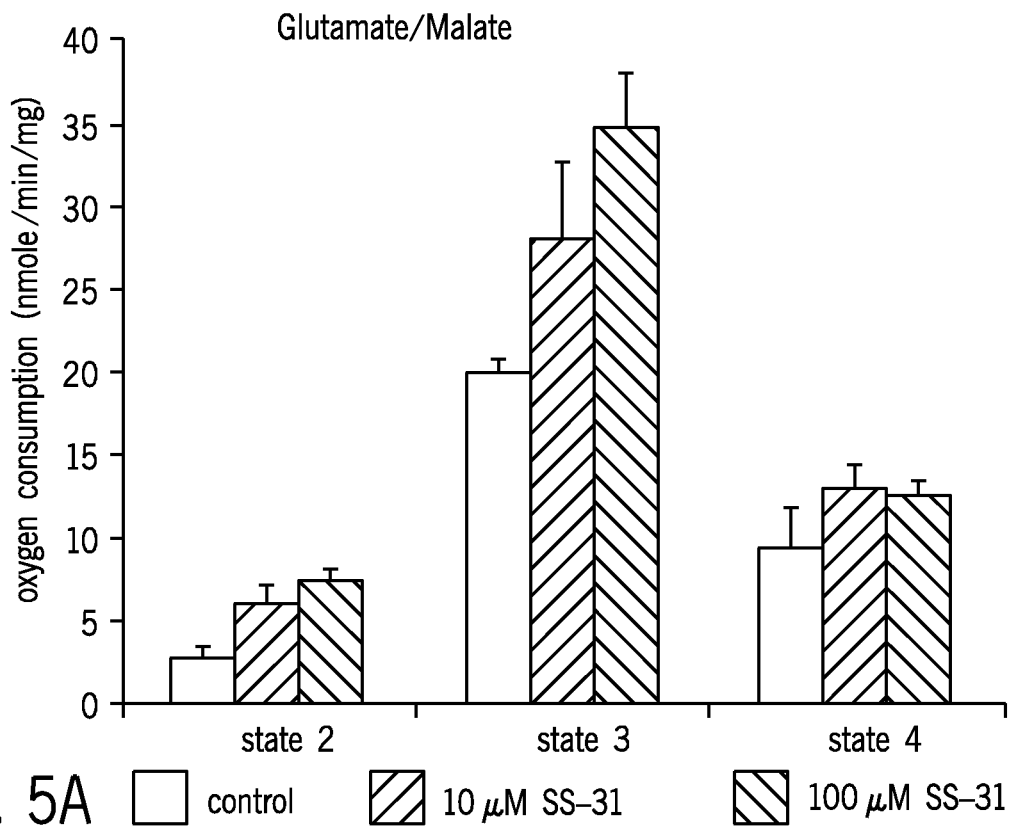
FIGS. 5A and 5B are charts showing that the peptide D-Arg-2',6'-Dmt-Lys-Phe-NH$_2$ (SS-31) increases O$_2$ consumption in isolated mitochondria.
Figure 5B:
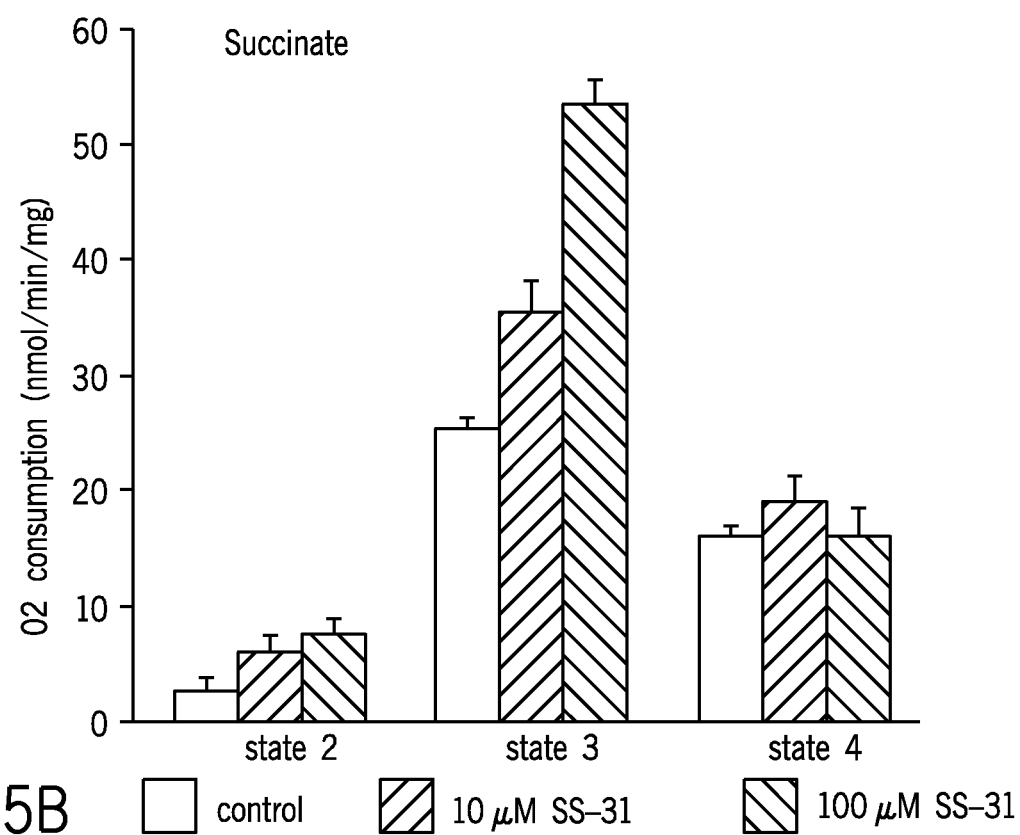

The Peptide D-Arg-2',6'-Dmt-Lys-Phe-NH$_2$ (SS-31) Increases Mitochondrial O$_2$ Consumption Oxygen consumption of isolated rat kidney mitochondria was determined using the Oxygraph (FIG. 5). Rates of respiration were measured in the presence of different concentrations of SS-31 in state 2 (400 µM ADP only), state 3 (400 µM ADP and 500 µM substrates) and state 4 (substrates only). All experiments were done in triplicate with n=4–7. The results show that SS-31 promoted electron transfer to oxygen without uncoupling mitochondria (FIG. 5). Accordingly, aromatic-cationic peptides of the present disclosure are useful for promoting electron transfer to oxygen without uncoupling mitochondria, increasing O$_2$ consumption, and treating diseases or conditions related to dysregulation of O$_2$ consumption in mitochondria.

Example 7

Figure 6:
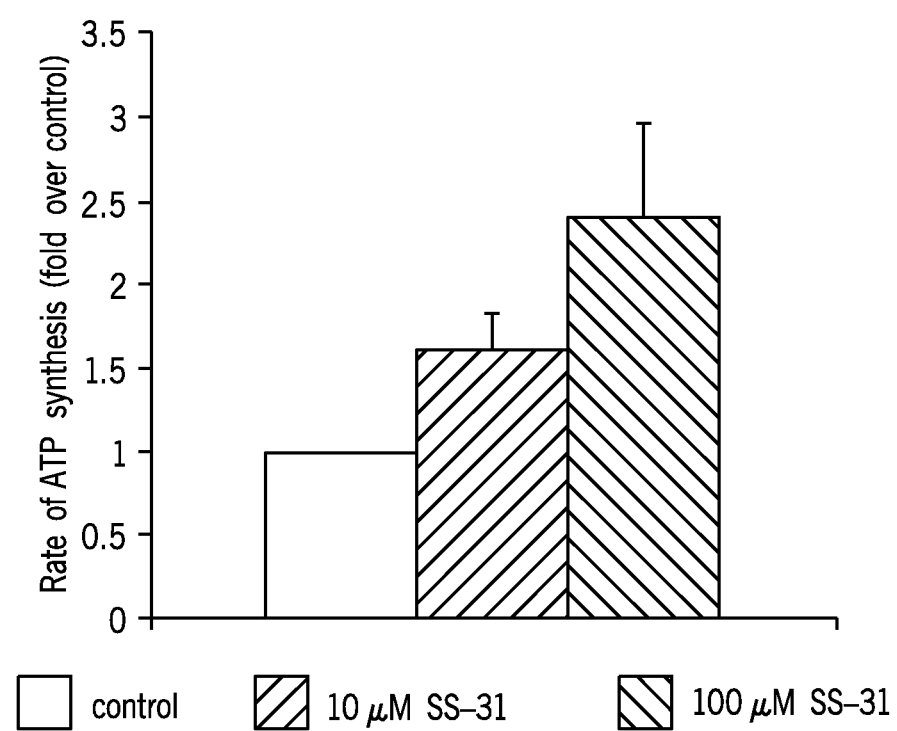
FIG. 6 is a chart showing that the peptide D-Arg-2',6'-Dmt-Lys-Phe-NH$_2$ (SS-31) increases ATP synthesis in isolated mitochondria.

The Peptide D-Arg-2',6'-Dmt-Lys-Phe-NH$_2$ (SS-31) Increases ATP Synthesis in Isolated Mitochondria The rate of mitochondrial ATP synthesis was determined by measuring ATP in respiration buffer collected from isolated mitochondria 1 min after addition of 400 mM ADP (FIG. 6). ATP was assayed by HPLC. All experiments were carried out in triplicate, with n=3. Addition of SS-31 to isolated mitochondria dose-dependently increased the rate of ATP synthesis (FIG. 6). These results show that the enhancement of electron transfer by SS-31 is coupled to ATP synthesis. Accordingly, aromatic-cationic peptides of the present disclosure are useful for increasing ATP synthesis in mitochondria and for treating diseases or disorder characterized by dysregulation of ATP synthesis.

Example 8

Figure 7:
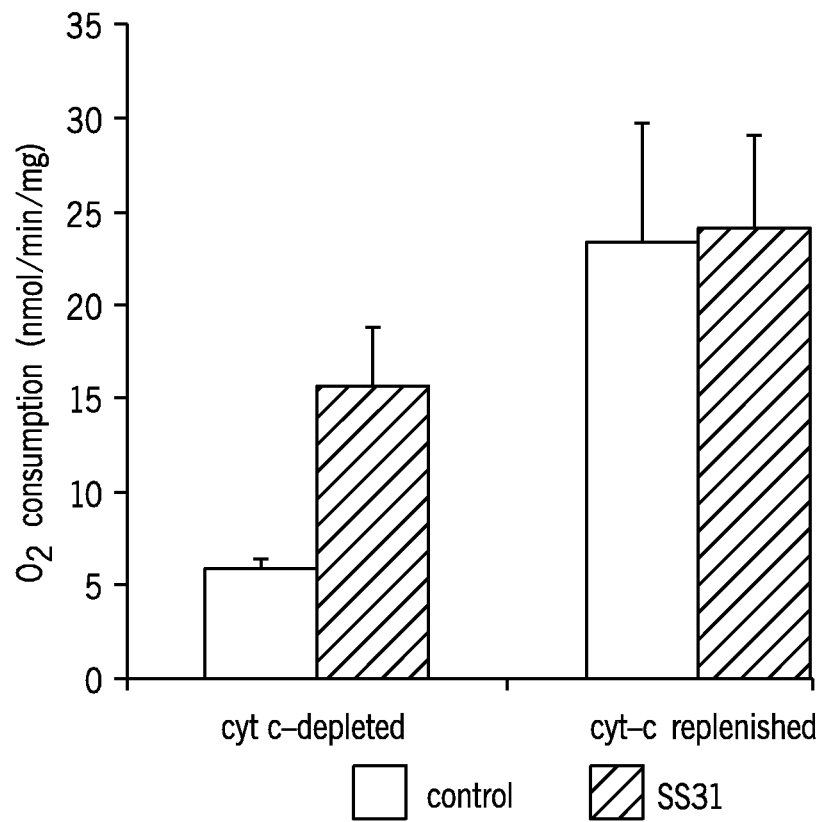
FIG. 7 is a chart showing that the peptide D-Arg-2',6'-Dmt-Lys-Phe-NH$_2$ (SS-31) enhances respiration in cytochrome c-depleted mitoplasts.

The Peptide D-Arg-2',6'-Dmt-Lys-Phe-NH$_2$ (SS-31) Enhances Respiration in Cytochrome c-Depleted Mitoplasts To demonstrate the role of cytochrome c in the action of SS-31 on mitochondrial respiration, the effect of SS-31 on mitochondrial O$_2$ consumption was determined in cytochrome c-depleted mitoplasts made from once-frozen rat kidney mitochondria (FIG. 7). Rates of respiration were measured in the presence of 500 µM Succinate with or without 100 µM SS-31. The experiment was carried out in triplicate, with n=3. These data suggest that: 1) SS-31 works via IMM-tightly bound cytochrome c; 2) SS-31 can rescue a decline in functional cytochrome c. Accordingly, aromatic-cationic peptides of the present disclosure are useful for the prevention or treatment of diseases or disorders characterized by dysregulation of cytochrome c.

Example 9

Figure 8:
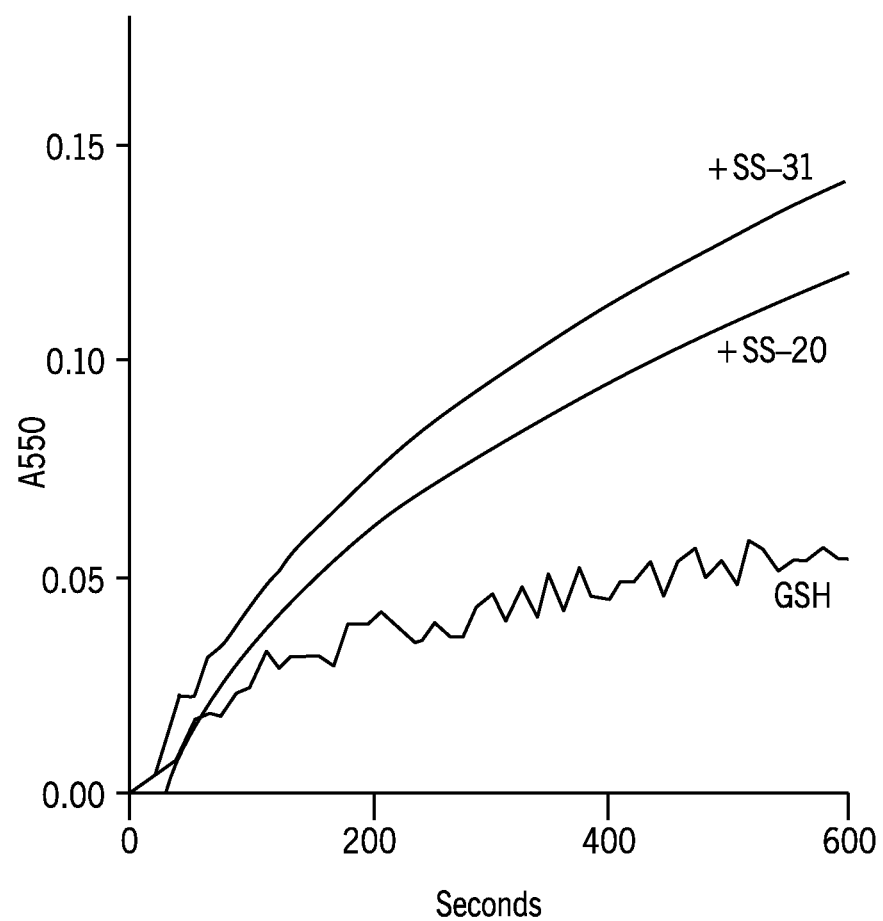
FIG. 8 is a chart showing that the peptides D-Arg-2',6'-Dmt-Lys-Phe-NH$_2$ (SS-31) and Phe-D-Arg-Phe-Lys-NH$_2$ (SS-20) facilitate cytochrome c reduction.

The Peptides D-Arg-2',6'-Dmt-Lys-Phe-NH$_2$ (SS-31) and Phe-D-Arg-Phe-Lys-NH$_2$ (SS-20) Facilitate Cytochrome c Reduction SS-31 and SS-20 can accelerate the kinetics of cytochrome c reduction induced by glutathione (GSH) as a reducing agent (FIG. 8). Reduction of cytochrome c was monitored by increase in absorbance at 550 nm. Addition of GSH resulted in a time-dependent increase in absorbance at 550 nm (FIG. 8). Similar results were obtained using N-acetylcysteine (NAC) as a reducing agent (not shown). The addition of SS-31 alone at 100 µM concentrations did not reduce cytochrome c, but SS-31 dose-dependently increased the rate of NAC-induced cytochrome c reduction, suggesting that SS-31 does not donate an electron, but can speed up electron transfer. Accordingly, aromatic-cationic peptides of the present disclosure are useful for the prevention or treatment of diseases or disorders characterized by dysregulation of cytochrome c and are useful for facilitating cytochrome c reduction.

Example 10

Figure 9:
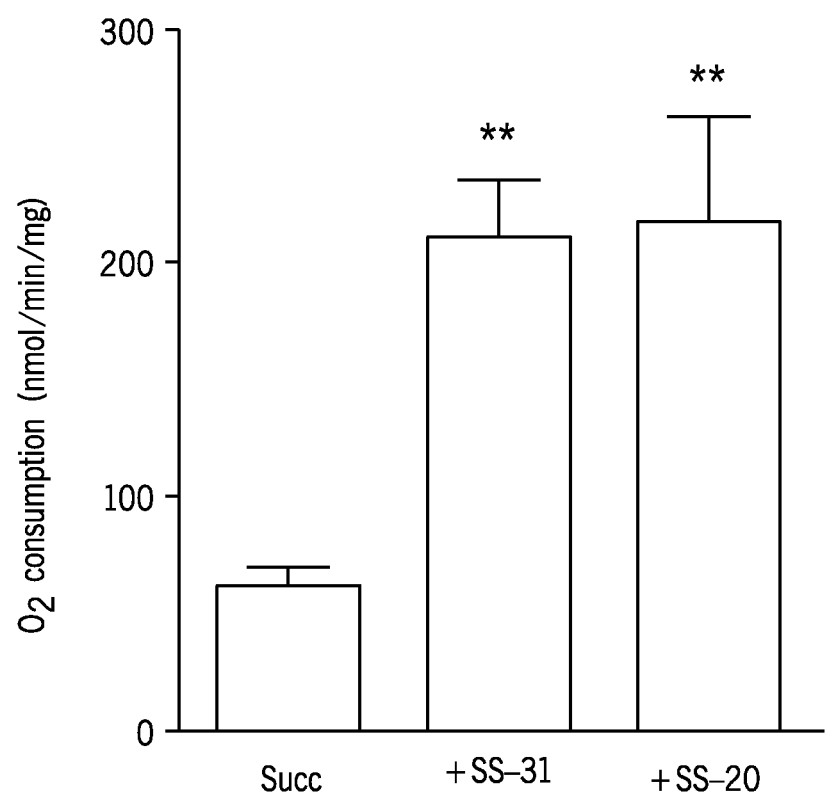
FIG. 9 is a chart showing that the peptides D-Arg-2',6'-Dmt-Lys-Phe-NH$_2$ (SS-31) and Phe-D-Arg-Phe-Lys-NH$_2$ (SS-20) promote electron flux, as measured by O$_2$ consumption in isolated rat kidney mitochondria.
Figure 10:
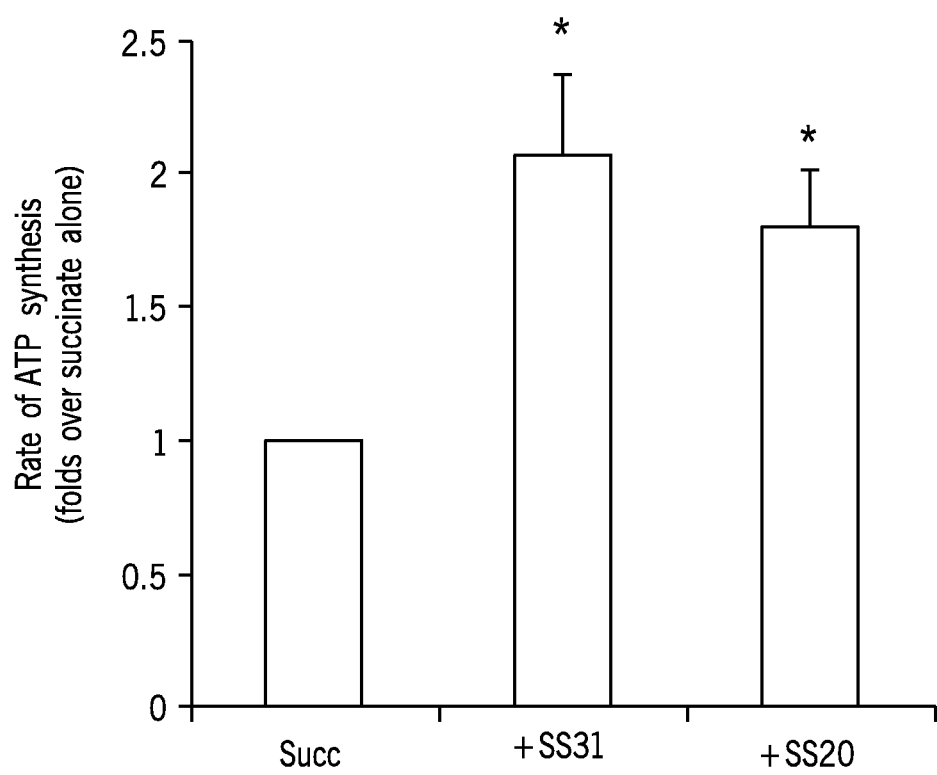
FIG. 10 is a chart showing that the peptides D-Arg-2',6'-Dmt-Lys-Phe-NH$_2$ (SS-31) and Phe-D-Arg-Phe-Lys-NH$_2$ (SS-20) increase the rate of ATP production in isolated mitochondria.

The peptides D-Arg-2',6'-Dmt-Lys-Phe-NH$_2$ (SS-31) and Phe-D-Arg-Phe-Lys-NH$_2$ (SS-20) Increase Mitochondrial Electron Flux and ATP Synthesis Both SS-20 and SS-31 can promote electron flux, as measured by O$_2$ consumption in isolated rat kidney mitochondria (FIG. 9). SS-20 or SS-31 was added at 100 µM concentrations to isolated mitochondria in respiration buffer containing 0.5 mM succinate (complex II substrate) and 400 µM ADP. Similar increases in O$_2$ consumption were observed when low concentrations of complex I substrates (glutamate/malate) were used (data not shown). The increase in electron flux was correlated with a significant increase in the rate of ATP production in isolated mitochondria energized with low concentrations of succinate (FIG. 10). Accordingly, targeting SS-20 and SS-31 to the IMM can facilitate electron flux in the electron transport chain and improve ATP synthesis, especially under conditions of reduced substrate supply.

Example 11

Cytochrome c Isolation and Purification

Methods to isolate and purify cytochrome c are known in the art. One exemplary, non-limiting method is provided. Cytochrome c has several positively charged groups, giving it a pI of around 10. Thus, it is normally bound to the membrane of mitochondria by ionic attraction to the negative charges of the phospholipids on the membrane. The tissue and mitochondria are first broken up by homogenization in a blender at low pH, in an aluminum sulfate solution. The positively charged aluminum ions can displace the cytochrome c from the membrane by binding to the negatively charged phospholipids and free the protein in solution. Excess aluminum sulfate is removed by raising the pH to 8.0, where the aluminum precipitates in the form of aluminum hydroxide.

After filtration to eliminate the precipitated aluminum hydroxide, ion-exchange chromatography is used to separate proteins as a function of their charge. Cytochrome c has several positively charged groups; typically, the column is made out of Amberlite CG-50, a negatively charged or cation-exchange resin.

Once the eluent has been collected, ammonium sulfate precipitation is used to selectively precipitate the remaining contaminant proteins in the cytochrome c preparation. Most proteins precipitate at 80% saturation in ammonium sulfate, whereas cytochrome c remains soluble. The excess of salts present in the solution are then removed by gel filtration chromatography which separates protein on the basis of their size.

To assess the purification, samples of the preparation are collected at each step of the purification. These samples are then assayed for total protein content using the Bradford method, and their cytochrome c concentration is measure by spectrophotometry.

Example 12

The Peptides 2',6'-Dmt-D-Arg-Phe-(atn)Dap-NH$_2$ (SS-19), 2',6'-Dmt-D-Arg-Phe-Lys-Ald-NH$_2$ (SS-37), and Dmt-D-Arg-Ald-Lys-NH$_2$ (SS-36) Interact with Hydrophobic Domain of Cardiolipin (CL)

The peptides 2',6'-Dmt-D-Arg-(atn)Dap-Lys-NH$_2$ (SS-19) and 2',6'-Dmt-D-Arg-Phe-Lys-Ald-NH$_2$ (SS-37) cationic peptides carry net positive charge at neutral pH. They are expected to associate with anionic phospholipid cardiolipin based on electrostatic interaction. The interaction of small peptides with lipid membranes can been studied using fluorescence spectroscopy (Surewicz and Epand, 1984). The fluorescence of intrinsic Trp residues exhibits increased quantal yield upon binding to phospholipid vesicles, and this was also accompanied by a blue shift of the maximum emission indicative of the incorporation of the Trp residue in a more hydrophobic environment. Polarity-sensitive fluorescent probes were incorporated into the peptides and fluorescence spectroscopy was used to determine if SS-19, SS-37 and SS-36 interact with CL. Results are shown in FIG. 11.

Figure 11A:
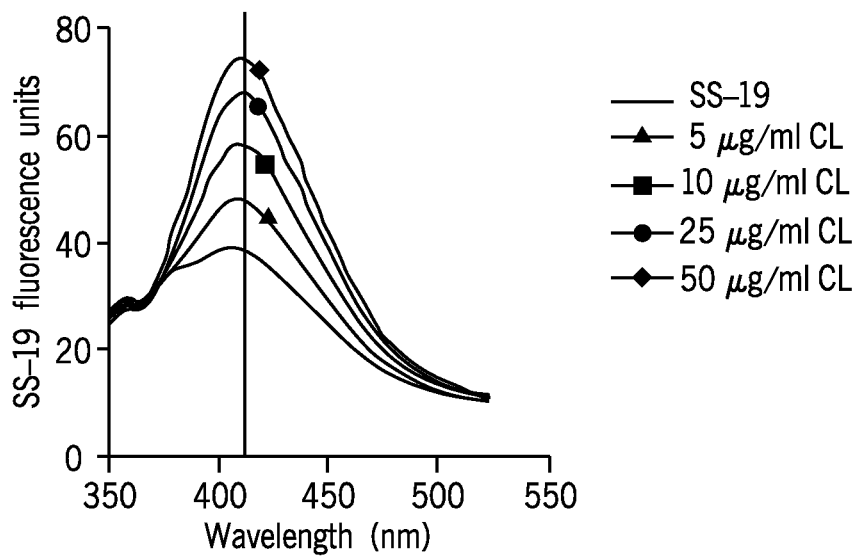
FIG. 11A-11C are charts showing interaction of the peptides 2',6'-Dmt-D-Arg-Phe-(atn)Dap-NH$_2$ (SS-19) (FIG. 11A), 2',6'-Dmt-D-Arg-Ald-Lys-NH$_2$ (SS-36) (FIG. 11C) and 2',6'-Dmt-D-Arg-Phe-Lys-Ald-NH$_2$ (SS-37) (FIG. 11B) with cardiolipin.

The peptide 2',6'-Dmt-D-Arg-Phe-(atn)Dap-NH$_2$ (SS-19) contains anthraniloyl incorporated into diaminopropionic acid. Anthraniloyl derivatives fluoresce in the 410-420 nm range when excited at 320-330 nm (Hiratsuka T, 1983). The quantum yield of anthraniloyl derivatives is strongly dependent on the local environment, and can increase 5-fold going from water to 80% ethanol, together with a blue shift in the emission maxima (λ max) of <10 nm (Hiratsuka T, 1983). Fluorescence emission spectrum of SS-19 (1 µM) alone, and in the presence of increasing concentrations of CL (5 to 50 µg/ml), was monitored following excitation at 320 nm using Hitachi F-4500 fluorescence spectrophotometer. Addition of CL (5-50 µg/ml) led to 2-fold increase in quantal yield of SS-19 with no significant shift in λmax (FIG. 11A). These findings suggest that SS-19 interacts with the hydrophobic domain of CL.

Figure 11B:
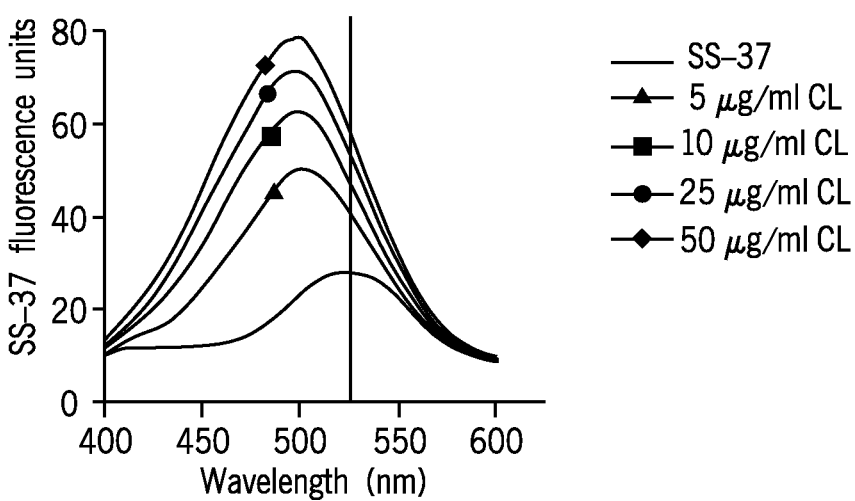

The peptide 2',6'-Dmt-D-Arg-Phe-Lys-Ald-NH$_2$ (SS-37) contains an additional amino acid, aladan (Ald), which has been reported to be particularly sensitive to the polarity of its environment and it has been used to probe the electrostatic character of proteins (Cohen et al., 2002). When excited at 350 nm, λmax shifts from 542 nm in water to 409 nm in heptane, accompanied by a significant increase in quantal yield (Cohen et al., 2001). Fluorescence emission spectrum of SS-37 (1 µM) alone, and in the presence of increasing concentrations of CL, was monitored following excitation at 350 nm. Addition of CL (5 to 50 µg/ml) led to a 3-fold increase in quantal yield of SS-37 as well as a clear blue shift in λ max, from 525 nm without CL to 500 nm with 50 µg/ml CL (FIG. 11B). These results provide evidence that SS-37 interact with hydrophobic domain of CL.

Figure 11C:
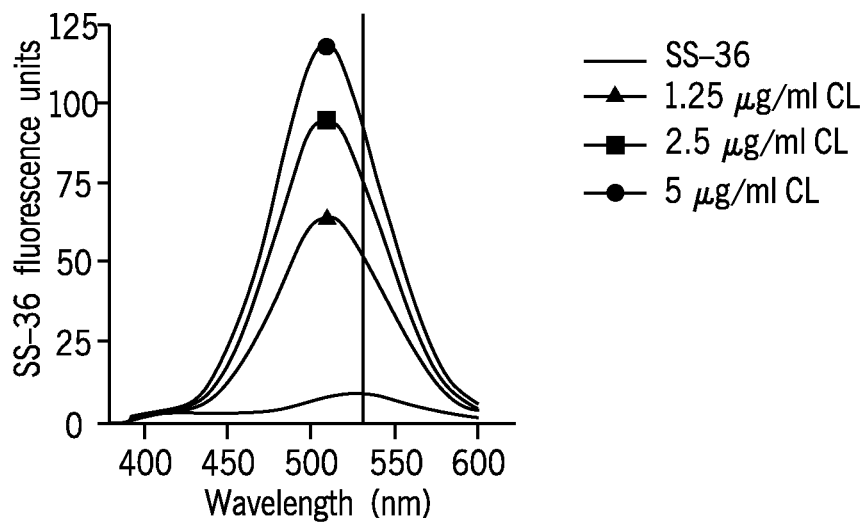

The peptide 2',6'-Dmt-D-Arg-Ald-Lys-NH$_2$ (SS-36) contains Ald in place Phe$^3$ in SS-02. Fluorescence emission spectrum of SS-36 (1 µM) alone, and in the presence of increasing concentrations of CL, was monitored following excitation at 350 nm. SS-36 was the most sensitive to the addition of CL, with dramatic increase in quantal yield and blue shift observed with much lower added amounts of CL (1.25 to 5 µg/ml). The λmax shifted from 525 nm without CL to 500 nm with as little as 1.25 µg/ml CL, and quantal yield increased by more than 100-fold with the addition of 5 µg/ml of CL (FIG. 11C). These results provide evidence that SS-36 interacts strongly with the hydrophobic domain of CL. Accordingly, aromatic-cationic peptides of the present disclosure are useful for the prevention or treatment of diseases or disorders characterized by dysregulation of cardiolipin.

Example 13

Interaction of the Peptide 2',6'-Dmt-D-Arg-Phe-(Atn)Dap-NH$_2$ (SS-19) with Cytochrome c Fluorescence quenching was used to demonstrate the interaction of the peptide Dmt-D-Arg-Phe-(atn)Dap-NH$_2$ (SS-19) with cytochrome c. Maximal fluorescence emission of SS-19 was monitored at 420 nm following excitation at 320 nm using Hitachi F-4500 fluorescence spectrophotometer. Results are shown in FIG. 12.

Figure 12A:
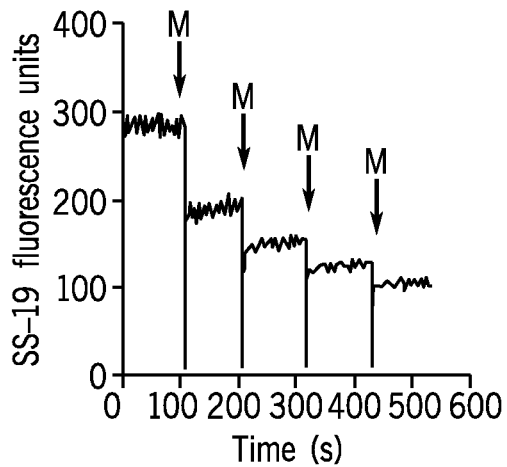
FIG. 12A-12D are charts showing interaction of the peptides 2',6'-Dmt-D-Arg-Phe-(atn)Dap-NH$_2$ (SS-19) with cytochrome c.
Figure 12B:
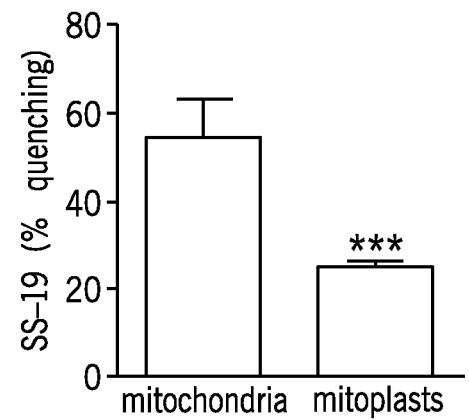
Figure 12C:
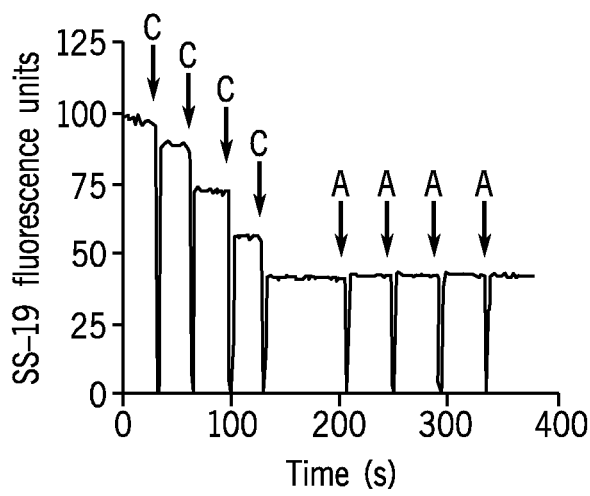
Figure 12D:
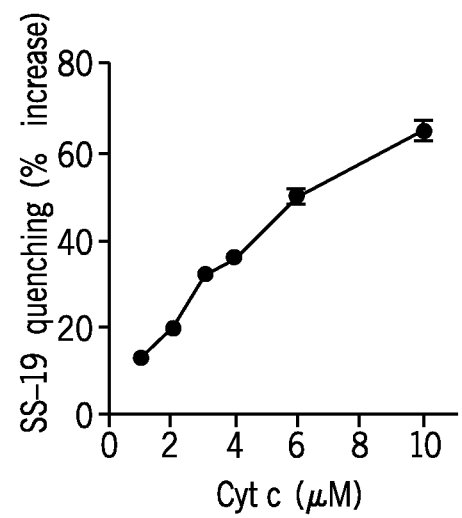

SS-19 fluorescence (10 µM) was quenched by sequential addition of 0.2 mg isolated rat renal kidney mitochondria (FIG. 12A, M+arrows), suggesting uptake of SS-19 by mitochondria. Quenching of SS-19 was significantly reduced when cytochrome c-depleted mitoplasts (0.4 mg) were added, suggesting that cytochrome c plays a major role in the quenching of SS-19 by mitochondria (FIG. 12B). SS-19 fluorescence (10 µM) was similarly quenched by sequential addition of 2 µM cytochrome c (FIG. 12C, C+arrows). The quenching by cytochrome c was not displaced by sequential additions of bovine serum albumin (FIG. 12C, A+arrows) (500 µg/ml). These data indicate that SS-19 is likely to interact very deep in the interior of cytochrome c in the heme environment. The interaction of SS-19 with cytochrome c is linearly dependent on the amount of cytochrome c added (FIG. 12D). Accordingly, aromatic-cationic peptides of the present disclosure are useful for the prevention or treatment of diseases or disorders characterized by dysregulation of cytochrome c.

Example 14

The Peptides 2',6'-Dmt-D-Arg-Phe-(atn)Dap-NH$_2$ (SS-19), 2',6'-Dmt-D-Arg-Phe-Lys-Ald-NH$_2$ (SS-37) and 2',6'-Dmt-D-Arg-Ald-Lys-NH$_2$ (SS-36) Interact with Cytochrome c and CL Fluorescence spectroscopy was used to demonstrate the interaction of the peptides 2',6'-Dmt-D-Arg-Phe-(atn)Dap-NH$_2$ (SS-19), 2',6'-Dmt-D-Arg-Phe-Lys-Ald-NH$_2$ (SS-37), and 2',6'-Dmt-D-Arg-Ald-Lys-NH$_2$ (SS-36) interact with cytochrome c in the presence of CL. Results are shown in FIG. 13

Figure 13A:
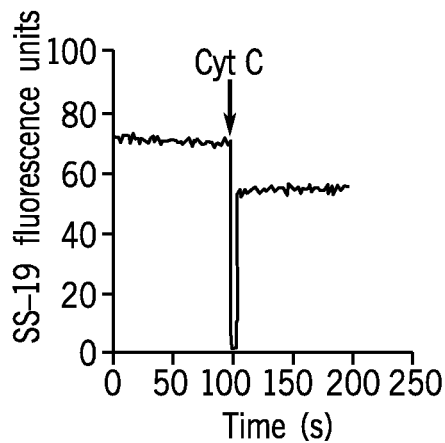
FIG. 13A-13D are charts showing interaction of the peptides 2',6'-Dmt-D-Arg-Phe-(atn)Dap-NH$_2$ (SS-19) (FIG. 13A, 13B), 2',6'-Dmt-D-Arg-Phe-Lys-Ald-NH$_2$ (SS-37) (FIG. 13C), and 2',6'-Dmt-D-Arg-Ald-Lys-NH$_2$ (SS-36) (FIG. 13D) with cytochrome c and cardiolipin (CL).

Fluorescence emission of SS-19 (10 µM) was monitored in real time (Ex/Em=320 nm/420 nm) using Hitachi F-4500 fluorescence spectrophotometer. Addition of cytochrome c (2 µM) led to immediate quenching of the fluorescence signal (FIG. 13A)

Figure 13B:
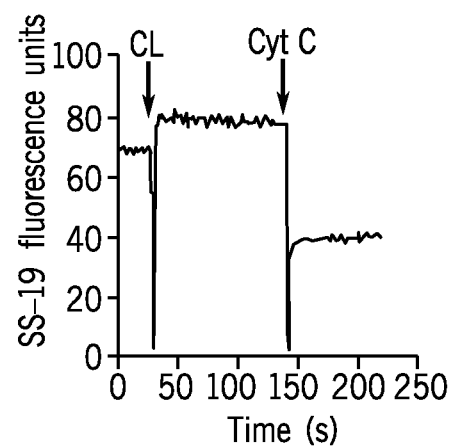

Fluorescence emission of SS-19 (10 µM) was monitored in real time (Ex/Em=320 nm/420 nm) using Hitachi F-4500 fluorescence spectrophotometer. Addition of CL (50 µg/ml) led to increase in SS-19 fluorescence. Subsequent addition of cytochrome c (2 µM) led to larger extent of quenching of SS-19 fluorescence compared to addition of cytochrome c without CL (FIG. 13B). These data indicate that the interaction of SS-19 with cytochrome c is enhanced in the presence of CL. CL may potentiate the interaction between SS-19 and cytochrome c by serving as an anionic platform for the two cationic molecules.

Figure 13C:
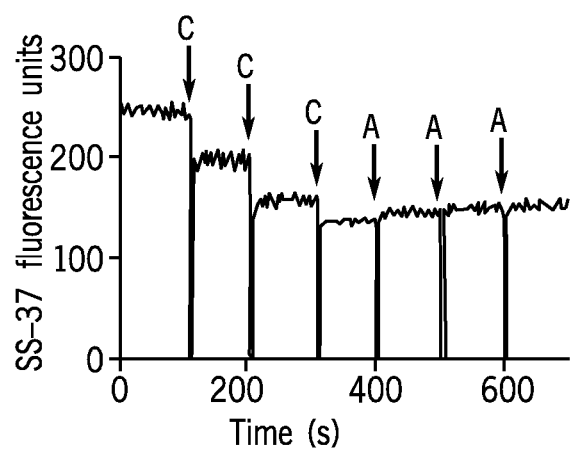

SS-37 fluorescence (10 µM) was similarly quenched by sequential addition of 2 µM cytochrome c in the presence of CL (50 µg/ml) (FIG. 13C, C+arrows). The quenching by cytochrome c was not displaced by sequential additions of bovine serum albumin (500 µg/ml) (FIG. 13C, A+arrows). Thus interaction of these peptides with CL does not interfere with their ability to interact very deep in the interior of cytochrome c.

Figure 13D:
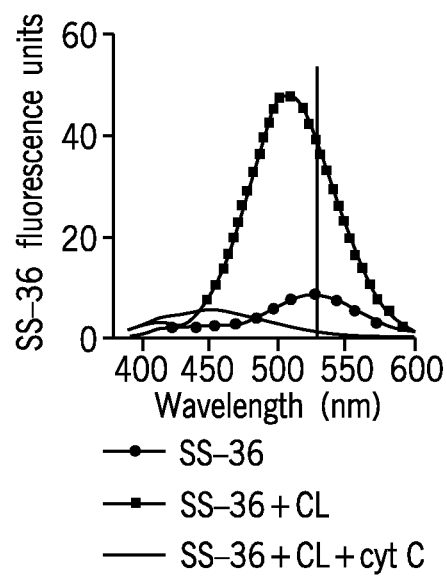

SS-36 also contains the polarity-sensitive fluorescent amino acid aladan. Addition of CL (2.5 µg/ml) led to increase in SS-36 fluorescence (FIG. 13D). After subsequent addition of cytochrome c(2 µM) the emission spectrum of SS-36 shows dramatic quenching of peptide's fluorescence with large blue shift of the emission maxima (510 nm to 450 nm) (FIG. 13D). These data suggest that the peptide is interacting with a hydrophobic domain deep in the interior of cytochrome c-CL complex. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction.

Example 15

The peptides 2',6'-Dmt-D-Arg-Phe-(atn)Dap-NH$_2$ (SS-19), Phe-D-Arg-Phe-Lys-NH$_2$ (SS-20), D-Arg-2',6'-Dmt-Lys-Phe-NH$_2$ (SS-31), 2',6'-Dmt-D-Arg-Ald-Lys-NH$_2$ (SS-36) and D-Arg-Tyr-Lys-Phe-NH$_2$ (SPI-231) Protect the Heme Environment of Cytochrome c from the Acyl Chain of CL Circular dichroism (CD) was carried out to examine the effects of the peptides on protecting the heme environment of cytochrome c from the acyl chain of CL. For heme proteins, the Soret CD spectrum is strictly correlated with the heme pocket conformation. In particular, the negative 416-420 nm Cotton effect is considered diagnostic of Fe(III)-Met80 coordination in native cytochrome c (Santucci and Ascoli, 1997). Loss of the Cotton effect reveals alterations of the heme pocket region which involve the displacement of Met80 from the axial coordination to the heme iron. CD spectra were obtained using AVIV CD Spectrometer Model 410. Results are shown in FIG. 14.

Changes in the Soret CD spectrum of cytochrome c (10 µM) were recorded in the absence (dotted line) and presence (dashed line) of 30 µg/ml CL, plus addition of different peptides (10 µM) (solid line) (FIG. 14). CD measurements were carried out using 20 mM HEPES, pH 7.5, at 25° C. and expressed as molar ellipticity (Δ) (m Deg). The addition of CL resulted in the disappearance of the negative Cotton effect, and this was completely prevented by the addition of these peptides. These results provide clear evidence that the peptides interact with the heme pocket of cytochrome c and protect the Fe-Met80 coordination. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction. In addition, aromatic-cationic peptides of the present disclosure are useful to protect the heme environment of cytochrome c from the acyl chain of cardiolipin.

Example 16

The peptides D-Arg-2',6'-Dmt-Lys-Phe-NH$_2$ (SS-31), Phe-D-Arg-Phe-Lys-NH$_2$ (SS-20), and D-Arg-Tyr-Lys-Phe-NH$_2$ (SPI-231) Prevent the Inhibition of Cytochrome c Reduction Caused by CL Cytochrome c is a carrier of electrons between respiratory complex III and IV in mitochondria. Cytochrome c is reduced ($Fe^{2+}$) after it accepts an electron from cytochrome c reductase, and it is then oxidized to $Fe^{3+}$ by cytochrome c oxidase. The CL associated cytochrome c has a redox potential which is significantly more negative than native cytochrome c, and the reduction of cytochrome c is significantly inhibited in the presence of CL (Basova et al., 2007).

Figure 15A:
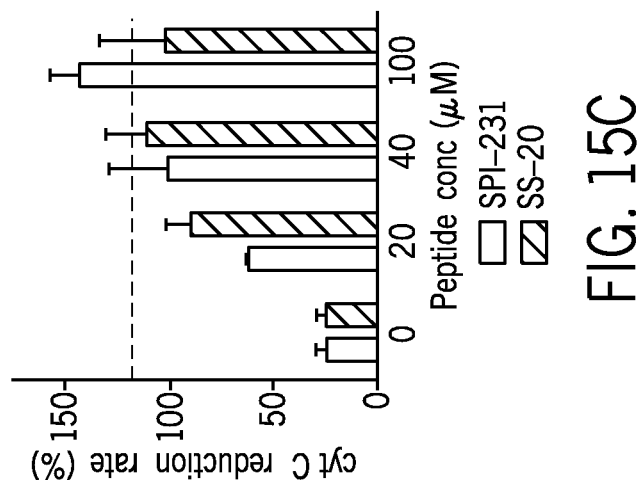
FIG. 15A-15C are charts showing the peptide D-Arg-2',6'-Dmt-Lys-Phe-NH$_2$ (SS-31) (FIG. 15A, 15B), Phe-D-Arg-Phe-Lys-NH$_2$ (SS-20) (FIG. 15C), D-Arg-Tyr-Lys-Phe-NH$_2$ (SPI-231) (FIG. 15C) preventing the inhibition of cytochrome c reduction caused by cardiolipin.

Reduction of cytochrome c (20 µM) was induced by the addition of glutathione (500 µM) in the absence or presence of CL (100 µg/ml) (FIG. 15A). Reduction of cytochrome c was monitored by absorbance at 550 nm using a 96-well UV-VIS plate reader (Molecular Devices). Addition of CL decreased the rate of cytochrome c reduction by half. Addition of SS-31 (20, 40 or 100 µM) dose-dependently prevented the inhibitory action of CL (FIG. 15A).

Figure 15B:
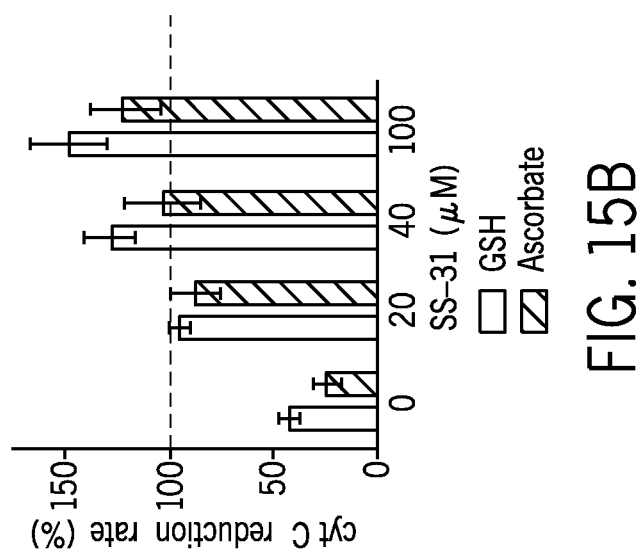
Figure 15C:
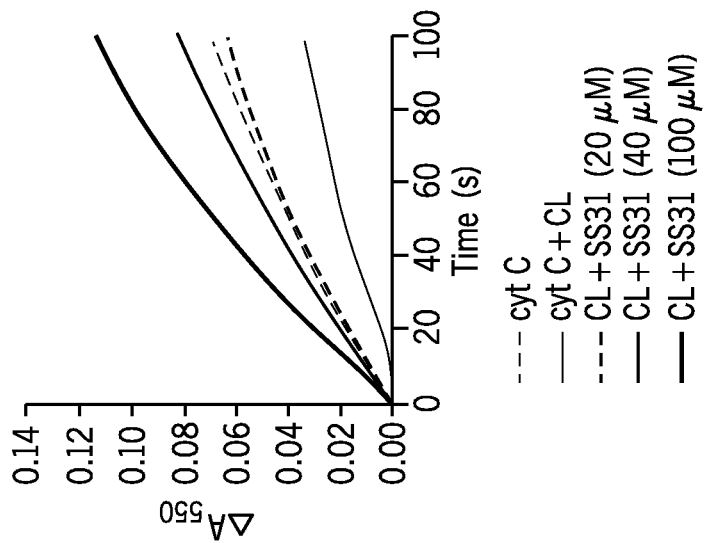

SS-31 dose-dependently overcame the inhibitory effect of CL on kinetics of cytochrome c reduction induced by 500 µM GSH or 50 µM ascorbate (FIG. 15B). SS-20 and SP-231 also prevented CL inhibition of cytochrome c reduction elicited by 500 µM GSH (FIG. 15C). Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction. In addition, aromatic-cationic peptides of the present disclosure are useful to prevent the inhibition of cytochrome c reduction caused by cardiolipin.

Example 17

The Peptides D-Arg-2',6'-Dmt-Lys-Phe-NH$_2$ (SS-31) and Phe-D-Arg-Phe-Lys-NH$_2$ (SS-20) Enhances O$_2$ Consumption in Isolated Mitochondria Both SS-20 and SS-31 can promote electron flux, as measured by O$_2$ consumption in isolated rat kidney mitochondria. SS-20 or SS-31 was added at 10 µM or 100 µM concentrations to isolated mitochondria in respiration buffer containing glutamate/malate (complex I substrate), 0.5 mM succinate (complex II substrate) or 3 µM TMPD/1 mM ascorbate (direct reductant of cytochrome c). 400 µM ADP was added to initiate State 3 respiration. Results are shown in FIG. 16.

Figure 16A:
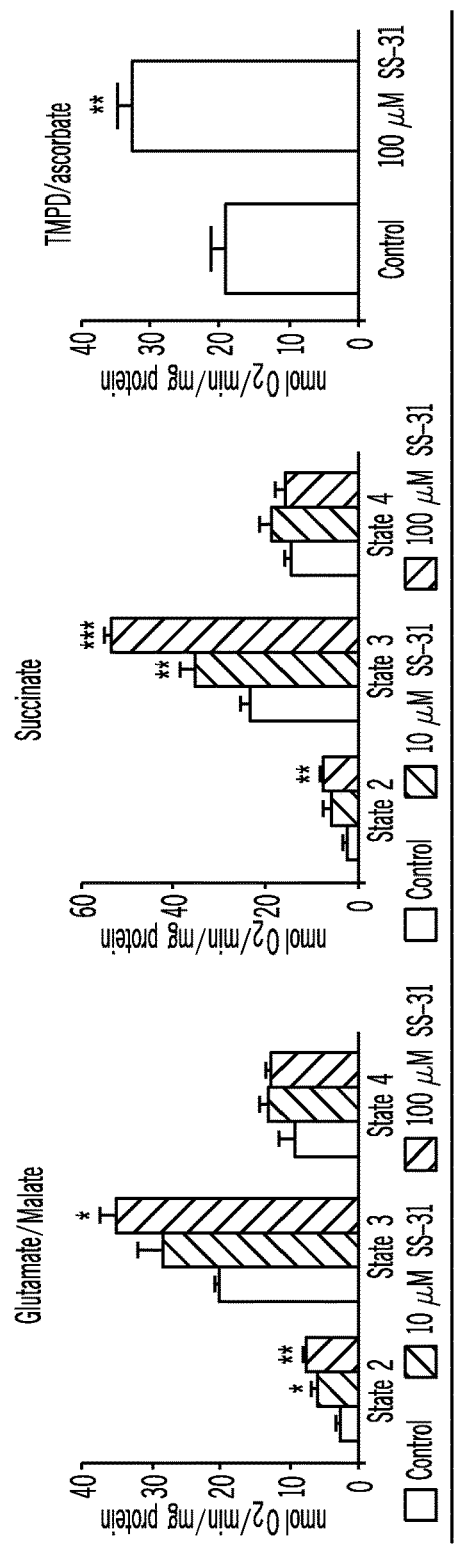
FIG. 16A-16B are charts showing the peptides D-Arg-2',6'-Dmt-Lys-Phe-NH$_2$ (SS-31) (FIG. 16A) and Phe-D-Arg-Phe-Lys-NH$_2$ (SS-20) (FIG. 16B) enhancing O$_2$ consumption in isolated mitochondria.
Figure 16B:
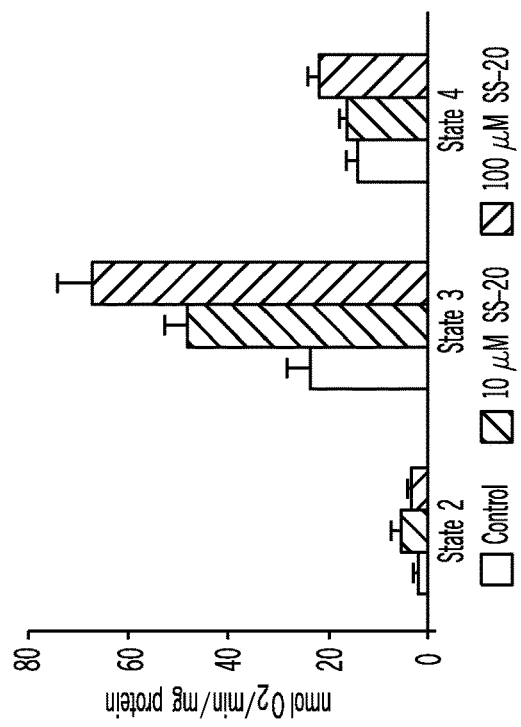

SS-31 increased O$_2$ consumption in state 3 respiration with either complex I or complex II substrates, or when cytochrome c is directly reduced by TMPD/ascorbate (FIG. 16A). SS-20 also increases O$_2$ consumption in state 3 respiration when these substrates were used (FIG. 16B; data with glutamate/malate and TMPD/ascorbate not shown).

These data suggest that SS-31 increases electron flux in the electron transport chain, and that the site of action is between cytochrome c and complex IV (cytochrome c oxidase). Accordingly, aromatic-cationic peptides of the present disclosure, useful for promoting electron transfer to oxygen without uncoupling mitochondria, increasing O$_2$ consumption, and treating diseases or conditions related to dysregulation of O$_2$ consumption in mitochondria.

Example 18

Figure 17:
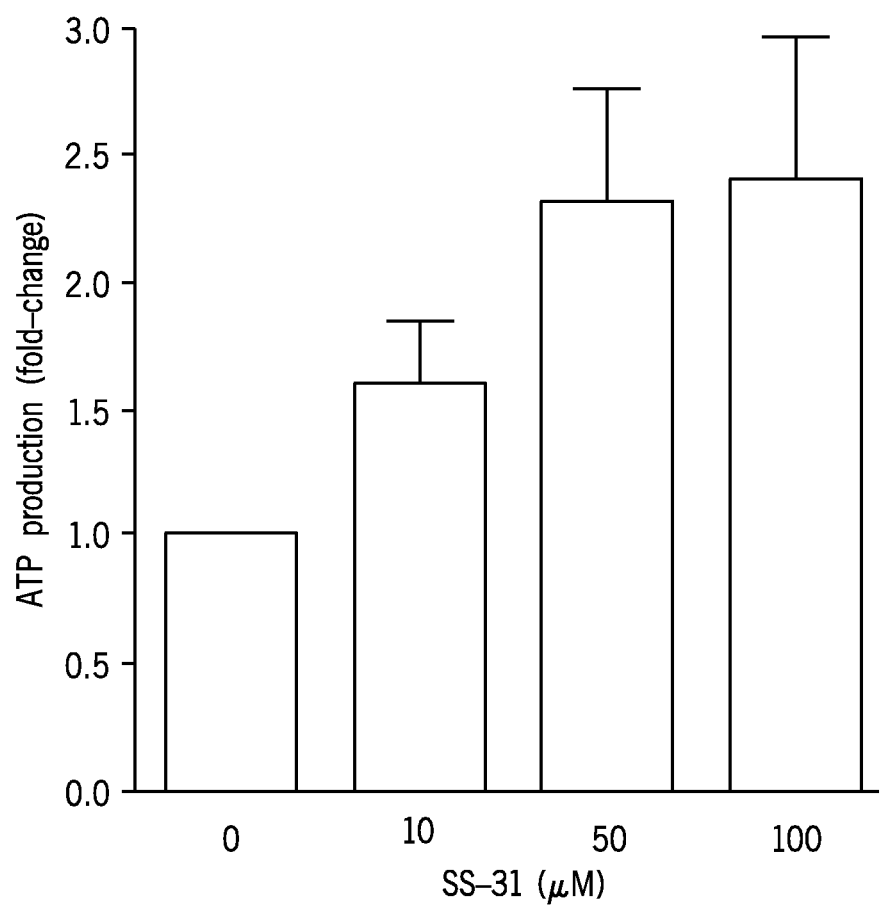
FIG. 17 is a chart showing the peptide D-Arg-2',6'-Dmt-Lys-Phe-NH$_2$ (SS-31) increases ATP synthesis in isolated mitochondria.

The peptide D-Arg-2',6'-Dmt-Lys-Phe-NH$_2$ (SS-31) Increases ATP Synthesis in Isolated Mitochondria Increase in electron flux in the electron transport chain can either result in increase in ATP synthesis or increase in electron leak and generation of free radicals. ATP synthesis in isolated mitochondria was assayed by HPLC. SS-31 dose-dependently increased ATP synthesis, suggesting that the increase in electron flux is coupled to oxidative phosphorylation (FIG. 17). Accordingly, aromatic-cationic peptides of the present disclosure are useful for increasing ATP synthesis in mitochondria and for treating diseases or disorder characterized by dysregulation of ATP synthesis.

Example 19

Figure 18:
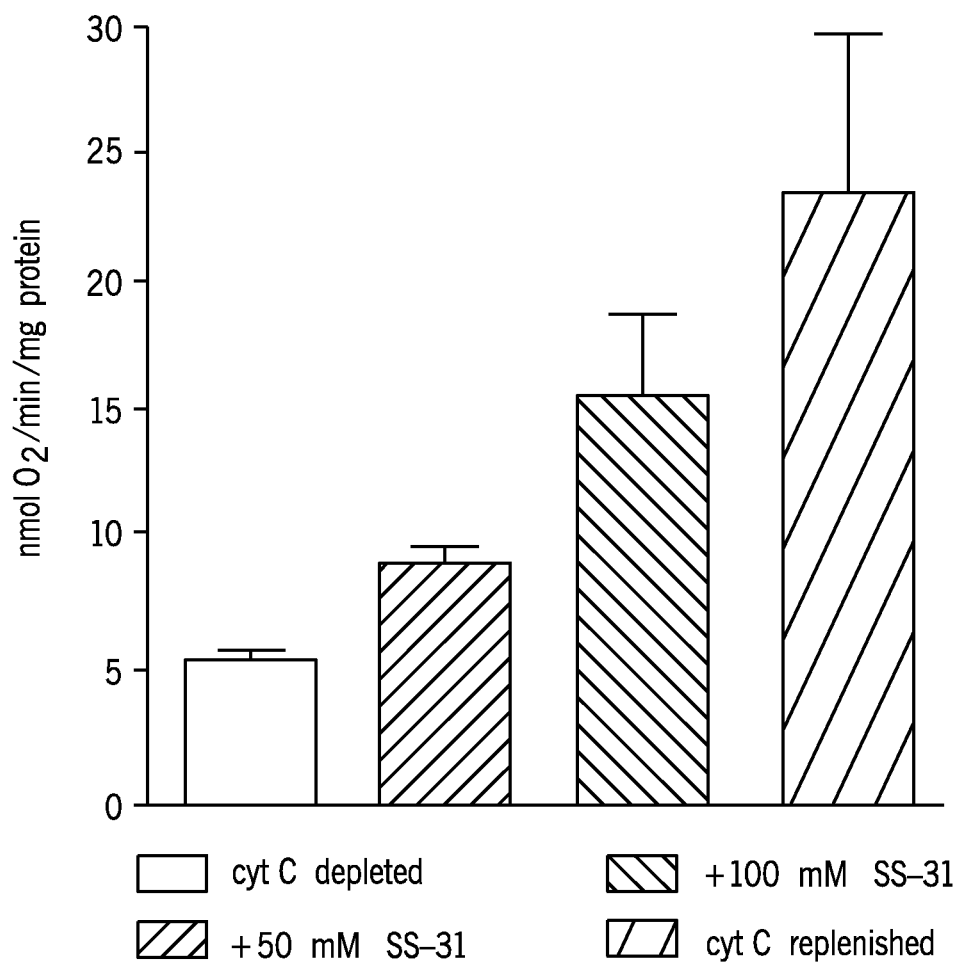
FIG. 18 is a chart showing the peptide D-Arg-2',6'-Dmt-Lys-Phe-NH$_2$ (SS-31) enhances respiration in cytochrome c-depleted mitoplasts.

The Peptide D-Arg-2',6'-Dmt-Lys-Phe-NH$_2$ (SS-31) Enhances Respiration in Cytochrome c-Depleted Mitoplasts A model of cytochrome c tightly bound to mitochondrial cardiolipin was used to investigate interaction of SS-31 with cytochrome c-CL complex in mitochondria. After removal of outer membrane with digitonin, mitoplasts were washed with 120 mM KCl to remove all free and electrostatically associated cytochrome c, leaving only cytochrome c tightly bound to CL. D-Arg-Dmt-Lys-Phe-NH$_2$ (SS-31) enhances complex II respiration in mitoplasts with cytochrome c tightly bound to inner mitochondrial membrane in a dose-dependent manner (FIG. 18). These data suggests that SS-31 directly interacts with cytochrome c—CL complex and promotes electron transfer from complex III to complex IV.

Example 20

The Peptide D-Arg-2',6'-Dmt-Lys-Phe-NH$_2$ (SS-31) Prevents CL from Switching Cytochrome c from an Electron Carrier into a Peroxidase Activity The six coordination of the heme in cytochrome c prevents direct interaction of H$_2$O$_2$ with the catalytic metal site, and native cytochrome c in solution is a poor peroxidase. Upon interaction with CL, cytochrome c undergoes a structural change with rupture of the Fe-Met80 coordination. This results in the exposure of the heme $Fe^{3+}$ to H$_2$O$_2$, and peroxidase activity increases dramatically (Vladimirov et al., 2006; Sinibaldi et al., 2008). The mechanism of action of cytochrome c peroxidase is similar to that of other peroxidases, such as horse radish peroxidase (HRP). Thus it is possible to use the amplex red-HRP reaction to investigate cytochrome c peroxidase activity. In the presence of peroxidase, amplex red (AR) reacts with H$_2$O$_2$ to form the red-fluorescent oxidation product, resorufin (Ex/Em=571/585).

Cytochrome c (2 µM) was mixed with CL (25 µg/ml) and 10 µM H$_2$O$_2$ in 20 mM HEPES, pH 7.4. Amplex red (50 µM) was then added and fluorescence emission monitored in real time using Hitachi F4500 fluorescence spectrophotometer. Addition of amplex red elicited rapid increase in fluorescence signal due to resorufin formation, providing direct evidence for peroxidase activity of cytochrome c/CL complex (FIG. 19A). Inclusion of SS-31 decreased the rate of amplex red peroxidation, suggesting that SS-31 interacts directly with cytochrome c to prevent CL-induced peroxidase activity (FIG. 19A).

Addition of SS-31 dose-dependently reduced the kinetics of cytochrome c peroxidase activity (FIG. 19B) but had no effect on HRP activity (data not shown). FIG. 19C shows a comparison of various peptides on their ability to inhibit cytochrome c peroxidase activity at a fixed concentration of 10 μM. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction. In addition, aromatic-cationic peptides of the present disclosure are useful for inhibiting peroxidase activity in cytochrome c.

Example 21

Figure 20A:
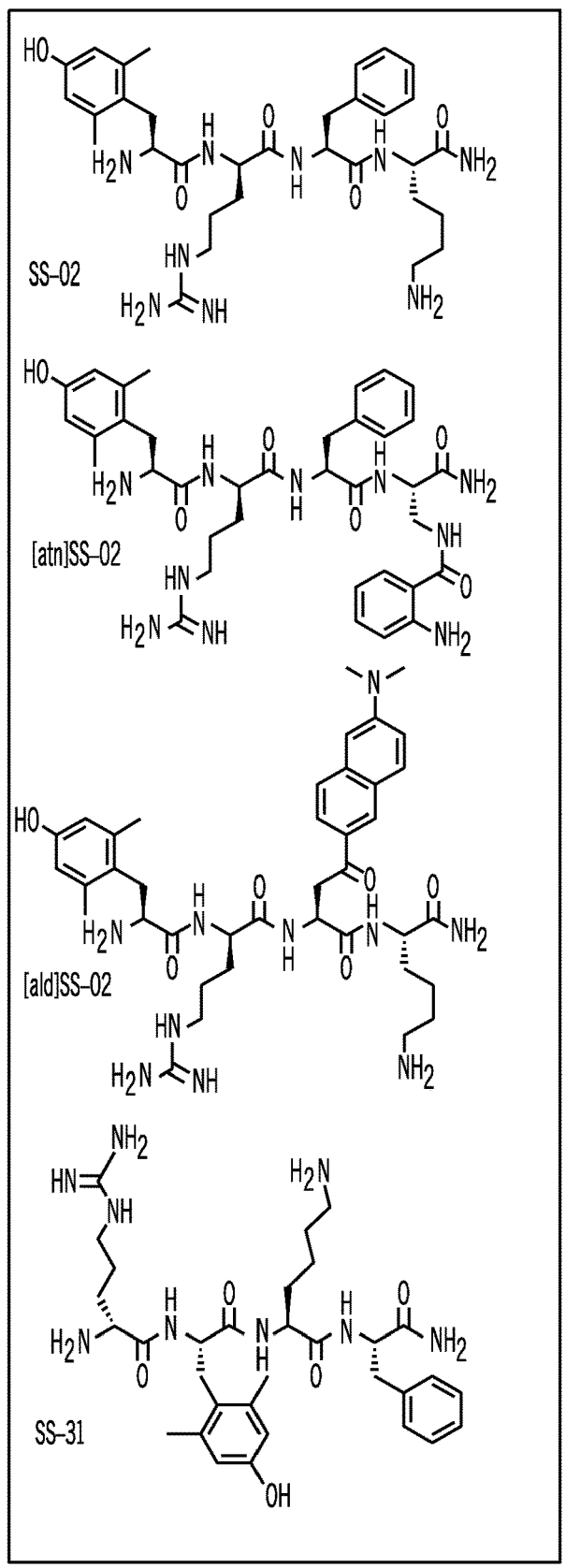
FIG. 20A is an illustration of the structures of the peptide analogs SS-02, [atn]SS-02 (also referred to as SS-19), [ald]SS-02 (also referred to as SS-36), and SS-31.

The Peptide Analog SS-02 Interacts with Cardiolipin and Liposomes that Contain Cardiolipin Fluorophore-labeled SS-02 was used to investigate the interaction of SS-02 with the phospholipid cardiolipin, as well as other phospholipids. The fluorophores β-anthraniloyl (atn; $\lambda ex=320$ nm) and aladan (ald; $\lambda ex=360$ nm) were incorporated within the peptide structure of SS-02, as shown in FIG. 20A. The resulting peptides are termed "[atn]SS-02" or "SS-19" and "[ald]SS-02" or "SS-36," respectively. The structure of SS-31 is also shown for comparison. Each of the fluorophores are known to show enhanced fluorescence emission in hydrophobic environment. In addition, ald is a dielectric-sensitive probe that produces progressive blue shift in its emission maxima ($\lambda$max) as the polarity of its environment decreases. Both the atn and ald fluorophores are also very small so they do not substantially alter the physicochemical properties of the tetrapeptide (P. W. Schiller et al., 2005, J Pept Res 65, 556-563).

Materials and Methods 1-palmitoyl-2-oleoyl-sn-glycero-3-phosphocholine (POPC), 1-palmitoyl-2-oleoyl-sn-glycero-3-phosphate (POPA), 1-palmitoyl-2-oleoyl-sn-glycero-3-phospho-L-serine (POPS), 1-palmitoyl-2-oleoyl-sn-glycero-3-phosphoethanolamine (PE), and 1,2-dipalmitoyl-sn-glycero-3-phospho-(1'-rac-glycerol) (DPPG) were obtained from Avanti Polar Lipids Inc (Alabaster, Ala.).

Liposomes were prepared using individual phospholipids POPC and cardiolipin (CL) mixed in a 1:1 ratio and dried under nitrogen. The lipids were then mixed in 20 mM Hepes (pH 7.4) by vortexing, and then sonicated five times for 30 seconds on ice using an ultrasonic probe tip sonicator (Cole-Palmer Ultrasonic Homogenizer, 20 kHz, Cole-Parmer Instrument Company, Vernon Hills, Ill.). Liposomes were used immediately after preparation.

Changes in the emission intensity of the [atn]SS-02 and the [ald]SS-02 were measured using a Hitachi F-4500 fluorescence spectrophotometer. The different solvents used to dissolve the various phospholipids (chloroform, methanol and ethanol) had negligible effect on the fluorescence spectrum of [atn]SS-02 and [ald]SS-02. All experiments were done in low ionic solution (deionized water) to optimize electrostatic interactions of peptides with phospholipids.

Results

Figure 20C:
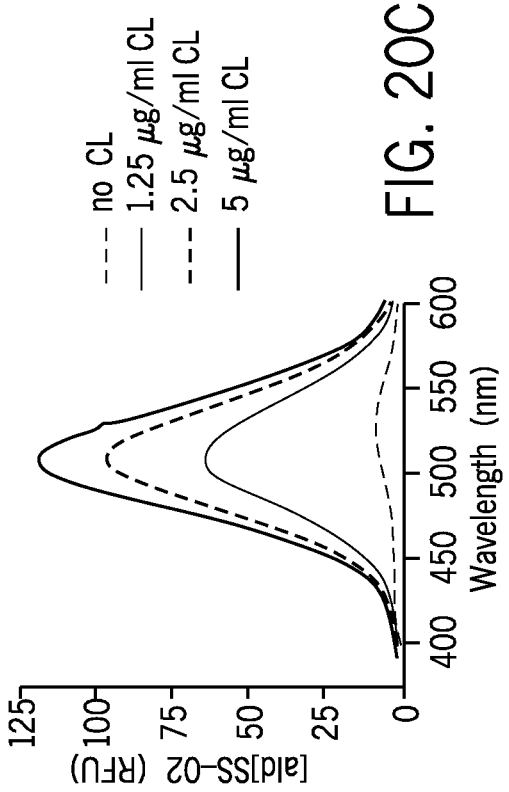
FIG. 20C shows representative emission spectra of different concentrations of cardiolipin added to 1 μM [ald]SS-02.
Figure 20E:
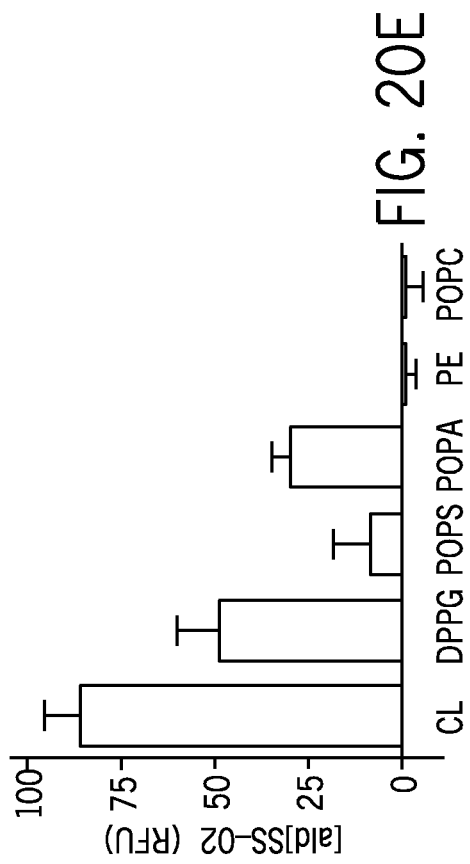
FIG. 20E is a bar graph showing the relative fluorescence of [ald]SS-02 added to cardiolipin (CL), DPPG, POPS, POPA, PE, and POPC.
Figure 20B:
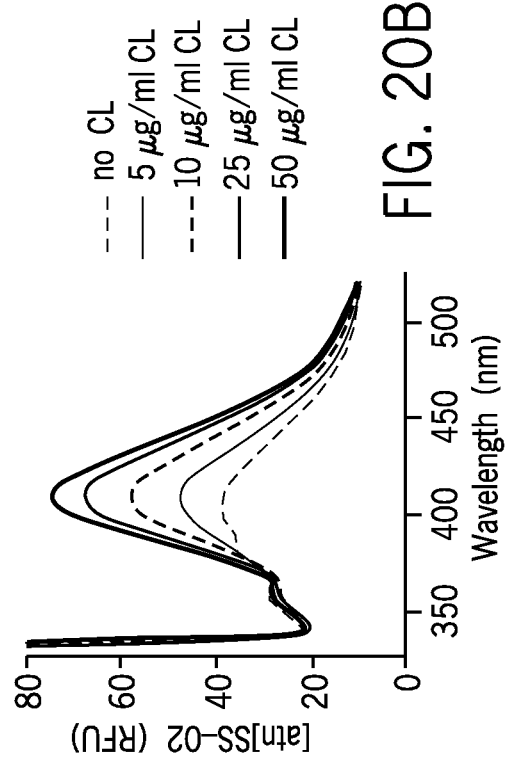
FIG. 20B shows representative emission spectra of different concentrations of cardiolipin added to 1 μM [atn]SS-02.

Increasing concentrations of cardiolipin (5, 10, 25, and 50 μg/mL) were added to 1 μM [atn]SS-02, and the emission intensity between 350 nm and 500 nm was measured. The addition of cardiolipin increased the emission intensity of [atn]SS-02 in a concentration-dependent manner (FIGS. 20B and 20G), suggesting interaction of this peptide with the hydrophobic environment of cardiolipin. Addition of increasing concentrations of cardiolipin (1.25, 2.5, and 5 μg/mL) to 1 μM [ald]SS-02 showed and even more pronounced concentration-dependent effect (FIG. 20C). In addition, cardiolipin produced a blue shift in the $\lambda$max of aladan from 540 nm to 510 nm, further indicating that this compound is localized in an hydrophobic environment.

Figure 20D:
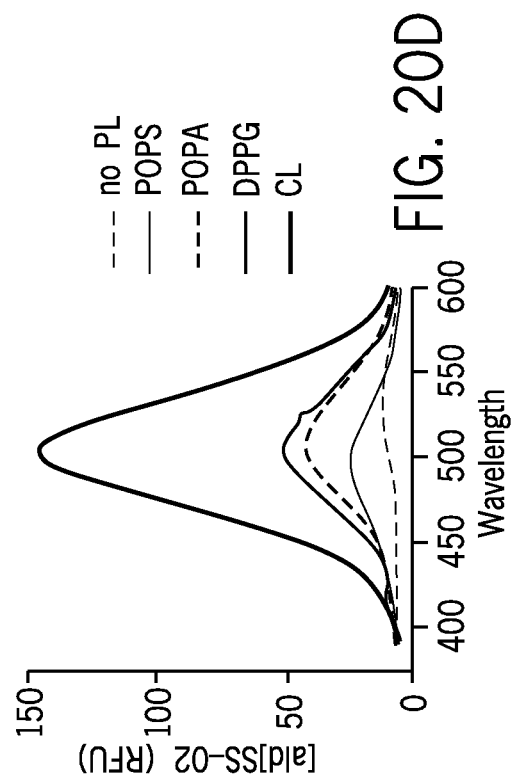
FIG. 20D shows representative emission spectra of POPS, POPA, DPPG, and cardiolipin following addition of 1 μM [ald]SS-02.

This SS-02-phospholipid interaction is specific for phospholipids with anionic headgroups such as phosphatidic acid (POPA), phosphatidylglycerol (DPPG), phosphatidylserine (POPS) and cardiolipin (CL). FIG. 20D shows representative emission spectra of 1 μM [ald]SS-02 alone, and following the addition of 10 μg/mL of POPS, POPA, DPPG or cardiolipin. Cardiolipin shows the highest affinity with [ald]SS-02 (FIG. 20D). No interaction was observed between [ald]SS-02 and phospholipids that also contain positive-charged amines in their headgroup, such as phosphatidylcholine (POPC) and phosphatidylethanolamine (POPE) (FIG. 20E), or with the neutral cholesterol (data not shown).

The interaction of [atn]SS-02 with free cardiolipin was also compared with that of [atn]SS-02 and a liposomal mixture of cardiolipin and POPC. Cardiolipin is normally only found in the inner mitochondrial membrane, together with phosphatidylcholine and phosphatidylethanolamine. Because of its small head group and four acyl chains, cardiolipin induces membrane curvature where the hydrophobic parts are exposed between neighboring molecules. When mixed with other bilayer phospholipids, cardiolipin is likely to form a non-bilayer microenvironment, possibly leading to a different interaction with SS-02.

Figure 20F:
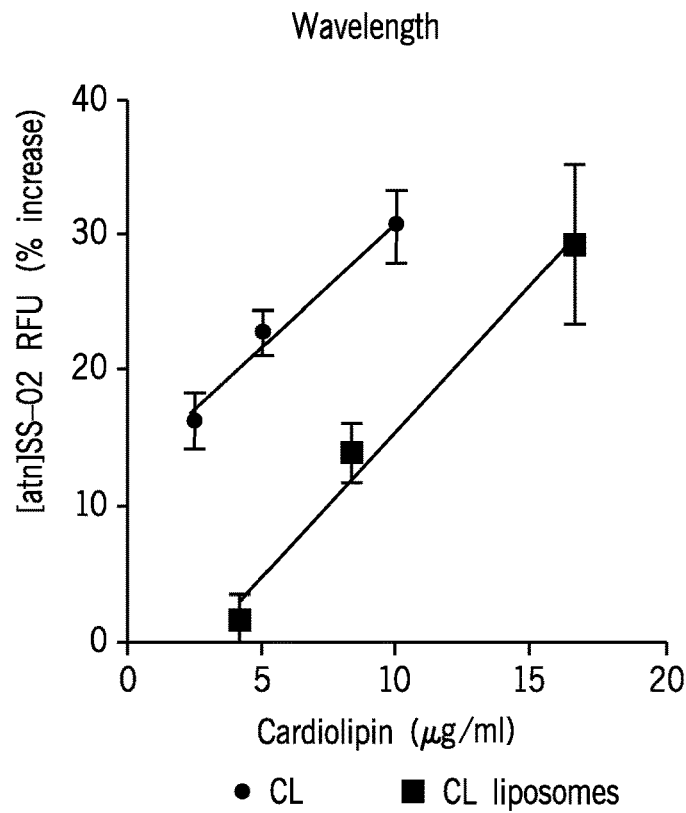
FIG. 20F is a line graph comparing the relative fluorescence of [atn]SS-02 added to various concentrations of cardiolipin and cardiolipin in liposomes.
Figure 20G:
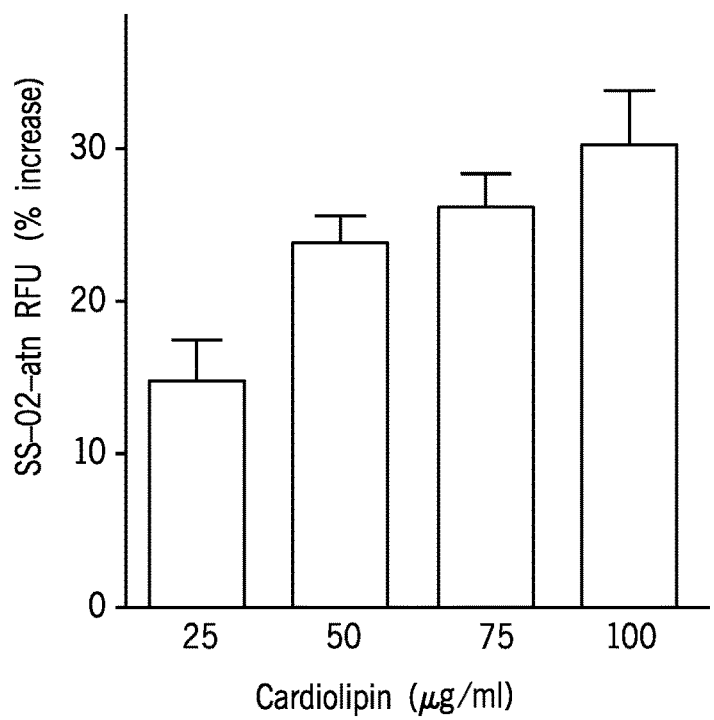
FIG. 20G is a bar graph showing the relative fluorescence of different concentrations of cardiolipin (25, 50, 75, 100 μg/mL) added to 1 μM [atn]SS-02.

A mixture of 1 μM [atn]SS-02 was made with liposomes composed of a 1:1 ratio of CL and POPC, and the emission intensity was measured. The graph in FIG. 20F shows a similar concentration-dependent interaction between [atn] SS-02 and cardiolipin/POPC liposomes (FIG. 20F). These results confirm that the SS peptides have high affinity for cardiolipin and this accounts for the selective concentration of the SS peptides in the inner mitochondrial membrane. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction.

Example 22

The Peptide SS-02 Interacts with Soluble Cytochrome c

Cytochrome c exists in three pools in mitochondria—a freely soluble pool in the intermembrane space, a pool that is loosely attached to cardiolipin via electrostatic interaction, and about 15-20% that is in a tight complex with cardiolipin via hydrophobic interaction. In order to determine whether SS-02 interacts with cytochrome c, fluorescence quenching of labeled SS-02 by cytochrome c was examined.

Materials and Methods

Interaction of SS peptides with horse heart cytochrome c in the absence or presence of free cardiolipin or cardiolipin/POPC (1:1) liposomes (prepared as described in Example 22) was examined by fluorescence quenching of [atn]SS-02 ($\lambda$ex/$\lambda$em=320/420 nm) and [ald]SS-02 ($\lambda$ex/$\lambda$em=360/510 nm) upon addition of cytochrome c (using a Hitachi F-4500 fluorescence spectrophotometer). The solvents used to dissolve cardiolipin and POPC had negligible effect on cytochrome c-dependent quenching of these peptides. All experiments were done in low ionic solution (deionized water) or 20 mM Hepes pH 7.4.

Uptake of [atn]SS-02 by isolated mitochondria or cytochrome c-deficient mitoplasts was determined by fluorescence quenching of [atn]SS-02 ($\lambda$ex/$\lambda$em=320/420) upon addition of a fresh mitochondrial or mitoplast suspension (0.35 mg).

Mitochondria were isolated from the kidney of male Sprague-Dawley rats (Charles River Laboratories International, Inc., Wilmington, Mass.) weighing 250 to 300 g. Excised kidneys were cut and incubated in wash buffer (200 mM mannitol, 10 mM sucrose, 5 mM HEPES, 1 g/L fatty-acid-free BSA, to pH to 7.4 with KOH) on ice for 10 minutes. Samples were washed 2 times in isolation buffer (wash buffer with 1 mM EGTA), homogenized for 3 minutes, and then centrifuged in 20 ml of isolation buffer at 900×g for 10 minutes. The white fatty acid layer was then removed and the pellet was discarded. The supernatant was centrifuged at 11,000×g for 10 minutes, and the pellet was re-suspended in 800 µl of wash buffer and kept on ice for further analysis.

Mitoplasts deficient in cytochrome c were prepared by first treating fresh or once-frozen mitochondria with 3.3 mg/ml digitonin for 45 minutes on ice, in order to remove the mitochondrial outer membrane. To remove electrostatically-bound cytochrome c, 150 mM KCl pH 7.4 was then added to the mix and centrifuged at 19,000×g for 30 minutes. The pellet was collected and re-dissolved in wash buffer and stored on ice until use. Only mitoplast preparations that responded to the addition of 200 nM exogenous cytochrome c by 4-5 fold increase in mitochondrial respiration (oxygen consumption) were used in the study.

Results

Figure 21A:
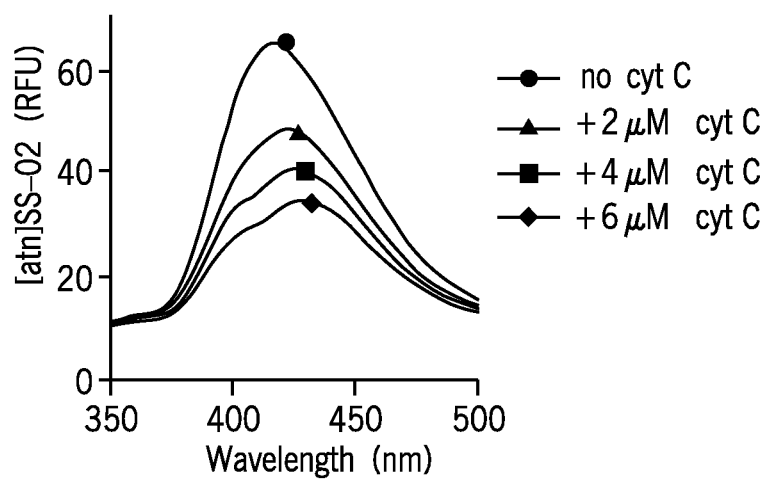
FIG. 21A shows representative emission spectra of [atn] SS-02 (1 μM) added to various concentrations (2, 4, 6 μM) of cytochrome c.
Figure 21B:
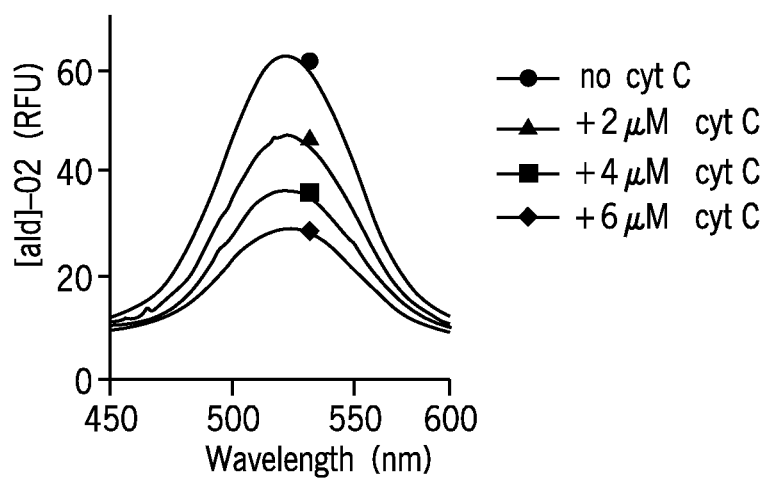
FIG. 21B shows representative emission spectra of [ald]SS-02 (1 μM) added to various concentrations (2, 4, 6 μM) of cytochrome c.
Figure 21C:
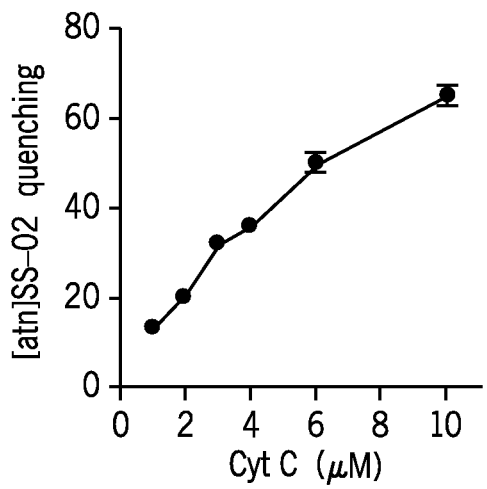
FIG. 21C is a line graph of quenching of [atn]SS-02 (1 μM) fluorescence by addition of increasing concentrations (1-10 μM) of cytochrome c.

Fluorescence quenching studies show that the SS peptides can interact with soluble cytochrome c. Addition of cytochrome c resulted in concentration-dependent quenching of both [atn]SS-02 and [ald]SS-02 with no change in $\lambda$max (FIGS. 21A and 21B). This quenching by cytochrome c is dose-dependent and readily observed at 1:1 ratio of peptide to cytochrome c (FIG. 21C). Furthermore, this quenching could not be displaced by albumin. Fluorescence emission of [ant]SS-02 was quenched by sequential addition of 2 µM of cytochrome c (labeled C in FIG. 21H). Additions of 75 µg/ml of BSA (labeled A in FIG. 21H) (total of 300 µg/ml) did not reverse quenching. Fluorescence emission of [ant]SS-02 was also specific for the peptides, as no quenching was observed with other mitochondria-targeted fluorescent probes such as TMRM (tetramethylrhodamine methyl ester). Additions of 2 µM of cytochrome c (labeled C in FIG. 21I) slightly quenched TMRM fluorescence and 75 µg/ml of BSA (labeled A in FIG. 21I) (total of 225 µg/ml) completely reversed quenching.

It is known that the intrinsic fluorescence of Trp57 in cytochrome c is 98% quenched by the heme group in natively-folded cytochrome c and is reduced to 40% when cytochrome c is unfolded (Tsong, 1973, Biochemistry 12:2209-2214). Thus, such pronounced quenching of SS peptide analogs by cytochrome c suggests that the peptides are localized in close proximity to the heme to allow energy transfer to this resonance acceptor.

Figure 21D:
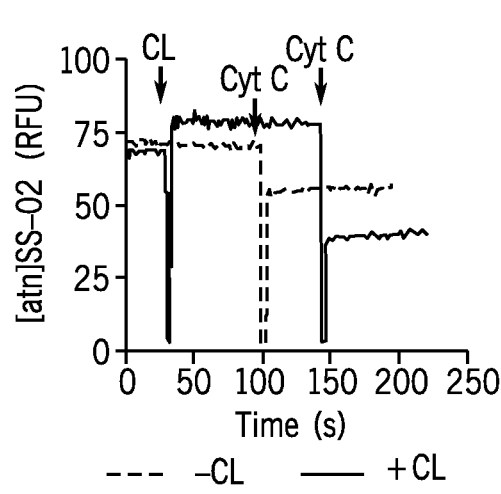
FIG. 21D is a graph of relative fluorescence over time of [atn]SS-02 (1 μM) and cytochrome c (2 μM) in the presence and absence of cardiolipin (10 μg/ml).
Figure 21E:
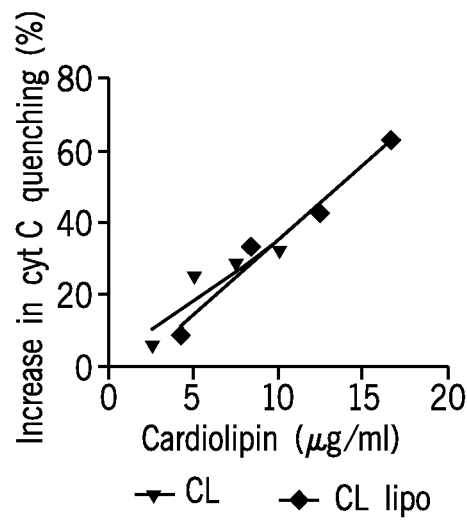
FIG. 21E is a line graph of quenching of [atn]SS-02 (1 μM) fluorescence by cytochrome c in increasing concentrations of cardiolipin alone or cardiolipin mixed with liposomes.

The interaction of the SS peptides with cytochrome c was found to be enhanced in the presence of cardiolipin. The quenching of [atn]SS-02 at 420 nm by cytochrome c in the absence and presence of cardiolipin was compared. The addition of 2 µM cytochrome c to 1 µM [atn]SS-02 resulted in ~20% quenching of the fluorescent signal in the absence of cardiolipin, but almost 50% quenching in the presence of 10 µg/mL cardiolipin (FIG. 21D). The interaction between cytochrome c and [atn]SS-02 was potentiated by either free cardiolipin or cardiolipin liposomes in a dose-dependent manner (FIG. 21E). This finding shows that the presence of cardiolipin allowed [atn]SS-02 to penetrate even closer to the heme group deep within cytochrome c to increase resonance transfer.

Figure 21F:
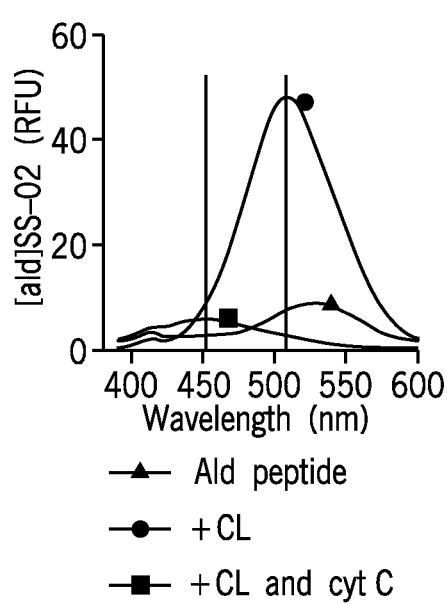
FIG. 21F shows representative emission spectra of [ald]SS-02 alone, in the presence of cardiolipin (CL), and in the presence of cardiolipin and cytochrome c.

The polarity-sensitive [ald]SS-02 allowed further investigation of the interaction of SS-02 with cytochrome c in the presence of cardiolipin. The addition of cytochrome c to cardiolipin and [ald]SS-02 caused a further blue shift in the $\lambda$max from 510 nm to 450 nm, showing that the peptide penetrated further into the deepest hydrophobic environment of the heme (FIG. 21F).

Figure 21G:
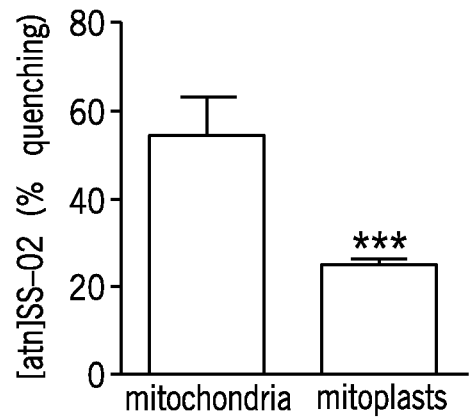
FIG. 21G is a bar graph comparing the percentage of fluorescence quenching of [atn]SS-02 in mitochondria versus cytochrome c-deficient mitoplasts.
Figure 21H:
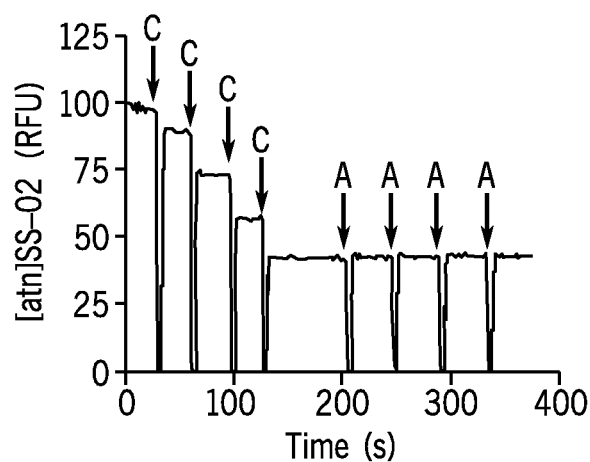
FIG. 21H shows representative fluorescence emission spectra from [ant]SS-02 quenched by sequential addition of 2 μM of cytochrome c (labeled C in FIG. 21H), with further addition of 75 μg/ml of BSA (labeled A in FIG. 21H).
Figure 21I:
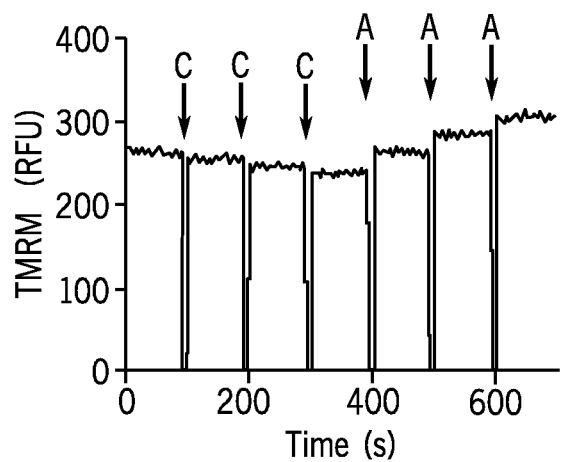
FIG. 21I shows representative fluorescence emissions from [ant] SS-02 quenched by sequential addition of TMRM (labeled C in FIG. 21I), with further addition of 75 μg/ml of BSA (labeled A in FIG. 21I).

Finally, to determine if these peptides can interact with cytochrome c that is hydrophobically bound to cardiolipin, a study was undertaken to examine the quenching of [atn]SS-02 by cytochrome c-deficient mitoplasts that have been treated with 125 mM KCl to remove electrostatically-bound cytochrome c. FIG. 21G shows that the quenching of [atn]SS-02 was appreciable in cytochrome c-deficient mitoplasts but was less than in intact mitochondria containing all three pools of cytochrome c. All together, these data show that the SS peptides can interact with free, electrostatically-bound, and hydrophobically-bound cytochrome c, and the peptides are localized very close to the heme environment. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction.

Example 23

SS-31 and SS-02 Inhibit Cytochrome c Oxidation by Cardiolipin

The peptides SS-31 and SS-02 were studied in order to determine whether they had any functional effects on the interaction between cytochrome c and cardiolipin. Cardiolipin is known to alter the function of cytochrome c, and readily oxidizes ferrous cytochrome c to ferric cytochrome c. The oxidation of ferrous cytochrome c in the presence of cardiolipin can be detected by loss of the 550 nm peak ($A_{550}$) in the absorbance spectrum of cytochrome c. Thus, the peptides SS-31 and SS-02 were examined for their ability to affect the loss of absorbance by cytochrome c caused by cardiolipin.

Materials and Methods

Cytochrome c (20 µM) was reduced by 50 µM ascorbic acid until all available functionally active cytochrome c was reduced. The reduction of cytochrome c was monitored by the appearance of a peak at 550 nm in its absorbance spectrum (Molecular Devices, Sunnyvale, Calif.). 100 µg/ml of cardiolipin was then added to the fully reduced cytochrome c in the presence or absence of SS peptides, and the oxidation of cytochrome c followed by the rate of decrease in the 550 nm peak. The rate of oxidation was calculated based on slope of the change in absorbance intensity of 550 nm over 570 nm.

Results

Figure 22A:
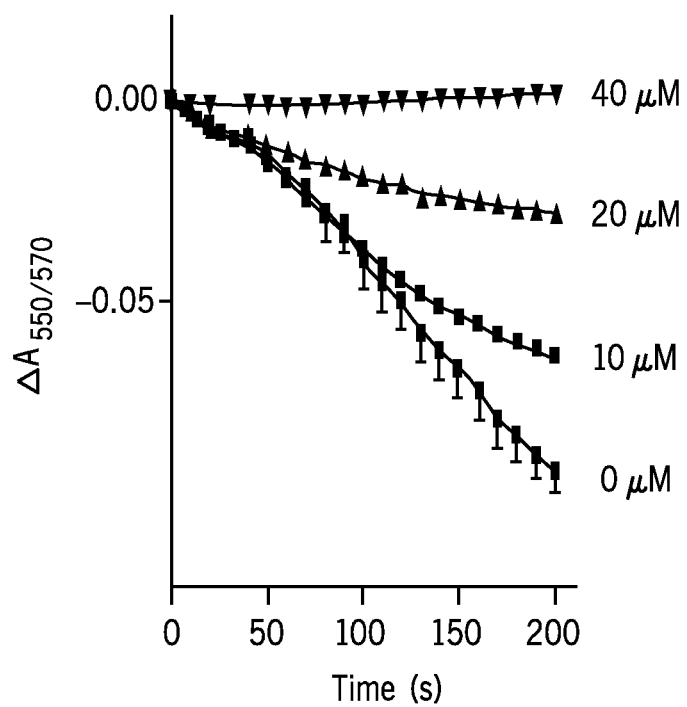
FIG. 22A is a plot of the change in $A_{550/570}$ for a mixture of cytochrome c and cardiolipin with the addition of various concentrations of (0, 10, 20, 40 μM) SS-31 peptide.

The loss of the 550 nm peak ($A_{550}$) in the absorbance spectrum of cytochrome c was prevented by the addition of SS-31 in a concentration-dependent manner (FIG. 22A).

Figure 22B:
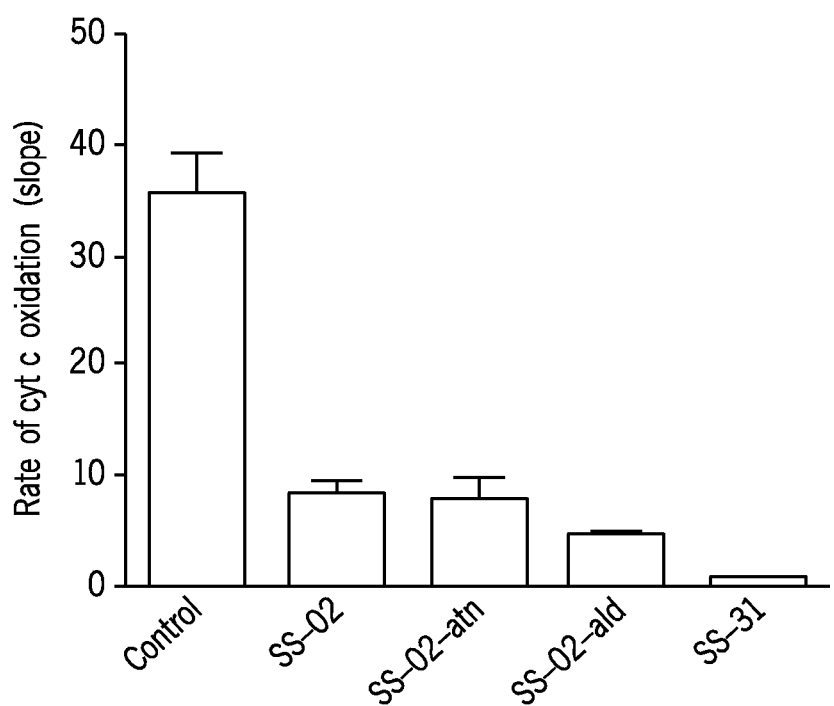
FIG. 22B is a bar graph comparing rates of cytochrome c oxidation for different peptides (control, SS-02, [atn]SS-02, [ald] SS-02, and SS-31).

This inhibition of cytochrome c oxidation was also observed for SS-02, [atn]SS-02, and [ald]SS-02 (FIG. 22B). These data suggest that the aromatic-cationic peptides can interfere with the structural interaction between cardiolipin and cytochrome c in the heme environment. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction. In addition, aromatic-cationic peptides of the present disclosure are useful for inhibiting cytochrome c oxidation by cardiolipin.

Example 24

SS-02 and SS-31 Peptide Analogs Interact Close to the Heme of Cytochrome c

Circular dichroism studies have shown the loss of the major negative Cotton peak in the Soret band of cytochrome c upon the addition of cardiolipin. The negative Cotton peak reflects electronic interactions ($\pi$-$\pi$*) between the heme and aromatic residue side chains, and the stability of the Fe-Met80 linkage. Thus, Circular Dichroism analysis was used to examine the impact of the SS peptide analogs on cardiolipin-induced changes in the heme environment of cytochrome c.

Materials and Methods

Circular Dichroism (CD) spectra were collected with an AVIA 62 DS spectrophotometer equipped with a sample temperature controller. CD spectra of the Soret region (370-450 nm) were recorded with 10-mm path length cells containing 20 mM Hepes, pH 7.4, and 10 µM cytochrome c, in the presence or absence of 30 µg/ml cardiolipin and different SS peptide analogs (SS-02, [atn]SS-02, [ald]SS-02, and SS-31). The maximum lipid concentration was kept low to avoid spectral distortions due to excessive light scattering. All measurements were done at 25° C. All spectra were corrected for background, and the final spectrum shown represents the average of at least three experiments.

Results

Figure 23:
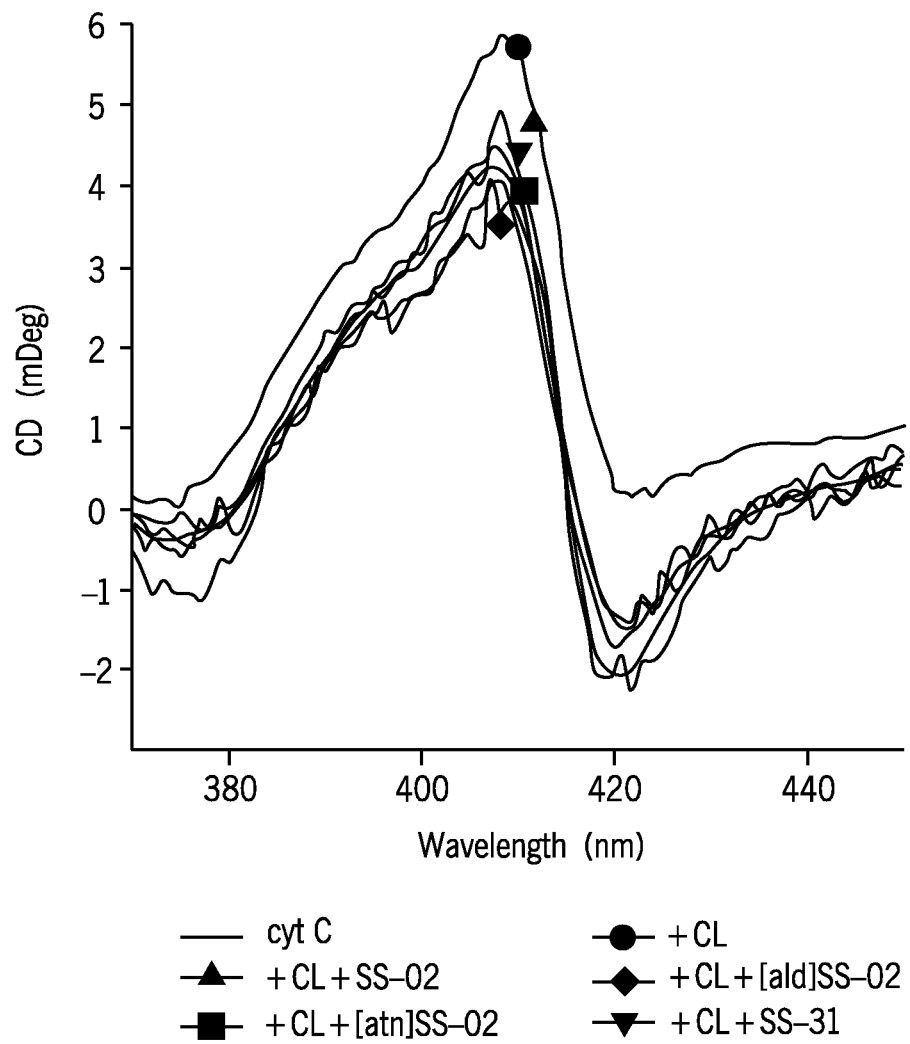
FIG. 23 is a chart showing representative Circular Dichroic spectra of the Soret band of ferric cytochrome c alone or in a complex with cardiolipin (CL) in the absence or presence of SS peptide analogs.

The addition of cardiolipin (30 µg/ml) to 10 µM cytochrome c resulted in the loss of the negative Cotton peak at 419 nm and this was prevented by the addition of either SS-02 or its fluorescent analogs ([atn]SS-02 and [ald]SS-02), or SS-31, in a 1:1 ratio with cytochrome c (FIG. 23). These data show that these aromatic-cationic peptides interact with cytochrome c in close proximity to the heme and prevent cardiolipin from breaking the $\pi$-$\pi$* interaction with aromatic side chains, and possibly preventing the rupture of the Fe-Met80 coordination. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction.

Example 25

SS-02 and SS-31 Peptide Analogs Inhibit Peroxidase Activity of Cytochrome c

Unlike pentacoordinated hemes such as hemoglobin and myoglobin, the two axial ligands (His18 and Met80) of Fe in cytochrome c prevent direct interaction of $H_2O_2$ with the catalytic metal site and cytochrome c in water has very low peroxidase activity. In the presence of cardiolipin, the peroxidase activity of cytochrome c increases by 2 orders of magnitude. By preventing the disruption of the Fe-Met80 bond induced by cardiolipin, the aromatic-cationic peptides may inhibit cytochrome c peroxidase activity. In order to examine inhibition of cytochrome c peroxidase activity by SS peptide analogs, Amplex® Red was used to measure peroxidase activity in the presence of cytochrome c, cardiolipin, and $H_2O_2$.

Materials and Methods

Assessment of cytochrome c peroxidase activity was achieved using the Amplex® Red assay (Invitrogen/Life Technologies, Carlsbad, Calif.). Amplex® Red is a reagent that reacts with H2O2 in a 1:1 stoichiometry to produce highly fluorescent resorufin ($\lambda$ex/$\lambda$em=570/585) in the presence of a peroxidase. In this assay, cytochrome c is added in place of horseradish peroxidase. 2 µM cytochrome c was incubated with cardiolipin or cardiolipin-POPC liposomes (10 µg/ml) for 1 min in 20 mM HEPES (pH 7.4) or deionized water prior to the addition of 50 µM Amplex® Red reagent and 10 µM $H_2O_2$, and the reaction was allowed to proceed for an additional 5 minutes. The continuous time course data were obtained using Hitachi F-4500 fluorescence spectrophotometer. When comparing the different SS peptide analogs (10 µM) in inhibiting peroxidase activity cytochrome c (2 µM) in the presence of cardiolipin (100 µg/ml), a microplate spectrofluorometer (Molecular Devices, Sunnyvale, Calif.) was used. Horseradish peroxidase (HRP) was used for comparison, and the HRP concentration (0.001 U/ml) was optimized to match the rate of Amplex® Red peroxidation by cardiolipin-cytochrome c complex.

Results

Figure 24:
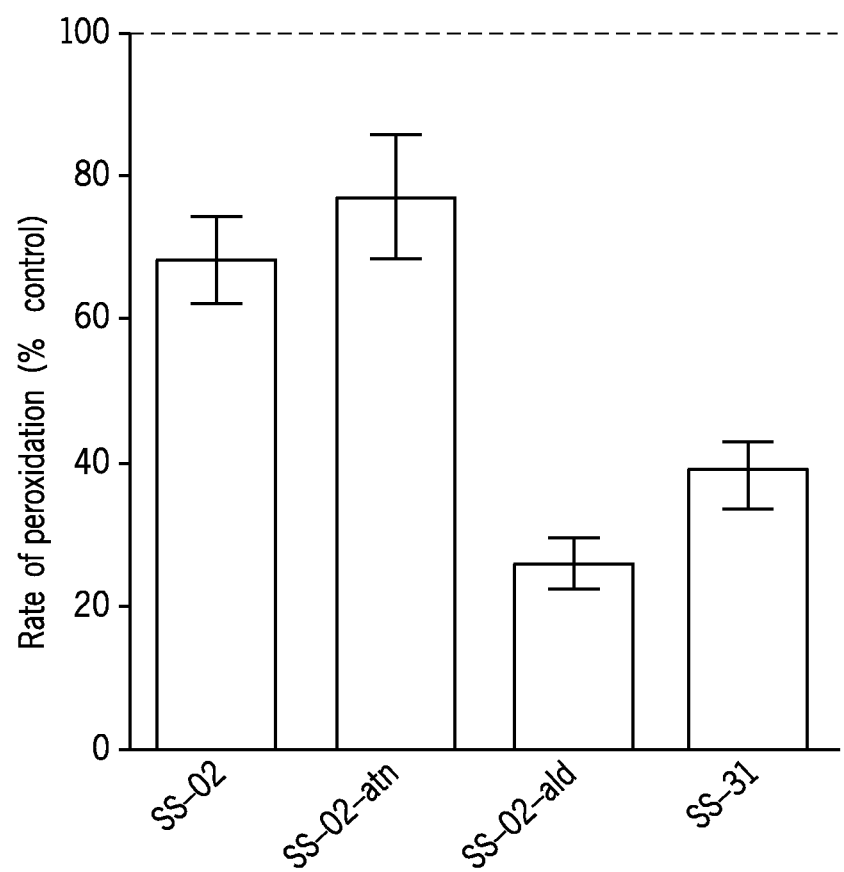
FIG. 24 is a bar graph comparing rates of cytochrome c peroxidation as a percentage of control for SS-02, [atn]SS-02, [ald]SS-02, and SS-31.

All four SS peptide analogs inhibited peroxidase activity of the cardiolipin-cytochrome c complex (FIG. 24). SS-02 and [atn]SS-02 reduce the peroxidation rate of cytochrome c to about 70% and 75% of control (respectively), while [ald]SS-02 and SS-31 reduce the peroxidation rate of cytochrome c to about 20% and 35% of control (respectively). Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction. In addition, aromatic-cationic peptides of the present disclosure are useful for inhibiting peroxidase activity in cytochrome c.

Example 26

Comparison of the Ability of Different Peptide Analogs to Prevent the Inhibition of Cytochrome c Reduction Caused by Cardiolipin Although the addition of cardiolipin greatly inhibits the rate of cytochrome c reduction induced by either glutathione or ascorbate, addition of SS-31 dose-dependently prevents this inhibition (see Example 16 and FIG. 14B). A study was undertaken to compare the ability of SS-31 to block the inhibition of cytochrome c reduction with that of SS-02, [atn]SS-02, and [ald]SS-02.

Materials and Methods

The time course of cytochrome c reduction by ascorbate was recorded at 550 nm and 570 nm using a 96-well plate reader (Molecular Devices, Sunnyvale, Calif.). For all reactions, cytochrome c was preincubated with cardiolipin in the presence or absence of SS peptides for 1 min. 20 µM of cytochrome c and 100 mg/ml of cardiolipin were found to be optimal, where cardiolipin would inhibit 90% to 100% of cytochrome c reduction regardless of the reducing agent. Ascorbate (50 μM) was added to initiate the reduction of cytochrome c, and the absorbance was recorded for 5 min. The rate of reduction was calculated based on slope of the change in absorbance intensity of 550 nm over 570 nm.

Results

Figure 25:
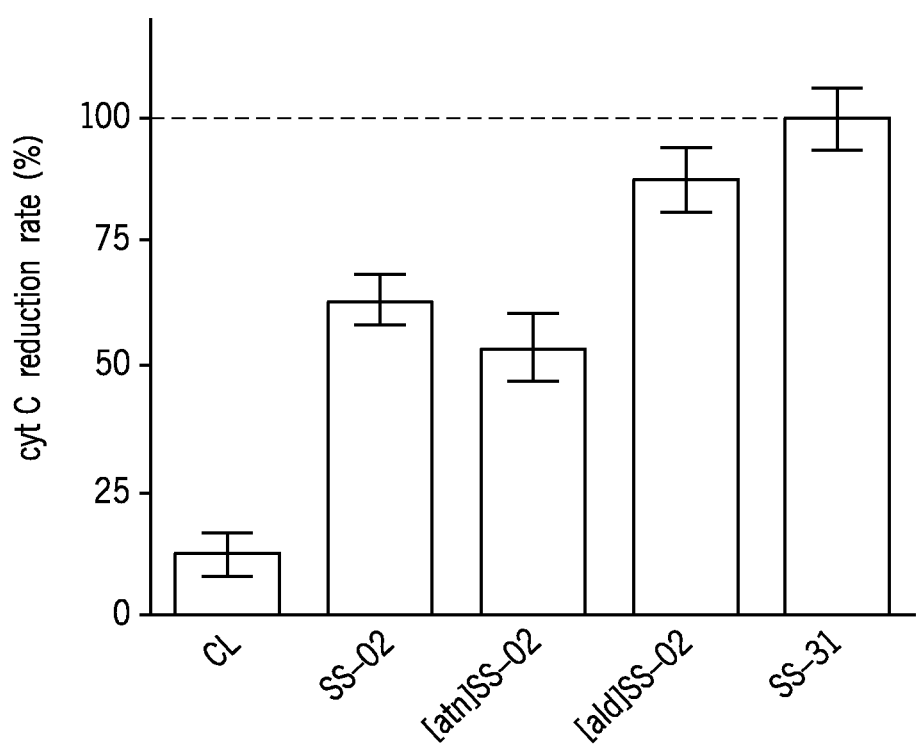
FIG. 25 is a bar graph comparing different peptide analogs (40 μM; SS-02, [atn]SS-02, [ald]SS-02, and SS-31) in their ability to promote reduction of cardiolipin-cytochrome c complex induced by ascorbate. CL is cardiolipin-cytochrome c complex without added SS peptide analog.

As shown in the bar graph of FIG. 25, the rate of cytochrome c reduction was reduced to 10% in the presence of cardiolipin. SS-31 was the most effective of the four peptides in preventing all the functions of the cardiolipin-cytochrome c complex, with the ability to allow 100% of the cytochrome c reduction rate while in the presence of cardiolipin. The reduction rate of cytochrome c in the present of SS-02 was about 60%, the reduction rate in the presence of [atn]SS-02 was about 50%, and the reduction rate in the presence of [ald]SS-02 was about 90%. Accordingly, aromatic-cationic peptides of the present disclosure are useful for the prevention or treatment of diseases or disorders characterized by dysregulation of cardiolipin and/or cytochrome c, and/or diseases or disorders characterized by dysregulation of the cardiolipin/cytochrome c interaction, such as systemic autoimmune diseases, e.g., systemic lupus erythematosus and/or antiphospholipid syndrome. Aromatic-cationic peptides of the present disclosure are useful to prevent the inhibition of cytochrome c reduction caused by cardiolipin.

REFERENCES

Tuominen E K J, Wallace C J A and Kinnunen P K J. Phospholipid-cytochrome c interaction. Evidence for the extended lipid anchorage. J Biol Chem 277:8822-8826, 2002.

Kalanxhi E and Wallace C J A. Cytochrome c impaled: investigation of the extended lipid anchorage of a soluble protein to mitochondrial membrane models. Biochem J 407:179-187, 2007.

Sinabaldi F, Howes B D, Piro M C, Polticelli F, Bombelli C, Ferri T et al. Extended cardiolipin anchorage to cytochrome c: a model for protein-mitochondrial membrane binding. J Biol Inorg Chem 15:689-700, 2010.

Sinabaldi F, Fiorucci L, Patriarca A, Lauceri R, Ferri T, Coletta M, Santucci R. Insights into Cytochrome c-cardiolipin interaction. Role played by ionic strength. Biochemistry 47:6928-6935, 2008.

Vladimirov Y A, Proskurnina E V, Izmailov D Y, Novikov A A m Brusnichkin A V, Osipov A N and Kagan V E. Mechanism of activation of cytochrome c peroxidase activity by cardiolipin. Biochemisty (Moscow) 71:989-997, 2006.

Basova L V, Kurnikov I V, Wang L, Ritob V B, Belikova N A, et al. Cardiolipin switch in mitochondria: Shutting off the reduction of cytochrome c and turning on the peroxidase activity. Biochemistry 46:3423-3434, 2007.

Kagan V E, Bayir A, Bayir H, Stoyanovsky D, et al. Mitochondria-targeted disruptors and inhibitors of cytochome c/cardiolipin peroxidase complexes. Mol Nutr Food Res 53:104-114, 2009.

Surewicz W K and Epand R M. Role of peptide structure in lipid-peptide interactions: A fluorescence study of the binding of pentagastrin-related pentapeptides to phospholipid vesicles. Biochemistry 23:6072-6077, 1984.

Hiratsuka T. New ribose-modified fluorescent analogs of adenine and guanine nucleotides available as substrates for various enzymes. Biochimica et Biophysica Acta 742:496-508, 1983.

Cohen B E, McAnaney T B, Park E S, Jan Y N, Boxer S G and Jan L Y. Probing protein electrostatics with a synthetic fluorescent amino acid. Science 296:1700-1703, 2001.

Santucci R and Ascoli F. The soret circular dichroism spectrum as a probe for the heme Fe(III)-Met(80) axial bond in horse cytochrome c. J Inorganic Biochem 68:211-214, 1997.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating antiphospholipid syndrome in a subject in need thereof, comprising: administering an effective amount of an aromatic-cationic peptide or a pharmaceutically acceptable salt thereof to the subject, wherein the aromatic-cationic peptide is 2',6'-Dmt-D-Arg-Ald-Lys-NH$_2$, where Ald is β-(6'-dimethylamino-2'-naphthoyl)alanine.

2. The method of claim 1, wherein the salt is an acetate salt or trifluoroacetate salt.

3. The method of claim 1, wherein the aromatic-cationic peptide is administered orally, parenterally, intravenously, subcutaneously, transdermally or by inhalation.

* * * * *